United States Patent
Bertin et al.

(10) Patent No.: US 7,083,944 B1
(45) Date of Patent: Aug. 1, 2006

(54) MOLECULES OF THE CARD-RELATED PROTEIN FAMILY AND USES THEREOF

(75) Inventors: John Bertin, Watertown, MA (US); Keith E. Robison, Wilmington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 240 days.

(21) Appl. No.: 09/697,089

(22) Filed: Oct. 26, 2000

Related U.S. Application Data

(60) Provisional application No. 60/161,822, filed on Oct. 27, 1999.

(51) Int. Cl.
| | |
|---|---|
| *C07K 14/47* | (2006.01) |
| *C12N 15/12* | (2006.01) |
| *C12N 15/63* | (2006.01) |
| *C12N 1/00* | (2006.01) |
| *C12N 5/10* | (2006.01) |

(52) U.S. Cl. .............. 435/69.1; 435/320.1; 435/252.3; 435/254.11; 435/325; 536/23.5

(58) Field of Classification Search ............... 536/23.5; 435/69.1, 320.1, 325, 252.3
See application file for complete search history.

(56) References Cited

U.S. PATENT DOCUMENTS

2002/0176853 A1 11/2002 Reed et al.

OTHER PUBLICATIONS

Adams et al. Database Genbank Accession No. AQ12439. National Library of Medicine, Bethesda, MD, Aug. 29, 1998.*
Hazan et al. Genbank Accession AL121653, Sep. 30, 1999. Bethesda, MD.: National Library of Medicine (www.ncbi.nlm.nih.gov).*
K. Hofmann, "The modular nature of apoptotic signaling proteins," Cell Mol. Life Sci., 55:1113-1128 (1999).
Koseki et al., "CIPER, a Novel NF κB-activating Protein Containing a Caspase Recruitment Domain with Homology to *Herpesvirus*-2 Protein E10," J. Biol Chemistry, 274(15):9955-9961 (Apr. 9, 1999).
GenBank Accession No. AQ309494, Adams et al. (Dec. 22, 1998).
Bertin et al., "Human CARD4 Protein Is a Novel CED-4/Apaf-1 Cell Death Family Member That Activates NF-κB," The Journal of Biological Chemistry, 274(19):12955-12958 (May 7, 1999).
Hofmann et al., "The CARD domain: a new apoptotic signalling motif," TIBS 22:155-156 (1997).
Imai et al., "The CED-4-homologous Protein FLASH is involved in Fas-mediated activation of caspase-8 during apoptosis," NATURE, 398:777-785 (Apr. 1999).
Nicholson, "Caspase structure, proteolytic substrates, and function during apoptotic cell death," Cell Death and Differentiation, 6:1028-1042 (1999).
GenBank™ Accession No. AC010968, Aug. 18, 2000.
GenBank™ Accession No. AI263294, Feb. 3, 1999.
GenBank™ Accession No. AL121653, Mar. 2, 2000.
GenBank™ Accession No. Q13075, Aug. 20, 2001.
Incyte LGtemplates Accession No. 328193, LifeSeq Gold 5.0, Oct. 1999 (local alignments obtained from a BLAST search with a query sequence).
Incyte LGtemplates Accession No. 402895, LifeSeq Gold 5.0, Oct. 1999 (local alignments obtained from a BLAST search with a query sequence).

* cited by examiner

*Primary Examiner*—Gabriele Bugaisky
(74) *Attorney, Agent, or Firm*—Fish & Richardson P.C.

(57) ABSTRACT

Novel CARD-12 polypeptides, proteins, and nucleic acid molecules are disclosed. In addition to isolated CARD-12 proteins, the invention further provides CARD-12, fusion proteins, antigenic peptides and anti-CARD-12 antibodies. The invention also provides CARD-12 nucleic acid molecules, recombinant expression vectors containing a nucleic acid molecule of the invention, host cells into which the expression vectors have been introduced and non-human transgenic animals in which a CARD-12 gene has been introduced or disrupted. Diagnostic, screening and therapeutic methods utilizing compositions of the invention are also provided.

35 Claims, 16 Drawing Sheets

```
cgctctagcc cggtgggaag ctttcatcca gaaca atg aat ttc ata aag gac        53
                                       Met Asn Phe Ile Lys Asp
                                       1               5 aat agc cga gcc ctt att caa aga atg gga atg act gtt ata aag caa       101
Asn Ser Arg Ala Leu Ile Gln Arg Met Gly Met Thr Val Ile Lys Gln
            10                  15                  20 atc aca gat gac cta ttt gta tgg aat gtt ctg aat cgc gaa gaa gta       149
Ile Thr Asp Asp Leu Phe Val Trp Asn Val Leu Asn Arg Glu Glu Val
            25                  30                  35 aac atc att tgc tgc gag aag gtg gag cag gat gct gct aga ggg atc       197
Asn Ile Ile Cys Cys Glu Lys Val Glu Gln Asp Ala Ala Arg Gly Ile
            40                  45                  50 att cac atg att ttg aaa aag ggt tca gag tcc tgt aac ctc ttt ctt       245
Ile His Met Ile Leu Lys Lys Gly Ser Glu Ser Cys Asn Leu Phe Leu
55                  60                  65                  70 aaa tcc ctt aag gag tgg aac tat cct cta ttt cag gac ttg aat gga       293
Lys Ser Leu Lys Glu Trp Asn Tyr Pro Leu Phe Gln Asp Leu Asn Gly
                75                  80                  85 caa agt ctt ttt cat cag aca tca gaa gga gac ttg gac gat ttg gct       341
Gln Ser Leu Phe His Gln Thr Ser Glu Gly Asp Leu Asp Asp Leu Ala
            90                  95                  100 cag gat tta aag gac ttg tac cat acc cca tct ttt ctg aac ttt tat       389
Gln Asp Leu Lys Asp Leu Tyr His Thr Pro Ser Phe Leu Asn Phe Tyr
            105                 110                 115 ccc ctt ggt gaa gat att gac att att ttt aac ttg aaa agc acc ttc       437
Pro Leu Gly Glu Asp Ile Asp Ile Ile Phe Asn Leu Lys Ser Thr Phe
            120                 125                 130 aca gaa cct gtc ctg tgg agg aag gac caa cac cat cac cgc gtg gag       485
Thr Glu Pro Val Leu Trp Arg Lys Asp Gln His His His Arg Val Glu
135                 140                 145                 150 cag ctg acc ctg aat ggc ctc ctg cag gct ctt cag agc ccc tgc atc       533
Gln Leu Thr Leu Asn Gly Leu Leu Gln Ala Leu Gln Ser Pro Cys Ile
                155                 160                 165 att gaa ggg gaa tct ggc aaa ggc aag tcc act ctg ctg cag cgc att       581
Ile Glu Gly Glu Ser Gly Lys Gly Lys Ser Thr Leu Leu Gln Arg Ile
            170                 175                 180 gcc atg ctc tgg ggc tcc gga aag tgc aag gct ctg acc aag ttc aaa       629
Ala Met Leu Trp Gly Ser Gly Lys Cys Lys Ala Leu Thr Lys Phe Lys
            185                 190                 195 ttc gtc ttc ttc ctc cgt ctc agc agg gcc cag ggt gga ctt ttt gaa       677
Phe Val Phe Phe Leu Arg Leu Ser Arg Ala Gln Gly Gly Leu Phe Glu
            200                 205                 210
```

FIG. 1A

```
acc ctc tgt gat caa ctc ctg gat ata cct ggc aca atc agg aag cag    725
Thr Leu Cys Asp Gln Leu Leu Asp Ile Pro Gly Thr Ile Arg Lys Gln
215             220                 225                 230 aca ttc atg gcc atg ctg ctg aag ctg cgg cag agg gtt ctt ttc ctt    773
Thr Phe Met Ala Met Leu Leu Lys Leu Arg Gln Arg Val Leu Phe Leu
                235                 240                 245 ctt gat ggc tac aat gaa ttc aag ccc cag aac tgc cca gaa atc gaa    821
Leu Asp Gly Tyr Asn Glu Phe Lys Pro Gln Asn Cys Pro Glu Ile Glu
            250                 255                 260 gcc ctg ata aag gaa aac cac cgc ttc aag aac atg gtc atc gtc acc    869
Ala Leu Ile Lys Glu Asn His Arg Phe Lys Asn Met Val Ile Val Thr
        265                 270                 275 act acc act gag tgc ctg agg cac ata cgg cag ttt ggt gcc ctg act    917
Thr Thr Thr Glu Cys Leu Arg His Ile Arg Gln Phe Gly Ala Leu Thr
    280                 285                 290 gct gag gtg ggg gat atg aca gaa gac agc gcc cag gct ctc atc cga    965
Ala Glu Val Gly Asp Met Thr Glu Asp Ser Ala Gln Ala Leu Ile Arg
295                 300                 305                 310 gaa gtg ctg atc aag gag ctt gct gaa ggc ttg ttg ctc caa att cag   1013
Glu Val Leu Ile Lys Glu Leu Ala Glu Gly Leu Leu Leu Gln Ile Gln
                315                 320                 325 aaa tcc agg tgc ttg agg aat ctc atg aag acc cct ctc ttt gtg gtc   1061
Lys Ser Arg Cys Leu Arg Asn Leu Met Lys Thr Pro Leu Phe Val Val
            330                 335                 340 atc act tgt gca atc cag atg ggt gaa agt gag ttc cac tct cac aca   1109
Ile Thr Cys Ala Ile Gln Met Gly Glu Ser Glu Phe His Ser His Thr
        345                 350                 355 caa aca acg ctg ttc cat acc ttc tat gat ctg ttg ata cag aaa aac   1157
Gln Thr Thr Leu Phe His Thr Phe Tyr Asp Leu Leu Ile Gln Lys Asn
    360                 365                 370 aaa cac aaa cat aaa ggt gtg gct gca agt gac ttc att cgg agc ctg   1205
Lys His Lys His Lys Gly Val Ala Ala Ser Asp Phe Ile Arg Ser Leu
375                 380                 385                 390 gac cac tgt gga gac cta gct ctg gag ggt gtg ttc tcc cac aag ttt   1253
Asp His Cys Gly Asp Leu Ala Leu Glu Gly Val Phe Ser His Lys Phe
                395                 400                 405 gat ttc gaa ctg cag gat gtg tcc agc gtg aat gag gat gtc ctg ctg   1301
Asp Phe Glu Leu Gln Asp Val Ser Ser Val Asn Glu Asp Val Leu Leu
            410                 415                 420 aca act ggg ctc ctc tgt aaa tat aca gct caa agg ttc aag cca aag   1349
Thr Thr Gly Leu Leu Cys Lys Tyr Thr Ala Gln Arg Phe Lys Pro Lys
        425                 430                 435
```

FIG. 1B

```
tat aaa ttc ttt cac aag tca ttc cag gag tac aca gca gga cga aga    1397
Tyr Lys Phe Phe His Lys Ser Phe Gln Glu Tyr Thr Ala Gly Arg Arg
    440             445             450 ctc agc agt tta ttg acg tct cat gag cca gag gag gtg acc aag ggg    1445
Leu Ser Ser Leu Leu Thr Ser His Glu Pro Glu Glu Val Thr Lys Gly
455             460             465             470 aat ggt tac ttg cag aaa atg gtt tcc att tcg gac att aca tcc act    1493
Asn Gly Tyr Leu Gln Lys Met Val Ser Ile Ser Asp Ile Thr Ser Thr
                475             480             485 tat agc agc ctg ctc cgg tac acc tgt ggg tca tct gtg gaa gcc acc    1541
Tyr Ser Ser Leu Leu Arg Tyr Thr Cys Gly Ser Ser Val Glu Ala Thr
            490             495             500 agg gct gtt atg aag cac ctc gca gca gtg tat caa cac ggc tgc ctt    1589
Arg Ala Val Met Lys His Leu Ala Ala Val Tyr Gln His Gly Cys Leu
        505             510             515 ctc gga ctt tcc atc gcc aag agg cct ctc tgg aga cag gaa tct ttg    1637
Leu Gly Leu Ser Ile Ala Lys Arg Pro Leu Trp Arg Gln Glu Ser Leu
520             525             530 caa agt gtg aaa aac acc act gag caa gaa att ctg aaa gcc ata aac    1685
Gln Ser Val Lys Asn Thr Thr Glu Gln Glu Ile Leu Lys Ala Ile Asn
535             540             545             550 atc aat tcc ttt gta gag tgt ggc atc cat tta tat caa gag agt aca    1733
Ile Asn Ser Phe Val Glu Cys Gly Ile His Leu Tyr Gln Glu Ser Thr
                555             560             565 tcc aaa tca gcc ctg agc caa gaa ttt gaa gct ttc ttt caa ggt aaa    1781
Ser Lys Ser Ala Leu Ser Gln Glu Phe Glu Ala Phe Phe Gln Gly Lys
            570             575             580 agc tta tat atc aac tca ggg aac atc ccc gat tac tta ttt gac ttc    1829
Ser Leu Tyr Ile Asn Ser Gly Asn Ile Pro Asp Tyr Leu Phe Asp Phe
        585             590             595 ttt gaa cat ttg ccc aat tgt gca agt gct ctg gac ttc att aaa ctg    1877
Phe Glu His Leu Pro Asn Cys Ala Ser Ala Leu Asp Phe Ile Lys Leu
    600             605             610 gac ttt tat ggg gga gct atg gct tca tgg gaa aag gct gca gaa gac    1925
Asp Phe Tyr Gly Gly Ala Met Ala Ser Trp Glu Lys Ala Ala Glu Asp
615             620             625             630 aca ggt gga atc cac atg gaa gag gcc cca gaa acc tac att ccc agc    1973
Thr Gly Gly Ile His Met Glu Glu Ala Pro Glu Thr Tyr Ile Pro Ser
                635             640             645 agg gct gta tct ttg ttc ttc aac tgg aag cag gaa ttc agg act ctg    2021
Arg Ala Val Ser Leu Phe Phe Asn Trp Lys Gln Glu Phe Arg Thr Leu
            650             655             660
```

FIG. 1C

```
gag gtc aca ctc cgg gat ttc agc aag ttg aat aag caa gat atc aca      2069
Glu Val Thr Leu Arg Asp Phe Ser Lys Leu Asn Lys Gln Asp Ile Thr
        665                 670                 675 tat ctg ggg aaa ata ttc agc tct gcc aca agc ctc agg ctg caa ata      2117
Tyr Leu Gly Lys Ile Phe Ser Ser Ala Thr Ser Leu Arg Leu Gln Ile
        680                 685                 690 aag aga tgt gct ggt gtg gct gga agc ctc agt ttg gtc ctc agc acc      2165
Lys Arg Cys Ala Gly Val Ala Gly Ser Leu Ser Leu Val Leu Ser Thr
695                 700                 705                 710 tgt aag aac att tat tct ctc atg gtg gaa gcc agt ccc ctc acc ata      2213
Cys Lys Asn Ile Tyr Ser Leu Met Val Glu Ala Ser Pro Leu Thr Ile
                715                 720                 725 gaa gat gag agg cac atc aca tct gta aca aac ctg aaa acc ttg agt      2261
Glu Asp Glu Arg His Ile Thr Ser Val Thr Asn Leu Lys Thr Leu Ser
            730                 735                 740 att cat gac cta cag aat caa cgg ctg ccg ggt ggt ctg act gac agc      2309
Ile His Asp Leu Gln Asn Gln Arg Leu Pro Gly Gly Leu Thr Asp Ser
        745                 750                 755 ttg ggt aac ttg aag aac ctt aca aag ctc ata atg gat aac ata aag      2357
Leu Gly Asn Leu Lys Asn Leu Thr Lys Leu Ile Met Asp Asn Ile Lys
    760                 765                 770 atg aat gaa gaa gat gct ata aaa cta gct gaa ggc ctg aaa aac ctg      2405
Met Asn Glu Glu Asp Ala Ile Lys Leu Ala Glu Gly Leu Lys Asn Leu
775                 780                 785                 790 aag aag atg tgt tta ttt cat ttg acc cac ttg tct gac att gga gag      2453
Lys Lys Met Cys Leu Phe His Leu Thr His Leu Ser Asp Ile Gly Glu
                795                 800                 805 gga atg gat tac ata gtc aag tct ctg tca agt gaa ccc tgt gac ctt      2501
Gly Met Asp Tyr Ile Val Lys Ser Leu Ser Ser Glu Pro Cys Asp Leu
            810                 815                 820 gaa gaa att caa tta gtc tcc tgc tgc ttg tct gca aat gca gtg aaa      2549
Glu Glu Ile Gln Leu Val Ser Cys Cys Leu Ser Ala Asn Ala Val Lys
        825                 830                 835 atc cta gct cag aat ctt cac aat ttg gtc aaa ctg agc att ctt gat      2597
Ile Leu Ala Gln Asn Leu His Asn Leu Val Lys Leu Ser Ile Leu Asp
    840                 845                 850 tta tca gaa aat tac ctg gaa aaa gat gga aat gaa gct ctt cat gaa      2645
Leu Ser Glu Asn Tyr Leu Glu Lys Asp Gly Asn Glu Ala Leu His Glu
855                 860                 865                 870 ctg atc gac agg atg aac gtg cta gaa cag ctc acc gca ctg atg ctg      2693
Leu Ile Asp Arg Met Asn Val Leu Glu Gln Leu Thr Ala Leu Met Leu
                875                 880                 885
```

FIG. 1D

```
ccc tgg ggc tgt gac gtg caa ggc agc ctg agc agc ctg ttg aaa cat    2741
Pro Trp Gly Cys Asp Val Gln Gly Ser Leu Ser Ser Leu Leu Lys His
            890                 895                 900 ttg gag gag gtc cca caa ctc gtc aag ctt ggg ttg aaa aac tgg aga    2789
Leu Glu Glu Val Pro Gln Leu Val Lys Leu Gly Leu Lys Asn Trp Arg
        905                 910                 915 ctc aca gat aca gag att aga att tta ggt gca ttt ttt gga aag aac    2837
Leu Thr Asp Thr Glu Ile Arg Ile Leu Gly Ala Phe Phe Gly Lys Asn
    920                 925                 930 cct ctg aaa aac ttc cag cag ttg aat ttg gcg gga aat cgt gtg agc    2885
Pro Leu Lys Asn Phe Gln Gln Leu Asn Leu Ala Gly Asn Arg Val Ser
935                 940                 945                 950 agt gat gga tgg ctt gcc ttc atg ggt gta ttt gag aat ctt aag caa    2933
Ser Asp Gly Trp Leu Ala Phe Met Gly Val Phe Glu Asn Leu Lys Gln
            955                 960                 965 tta gtg ttt ttt gac ttt agt act aaa gaa ttt cta cct gat cca gca    2981
Leu Val Phe Phe Asp Phe Ser Thr Lys Glu Phe Leu Pro Asp Pro Ala
        970                 975                 980 tta gtc aga aaa ctt agc caa gtg tta tcc aag tta act ttt ctg caa    3029
Leu Val Arg Lys Leu Ser Gln Val Leu Ser Lys Leu Thr Phe Leu Gln
    985                 990                 995 gaa gct agg ctt gtt ggg tgg caa ttt gat gat gat gat ctc agt gtt    3077
Glu Ala Arg Leu Val Gly Trp Gln Phe Asp Asp Asp Asp Leu Ser Val
1000                1005                1010 att aca ggt gct ttt aaa cta gta act gct taa ataaagtgta ctcgaagcca  3130
Ile Thr Gly Ala Phe Lys Leu Val Thr Ala  *
1015                1020 gta                                                                3133
```

FIG. 1E

```
  1 ATGCTGAACGCTGGTCCCCTGGGCTCCCTTATTTCTTTCTCTATACTTTGTCTCTGTGTCTTTTTCTTTT
    TACGACTTGCGACCAGGGGACCCGAGGGAATAAAGAAAGAGATATGAAACAGAGACACAGAAAAGAAAA
  1▶ M  L  N  A  G  P  L  G  S  L  I  S  F  S  I  L  C  L  C  V  F  F  F

71 CCAAGTCTCTCGTTCCACCTAACGAGAAACACCCACAGAACAAGAAGGTATCTGGTCTACAAGAACTCGA
    GGTTCAGAGAGCAAGGTGGATTGCTCTTTGTGGGTGTCTTGTTCTTCCATAGACCAGATGTTCTTGAGCT
 24▶ S  K  S  L  V  P  P  N  E  K  H  P  Q  N  K  K  V  S  G  L  Q  E  L  E

141 GGCCTCACTGAAACGGAAAGCAAATACAAAGAAACTTTATTTTAAAAACATGTCTTGGTCTCCCAAGAAG
    CCGGAGTGACTTTGCCTTTCGTTTATGTTTCTTTGAAATAAAATTTTTGTACAGAACCAGAGGGTTCTTC
 47▶ A  S  L  K  R  K  A  N  T  K  K  L  Y  F  K  N  M  S  W  S  P  K  K

211 AGGGCAATTGGATTGCTCAGCCAGAGACCCTTGCAGGCAGACACACAAGCGGCTGGACGTCGAGAGGAAC
    TCCCGTTAACCTAACGAGTCGGTCTCTGGGAACGTCCGTCTGTGTGTTCGCCGACCTGCAGCTCTCCTTG
 71▶ R  A  I  G  L  L  S  Q  R  P  L  Q  A  D  T  Q  A  A  G  R  R  E

281 ACATCGGCGGAAGAACATACAAGCAGCTGGACGTCCAGAGGACGTTGAAGGGAGAATGCTGGCGGAAGAG
    TGTAGCCGCCTTCTTGTATGTTCGTCGACCTGCAGGTCTCCTGCAACTTCCCTCTTACGACCGCCTTCTC
 94▶ H  I  G  G  R  T  Y  K  Q  L  D  V  Q  R  T  L  K  G  E  C  W  R  K  S

351 CACACAACAGACATCGGCACGCCAGCAGGCCATCCACCAGAGGAACGACTCGGAGTTTGGCCTGGAGGTG
    GTGTGTTGTCTGTAGCCGTGCGGTCGTCCGGTAGGTGGTCTCCTTGCTGAGCCTCAAACCGGACCTCCAC
117▶ T  Q  Q  T  S  A  R  Q  Q  A  I  H  Q  R  N  D  S  E  F  G  L  E  V

421 AATTTCATAAAGGACAATAGCCGAGCCCTTATTCAAAGAATGGGAATGACTGTTATAAAGCAAATCACAG
    TTAAAGTATTTCCTGTTATCGGCTCGGGAATAAGTTTCTTACCCTTACTGACAATATTTCGTTTAGTGTC
141▶ N  F  I  K  D  N  S  R  A  L  I  Q  R  M  G  M  T  V  I  K  Q  I  T

491 ATGACCTATTTGTATGGAATGTTCTGAATCGCGAAGAAGTAAACATCATTTGCTGCGAGAAGGTGGAGCA
    TACTGGATAAACATACCTTACAAGACTTAGCGCTTCTTCATTTGTAGTAAACGACGCTCTTCCACCTCGT
164▶ D  D  L  F  V  W  N  V  L  N  R  E  E  V  N  I  I  C  C  E  K  V  E  Q

561 GGATGCTGCTAGAGGGATCATTCACATGATTTTGAAAAAGGGTTCAGAGTCCTGTAACCTCTTTCTTAAA
    CCTACGACGATCTCCCTAGTAAGTGTACTAAAACTTTTTCCCAAGTCTCAGGACATTGGAGAAAGAATTT
187▶ D  A  A  R  G  I  I  H  M  I  L  K  K  G  S  E  S  C  N  L  F  L  K

631 TCCCTTAAGGAGTGGAACTATCCTCTATTTCAGGACTTGAATGGACAAAGTTTTGAGGAGACACAGAATT
    AGGGAATTCCTCACCTTGATAGGAGATAAAGTCCTGAACTTACCTGTTTCAAAACTCCTCTGTGTCTTAA
211▶ S  L  K  E  W  N  Y  P  L  F  Q  D  L  N  G  Q  S  F  E  E  T  Q  N

701 GGGTCTTCTTTAACATCACCTCTTCTCTAATAGGTCTTTTTCATCAGACATCAGAAGGAGACTTGGACGA
    CCCAGAAGAAATTGTAGTGGAGAAGAGATTATCCAGAAAAAGTAGTCTGTAGTCTTCCTCTGAACCTGCT
234▶ W  V  F  F  N  I  T  S  S  L  I  G  L  F  H  Q  T  S  E  G  D  L  D  D

771 TTTGGCTCAGGATTTAAAGGACTTGTACCATACCCCATCTTTTCTGAACTTTTATCCCCTTGGTGAAGAT
    AAACCGAGTCCTAAATTTCCTGAACATGGTATGGGGTAGAAAAGACTTGAAAATAGGGGAACCACTTCTA
257▶ L  A  Q  D  L  K  D  L  Y  H  T  P  S  F  L  N  F  Y  P  L  G  E  D
```

FIG. 2A

```
 841 ATTGACATTATTTTTAACTTGAAAAGCACCTTCACAGAACCTGTCCTGTGGAGGAAGGACCAACACCATC
     TAACTGTAATAAAAATTGAACTTTTCGTGGAAGTGTCTTGGACAGGACACCTCCTTCCTGGTTGTGGTAG
 281▶ I  D  I  F  N  L  K  S  T  F  T  E  P  V  L  W  R  K  D  Q  H  H

911 ACCGCGTGGAGCAGCTGACCCTGAATGGCCTCCTGCAGGCTCTTCAGAGCCCCTGCATCATTGAAGGGGA
     TGGCGCACCTCGTCGACTGGGACTTACCGGAGGACGTCCGAGAAGTCTCGGGGACGTAGTAACTTCCCCT
 304▶ H  R  V  E  Q  L  T  L  N  G  L  L  Q  A  L  Q  S  P  C  I  I  E  G  E

981 ATCTGGCAAAGGCAAGTCCACTCTGCTGCAGCGAATTGCCATGCTCTGGGGCTCCGGAAAGTGCAAGGCT
     TAGACCGTTTCCGTTCAGGTGAGACGACGTCGCTTAACGGTACGAGACCCCGAGGCCTTTCACGTTCCGA
 327▶ S  G  K  G  K  S  T  L  L  Q  R  I  A  M  L  W  G  S  G  K  C  K  A

1051 CTGACCAAGTTCAAATTCGTCTTCTTCCTCCGTCTCAGCAGGGCCCAGGGTGGACTTTTTGAAACCCTCT
     GACTGGTTCAAGTTTAAGCAGAAGAAGGAGGCAGAGTCGTCCCGGGTCCCACCTGAAAAACTTTGGGAGA
 351▶ L  T  K  F  K  F  V  F  F  L  R  L  S  R  A  Q  G  G  L  F  E  T  L

1121 GTGATCAACTCCTGGATATACCTGGCACAATCAGGAAGCAGACATTCATGGCCATGCTGCTGAAGCTGCG
     CACTAGTTGAGGACCTATATGGACCGTGTTAGTCCTTCGTCTGTAAGTACCGGTACGACGACTTCGACGC
 374▶ C  D  Q  L  L  D  I  P  G  T  I  R  K  Q  T  F  M  A  M  L  L  K  L  R

1191 GCAGAGGGTTCTTTTTCCTTCTTGATGGCTACAATGAATTCAAGCCCCAGAACTGCCCAGAAATCGAAGCC
     CGTCTCCCAAGAAAAGGAAGAACTACCGATGTTACTTAAGTTCGGGGTCTTGACGGGTCTTTAGCTTCGG
 397▶ Q  R  V  L  F  L  L  D  G  Y  N  E  F  K  P  Q  N  C  P  E  I  E  A

1261 CTGATAAAGGAAAACCACCGCTTCAAGAACATGGTCATCGTCACCACTACCACTGAGTGCCTGAGGCACA
     GACTATTTCCTTTTGGTGGCGAAGTTCTTGTACCAGTAGCAGTGGTGATGGTGACTCACGGACTCCGTGT
 421▶ L  I  K  E  N  H  R  F  K  N  M  V  I  V  T  T  T  T  E  C  L  R  H

1331 TACGGCAGTTTGGTGCCCTGACTGCTGAGGTGGGGGATATGACAGAAGACAGCGCCCAGGCTCTCATCCG
     ATGCCGTCAAACCACGGGACTGACGACTCCACCCCCTATACTGTCTTCTGTCGCGGGTCCGAGAGTAGGC
 444▶ I  R  Q  F  G  A  L  T  A  E  V  G  D  M  T  E  D  S  A  Q  A  L  I  R

1401 AGAAGTGCTGATCAAGGAGCTTGCTGAAGGCTTGTTGCTCCAAATTCAGAAATCCAGGTGCTTGAGGAAT
     TCTTCACGACTAGTTCCTCGAACGACTTCCGAACAACGAGGTTTAAGTCTTTAGGTCCACGAACTCCTTA
 467▶ E  V  L  I  K  E  L  A  E  G  L  L  L  Q  I  Q  K  S  R  C  L  R  N

1471 CTCATGAAGACCCCTCTCTTTGTGGTCATCACTTGTGCAATCCAGATGGGTGAAAGTGAGTTCCACTCTC
     GAGTACTTCTGGGGAGAGAAACACCAGTAGTGAACACGTTAGGTCTACCCACTTTCACTCAAGGTGAGAG
 491▶ L  M  K  T  P  L  F  V  V  I  T  C  A  I  Q  M  G  E  S  E  F  H  S

1541 ACACACAAACAACGCTGTTCCATACCTTCTATGATCTGTTGATACAGAAAAACAAACACAAACATAAAGG
     TGTGTGTTTGTTGCGACAAGGTATGGAAGATACTAGACAACTATGTCTTTTTGTTTGTGTTTGTATTTCC
 514▶ H  T  Q  T  T  L  F  H  T  F  Y  D  L  L  I  Q  K  N  K  H  K  H  K  G

1611 TGTGGCTGCAAGTGACTTCATTCGGAGCCTGGACCACTGTGGAGACCTAGCTCTGGAGGGTGTGTTCTCC
     ACACCGACGTTCACTGAAGTAAGCCTCGGACCTGGTGACACCTCTGGATCGAGACCTCCCACACAAGAGG
 537▶ V  A  A  S  D  F  I  R  S  L  D  H  C  G  D  L  A  L  E  G  V  F  S

1681 CACAAGTTTGATTTCGAACTGCAGGATGTGTCCAGCGTGAATGAGGATGTCCTGCTGACAACTGGGCTCC
     GTGTTCAAACTAAAGCTTGACGTCCTACACAGGTCGCACTTACTCCTACAGGACGACTGTTGACCCGAGG
 561▶ H  K  F  D  F  E  L  Q  D  V  S  S  V  N  E  D  V  L  L  T  T  G  L
```

FIG. 2B

```
1751 TCTGTAAATATACAGCTCAAAGGTTCAAGCCAAAGTATAAATTCTTTCACAAGTCATTCCAGGAGTACAC
     AGACATTTATATGTCGAGTTTCCAAGTTCGGTTTCATATTTAAGAAAGTGTTCAGTAAGGTCCTCATGTG
584▶ L  C  K  Y  T  A  Q  R  F  K  P  K  Y  K  F  F  H  K  S  F  Q  E  Y  T

1821 AGCAGGACGAAGACTCAGCAGTTTATTGACGTCTCATGAGCCAGAGGAGGTGACCAAGGGGAATGGTTAC
     TCGTCCTGCTTCTGAGTCGTCAAATAACTGCAGAGTACTCGGTCTCCTCCACTGGTTCCCCTTACCAATG
607▶ A  G  R  R  L  S  S  L  L  T  S  H  E  P  E  E  V  T  K  G  N  G  Y

1891 TTGCAGAAAATGGTTTCCATTTCGGACATTACATCCACTTATAGCAGCCTGCTCCGGTACACCTGTGGGT
     AACGTCTTTTACCAAAGGTAAAGCCTGTAATGTAGGTGAATATCGTCGGACGAGGCCATGTGGACACCCA
631▶ L  Q  K  M  V  S  I  S  D  I  T  S  T  Y  S  S  L  L  R  Y  T  C  G

1961 CATCTGTGGAAGCCACCAGGGCTGTTATGAAGCACCTCGCAGCAGTGTATCAACACGGCTGCCTTCTCGG
     GTAGACACCTTCGGTGGTCCCGACAATACTTCGTGGAGCGTCGTCACATAGTTGTGCCGACGGAAGAGCC
654▶ S  S  V  E  A  T  R  A  V  M  K  H  L  A  A  V  Y  Q  H  G  C  L  L  G

2031 ACTTTCCATCGCCAAGAGGCCTCTCTGGAGACAGGAATCTTTGCAAAGTGTGAAAAACACCACTGAGCAA
     TGAAAGGTAGCGGTTCTCCGGAGAGACCTCTGTCCTTAGAAACGTTTCACACTTTTTGTGGTGACTCGTT
677▶ L  S  I  A  K  R  P  L  W  R  Q  E  S  L  Q  S  V  K  N  T  T  E  Q

2101 GAAATTCTGAAAGCCATAAACATCAATTCCTTTGTAGAGTGTGGCATCCATTTATATCAAGAGAGTACAT
     CTTTAAGACTTTCGGTATTTGTAGTTAAGGAAACATCTCACACCGTAGGTAAATATAGTTCTCTCATGTA
701▶ E  I  L  K  A  I  N  I  N  S  F  V  E  C  G  I  H  L  Y  Q  E  S  T

2171 CCAAATCAGCCCTGAGCCAAGAATTTGAAGCTTTCTTTCAAGGTAAAAGCTTATATATCAACTCAGGGAA
     GGTTTAGTCGGGACTCGGTTCTTAAACTTCGAAAGAAAGTTCCATTTTCGAATATATAGTTGAGTCCCTT
724▶ S  K  S  A  L  S  Q  E  F  E  A  F  F  Q  G  K  S  L  Y  I  N  S  G  N

2241 CATCCCCGATTACTTATTTGACTTCTTTGAACATTTGCCCAATTGTGCAAGTGCCCTGGACTTCATTAAA
     GTAGGGGCTAATGAATAAACTGAAGAAACTTGTAAACGGGTTAACACGTTCACGGGACCTGAAGTAATTT
747▶ I  P  D  Y  L  F  D  F  F  E  H  L  P  N  C  A  S  A  L  D  F  I  K

2311 CTGGACTTTTATGGGGGAGCTATGGCTTCATGGGAAAAGGCTGCAGAAGACACAGGTGGAATCCACATGG
     GACCTGAAAATACCCCCTCGATACCGAAGTACCCTTTTCCGACGTCTTCTGTGTCCACCTTAGGTGTACC
771▶ L  D  F  Y  G  G  A  M  A  S  W  E  K  A  A  E  D  T  G  G  I  H  M

2381 AAGAGGCCCCAGAAACCTACATTCCCAGCAGGGCTGTATCTTTGTTCTTCAACTGGAAGCAGGAATTCAG
     TTCTCCGGGGTCTTTGGATGTAAGGGTCGTCCCGACATAGAAACAAGAAGTTGACCTTCGTCCTTAAGTC
794▶ E  E  A  P  E  T  Y  I  P  S  R  A  V  S  L  F  F  N  W  K  Q  E  F  R

2451 GACTCTGGAGGTCACACTCCGGGATTTCAGCAAGTTGAATAAGCAAGATATCAGATATCTGGGGAAAATA
     CTGAGACCTCCAGTGTGAGGCCCTAAAGTCGTTCAACTTATTCGTTCTATAGTCTATAGACCCCTTTTAT
817▶ T  L  E  V  T  L  R  D  F  S  K  L  N  K  Q  D  I  R  Y  L  G  K  I

2521 TTCAGCTCTGCCACAAGCCTCAGGCTGCAAATAAAGAGATGTGCTGGTGTGGCTGGAAGCCTCAGTTTGG
     AAGTCGAGACGGTGTTCGGAGTCCGACGTTTATTTCTCTACACGACCACACCGACCTTCGGAGTCAAACC
841▶ F  S  S  A  T  S  L  R  L  Q  I  K  R  C  A  G  V  A  G  S  L  S  L

2591 TCCTCAGCACCTGTAAGAACATTTATTCTCTCATGGTGGAAGCCAGTCCCCTCACCATAGAAGATGAGAG
     AGGAGTCGTGGACATTCTTGTAAATAAGAGAGTACCACCTTCGGTCAGGGGAGTGGTATCTTCTACTCTC
864▶ V  L  S  T  C  K  N  I  Y  S  L  M  V  E  A  S  P  L  T  I  E  D  E  R
```

FIG. 2C

```
2661 GCACATCACATCTGTAACAAACCTGAAAACCTTGAGTATTCATGACCTACAGAATCAACGGCTGCCGGGT
     CGTGTAGTGTAGACATTGTTTGGACTTTTGGAACTCATAAGTACTGGATGTCTTAGTTGCCGACGGCCCA
 887▶ H  I  T  S  V  T  N  L  K  T  L  S  I  H  D  L  Q  N  Q  R  L  P  G

2731 GGTCTGACTGACAGCTTGGGTAACTTGAAGAACCTTACAAAGCTCATAATGGATAACATAAAGATGAATG
     CCAGACTGACTGTCGAACCCATTGAACTTCTTGGAATGTTTCGAGTATTACCTATTGTATTTCTACTTAC
 911▶ G  L  T  D  S  L  G  N  L  K  N  L  T  K  L  I  M  D  N  I  K  M  N

2801 AAGAAGATGCTATAAAACTAGCTGAAGGCCTGAAAAACCTGAAGAAGATGTGTTTATTTCATTTGACCCA
     TTCTTCTACGATATTTTGATCGACTTCCGGACTTTTTGGACTTCTTCTACACAAATAAAGTAAACTGGGT
 934▶ E  E  D  A  I  K  L  A  E  G  L  K  N  L  K  K  M  C  L  F  H  L  T  H

2871 CTTGTCTGACATTGGAGAGGGAATGGATTACATAGTCAAGTCTCTGTCAAGTGAACCCTGTGACCTTGAA
     GAACAGACTGTAACCTCTCCCTTACCTAATGTATCAGTTCAGAGACAGTTCACTTGGGACACTGGAACTT
 957▶ L  S  D  I  G  E  G  M  D  Y  I  V  K  S  L  S  S  E  P  C  D  L  E

2941 GAAATTCAATTAGTCTCCTGCTGCTTGTCTGCAAATGCAGTGAAAATCCTAGCTCAGAATCTTCACAATT
     CTTTAAGTTAATCAGAGGACGACGAACAGACGTTTACGTCACTTTTAGGATCGAGTCTTAGAAGTGTTAA
 981▶ E  I  Q  L  V  S  C  C  L  S  A  N  A  V  K  I  L  A  Q  N  L  H  N

3011 TGGTCAAACTGAGCATTCTTGATTTATCAGAAAATTACCTGGAAAAAGATGGAAATGAAGCTCTTCATGA
     ACCAGTTTGACTCGTAAGAACTAAATAGTCTTTTAATGGACCTTTTTCTACCTTTACTTCGAGAAGTACT
1004▶ L  V  K  L  S  I  L  D  L  S  E  N  Y  L  E  K  D  G  N  E  A  L  H  E

3081 ACTGATCGACAGGATGAACGTGCTAGAACAGCTCACCGCACTGATGCTGCCCTGGGGCTGTGACGTGCAA
     TGACTAGCTGTCCTACTTGCACGATCTTGTCGAGTGGCGTGACTACGACGGGACCCCGACACTGCACGTT
1027▶ L  I  D  R  M  N  V  L  E  Q  L  T  A  L  M  L  P  W  G  C  D  V  Q

3151 GGCAGCCTGAGCAGCCTGTTGAAACATTTGGAGGAGGTCCCACAACTCGTCAAGCTTGGGTTGAAAAACT
     CCGTCGGACTCGTCGGACAACTTTGTAAACCTCCTCCAGGGTGTTGAGCAGTTCGAACCCAACTTTTTGA
1051▶ G  S  L  S  S  L  L  K  H  L  E  E  V  P  Q  L  V  K  L  G  L  K  N

3221 GGAGACTCACAGATACAGAGATTAGAATTTTAGGTGCATTTTTTGGAAAGAACCCTCTGAAAAACTTCCA
     CCTCTGAGTGTCTATGTCTCTAATCTTAAAATCCACGTAAAAAACCTTTCTTGGGAGACTTTTTGAAGGT
1074▶ W  R  L  T  D  T  E  I  R  I  L  G  A  F  F  G  K  N  P  L  K  N  F  Q

3291 GCAGTTGAATTTGGCGGGAAATCGTGTGAGCAGTGATGGATGGCTTGCCTTCATGGGTGTATTTGAGAAT
     CGTCAACTTAAACCGCCCTTTAGCACACTCGTCACTACCTACCGAACGGAAGTACCCACATAAACTCTTA
1097▶ Q  L  N  L  A  G  N  R  V  S  S  D  G  W  L  A  F  M  G  V  F  E  N

3361 CTTAAGCAATTAGTGTTTTTTGACTTTAGTACTAAAGAATTTCTACCTGATCCAGCATTAGTCAGAAAAC
     GAATTCGTTAATCACAAAAAACTGAAATCATGATTTCTTAAAGATGGACTAGGTCGTAATCAGTCTTTTG
1121▶ L  K  Q  L  V  F  F  D  F  S  T  K  E  F  L  P  D  P  A  L  V  R  K

3431 TTAGCCAAGTGTTATCCAAGTTAACTTTTCTGCAAGAAGCTAGGCTTGTTGGGTGGCAATTTGATGATGA
     AATCGGTTCACAATAGGTTCAATTGAAAAGACGTTCTTCGATCCGAACAACCCACCGTTAAACTACTACT
1144▶ L  S  Q  V  L  S  K  L  T  F  L  Q  E  A  R  L  V  G  W  Q  F  D  D  D

3501 TGATCTCAGTGTTATTACAGATGAGAAAGCTCAGATGATTTGCCCATGGGTTATAAAACTACTTCCTTAC
     ACTAGAGTCACAATAATGTCTACTCTTTCGAGTCTACTAAACGGGTACCCAATATTTTGATGAAGGAATG
1167▶ D  L  S  V  I  T  D  E  K  A  Q  M  I  C  P  W  V  I  K  L  L  P  Y
```

FIG. 2D

```
3571 ACAGTGGCAGCATCAGAACTGGAATTCAGATCTCTTGCCTCCTAG
     TGTCACCGTCGTAGTCTTGACCTTAAGTCTAGAGAACGGAGGATC
1191▶ T  V  A  A  S  E  L  E  F  R  S  L  A  S
```

FIG. 2E

```
CARD: domain 1 of 1, from 2 to 88: score 16.0, E = 0.0065
               *->aeddrrllrknrlellgeltlsglLdhLleknvLteeeeEkikaknt
                  + ++    ++ +  +g  +++++ d+L    nvL++ee+  i  +
       CARD12    2   --NFIKDNSRALIQRMGMTVIKQITDDLFVWNVLNREEVNIICCEKV 46 trrdkareLiDsvqkkGnqAfqiFlqaLretdqelladlllde<-*
               ++ d ar  i  +++kkG++ +++Fl +L+e ++ l +dl  +
       CARD12   47 EQ-DAARGIIHMILKKGSESCNLFLKSLKEWNYPLFQDLNGQS    88
```

FIG. 5A

```
LRR: domain 1 of 4, from 764 to 791: score 0.6, E = 8.2e+02
               *->nLeeLdLsnN.Lt.....slppglfsnLp<-*
                  nL++L ++n +  +++  +l +g ++nL+
       CARD12   764  NLTKLIMDNIkMNeedaiKLAEG-LKNLK   791
```
FIG. 5B

```
LRR: domain 2 of 4, from 821 to 848: score 0.3, E = 9.3e+02
               *->nLeeLdLsnN.Lt....slppglfsnLp<-*
                  Lee+ L ++ L+ +  ++     ++nL
       CARD12   821  DLEEIQLVSCcLSanavKILAQNLHNLV    848
```
FIG. 5C

```
LRR: domain 3 of 4, from 849 to 872: score 11.2, E = 23
               *->nLeeLdLsnN.LtslppglfsnLp<-*
                  +L  LdLs N L++  +++++ L
       CARD12   849  KLSILDLSENyLEKDGNEALHELI    872
```
FIG. 5D

```
LRR: domain 4 of 4, from 938 to 965: score 4.2, E = 2.5e+02
               *->nLeeLdLsnN.Lt.....slppglfsnLp<-*
                  n + L+L +N+ ++++    +  +f+nL+
       CARD12   938  NFQQLNLAGNrVSsdgwlAFMG-VFENLK    965
```
FIG. 5E

```
      E . L . . . . . . . L . S . . . . E G E . G . G K . . L L . . I A . L W . S G   Consensus #1
      E Q L V L N G V L G A L N S V C I V E G E A G S G K S V L L Q K I A F L W G S G   Majority
                    10              20              30              40
 1    E Q L T L N G L L Q A L Q S P C I I E G E S G K G K S T L L Q R I A M L W G S G   CARD12-C
 1    E P L V L P E V F G N L N S V M C V E G E A G S G K T V L L K K I A F L W A S G   NAIP-C . C . . L . . F . . V F . L . L S . . R . . . G L . . . . . C D Q L L . . . G . .   Consensus #1
      K C K A L T K F Q L V F F L S L S S T R A D G G L A S I L C D Q L L D I E G S V   Majority
                    50              60              70              80
 41   K C K A L T K F Q L V F F L R L S - - R A Q G G L F E T L C D Q L L D I P G T I   CARD12-C
 41   C C P L L N R F Q L V F Y L S L S S T R P D E G L A S I I C D Q L L E K E G S V   NAIP-C . . . . . . . . . . . . L . . . V L F L L D . Y . E . . . . . C . . . . . I . . L   Consensus #1
      T E Q T F R A I L L Q L K N Q V L F L L D G Y N E I K P Q N C S I P Q V I G A L   Majority
                    90              100             110             120
 79   R K Q T F M A M L L K L R Q R V L F L L D G Y N E F K P Q N C P E - - - I E A L   CARD12-C
 81   T E M C M R N I I Q Q L K N Q V L F L L D D Y K E I - - - - C S I P Q V I G K L   NAIP-C I . . N H . . . . . . . . . . T . . . R . I R . . . . . . . . E . . . . . . . .   Consensus #1
      I Q E N H L S K T C V L V A V T T E R A R D I R Q F G A L I A E V G A F T E D S   Majority
                    130             140             150             160
 116  I K E N H R F K N M V I V T T T T E C L R H I R Q F G A L T A E V G D M T E D S   CARD12-C
 117  I Q K N H L S R T C L L I A V R T N R A R D I R R Y L E T I L E I Q A F P F Y N   NAIP-C . . . . . R . . . . . . . . . . . . . . . . . . K . . . L . . . . K T P L F V .   Consensus #1
      A V A L L R E V L I K E L A E L R G L L V Q I G K S Q S L Q N L Q K T P L F V A   Majority
                    170             180             190             200
 156  A Q A L I R E V L I K E L A E - - G L L L Q I Q K S R C L R N L M K T P L F V V   CARD12-C
 157  T V C I L R K L F S H N M T R L R K F M V Y F G K N Q S L Q K I Q K T P L F V A   NAIP-C . . C A . . . . . . . . F . . . . . . . . . . F . . . . . . L . . . N K . . . . . .   Consensus #1
      A I C A I Q W G E S E F D S S F T D V A V F K S F Y D L L I L K N K H K H K G V   Majority
                    210             220             230             240
 194  I T C A I Q M G E S E F H S H - T Q T T L F H T F Y D L L I Q K N K H K H K G V   CARD12-C
 197  A I C A - H W F Q Y P F D P S F D D V A V F K S Y M E R L S L R N K - - - - - -   NAIP-C A . . . . . . . . . . . C G . L A L . G . F S . . F . F . . . D . . . . . V . E   Consensus #1
      A A A D I L K A T V S S C G D L A L E G V F S H K F D F E L D D V A E A G V D E   Majority
                    250             260             270             280
 233  A A S D F I R S - L D H C G D L A L E G V F S H K F D F E L Q D V S - - S V N E   CARD12-C
 230  A T A E I L K A T V S S C G E L A L K G F F S C C F E F N D D L A E A G V D E   NAIP-C D . . L T . . L . . K . T A Q R . . P . Y . F . . . . F Q E . . . A G . R L . . L   Consensus #1
      D V L L T T G L L S K F T A Q R L K P K Y K F L S K A F Q E F L A G R R L I S L   Majority
                    290             300             310             320
 270  D V L L T T G L L C K Y T A Q R F K P K Y K F F H K S F Q E Y T A G R R L S S L   CARD12-C
 270  D E D L T M C L M S K F T A Q R L R P F Y R F L S P A F Q E F L A G M R L I E L   NAIP-C
```

```
         . . I . . . . . . . . . . . K . . . . . . . . . . . . C . . . . . . L S . . . .    Consensus #1
         E L I R D A L E L S E A S A I K L A E G L K N L K K M C L I S L L E L S A A G E    Majority
                       650             660             670             680

618  K L I M D N I K M N E E D A I K L A E G L K N L K K M C L F H L T H L S D I G E   CARD12-C
592  E S I R P A L E L S K A S V T K - - - - - - - - - - - C S I S K L E L S A A E Q   NAIP-C

. . . . . . . . S L . S . . . . L E . . . . . . . . . . . . . . . . . Q . . . N    Consensus #1
         G L L L I V K S L S S E P C D L E E I Q L V S C C L V A G A V Q I L A Q I L H N    Majority
                       690             700             710             720

658  G M D Y I V K S L S S E P C D L E E I Q L V S C C L S A N A V K I L A Q N L H N   CARD12-C
621  E L L L T L P S L E S - - - - L E - - - - - - - - - V S G T I Q S Q D Q I F P N   NAIP-C

L . K . . . L . L . E . . . . . . G N . . . . . . I . . . . . . . . . . . L .      Consensus #1
         L V K L S I L D L S E L S V D L D G N I A V H S V I P D E F N V L E Q L T A L L    Majority
                       730             740             750             760

698  L V K L S I L D L S E N Y L E K D G N E A L H E L I - D R M N V L E Q L T A L M   CARD12-C
648  L D K F - - L C L K E L S V D L E G N I N V F S V I P E E F P N F H H M E K L L   NAIP-C

. . . . . . . . . . . . S . L . . . L . . . . . . L . . L . L . . . . . . D . E . .    Consensus #1
         L Q I G A D V D G S L S S L V A S L E E V I S L V I L G L E G Q Q L T D T E I S    Majority
                       770             780             790             800

737  L P W G C D V Q G S L S S L L K H L E E V P Q L V K L G L K N W R L T D T E I R   CARD12-C
686  I Q I S A E Y D P - - S K L V A S L P N F I S L K I L N L E G Q Q F P D E T S     NAIP-C

. . . A . . . . . . L . N . . . L . L . . . . . . . . . . . . G . . . . . K        Consensus #1
         I L G A F I G L G S L S N L E E L I L A G G D V S S D G W L A F M G V F E V A K    Majority
                       810             820             830             840

777  I L G A F F G K N P L K N F Q Q L N L A G N R V S S D G W L A F M G V F E N L K   CARD12-C
724  E K F A Y I - L G S L S N L E E L I L P T G D - - - - - - - - - G I Y R V A K     NAIP-C

. . . . . . . . . . . . . . . . . L . . L . . L . F . . . . . . . .                 Consensus #1
         L L V F F D F S T K E F L P D P A L V Q Q L S Q V L S V L S F L Q T A R L V G W    Majority
                       850             860             870             880

817  Q L V F F D F S T K E F L P D P A L V R K L S Q V L S K L T F L Q E A R L V G W   CARD12-C
753  L I I - - - - - - - - - - - - - Q Q C Q Q L - H C L R V L S E F K T - - - - - -   NAIP-C

. . . D D . . . . . I . . . . . . . . . .                                           Consensus #1
         Q L D D D S V V V I T G A F K L V T G                                                Majority
                       890

857  Q F D D D L S V I T G A F K L V T A                                                      CARD12-C
773  - L N D D S V V E I - - - - - - - - G                                                    NAIP-C
```

Consensus 'Consensus #1': When all match the residue of CARD12-C show the residue of CARD12-C, otherwise show '.'.

Decoration 'Decoration #1': Box residues that match the consensus named 'Consensus #1' exactly.

FIG. 6C

SEQUENCE LISTING

```
<160> NUMBER OF SEQ ID NOS: 12

<210> SEQ ID NO 1
<211> LENGTH: 3133
<212> TYPE: DNA
<213> ORGANISM: Homo sapiens
<220> FEATURE:
<221> NAME/KEY: CDS
<222> LOCATION: (36)...(3107)

<400> SEQUENCE: 1
cgctctagcc cggtgggaag ctttcatcca gaaca atg aat ttc ata aag gac         53
                                      Met Asn Phe Ile Lys Asp
                                        1               5 aat agc cga gcc ctt att caa aga atg gga atg act gtt ata aag caa      101
Asn Ser Arg Ala Leu Ile Gln Arg Met Gly Met Thr Val Ile Lys Gln
             10                  15                  20 atc aca gat gac cta ttt gta tgg aat gtt ctg aat cgc gaa gaa gta      149
Ile Thr Asp Asp Leu Phe Val Trp Asn Val Leu Asn Arg Glu Glu Val
         25                  30                  35 aac atc att tgc tgc gag aag gtg gag cag gat gct gct aga ggg atc      197
Asn Ile Ile Cys Cys Glu Lys Val Glu Gln Asp Ala Ala Arg Gly Ile
     40                  45                  50 att cac atg att ttg aaa aag ggt tca gag tcc tgt aac ctc ttt ctt      245
Ile His Met Ile Leu Lys Lys Gly Ser Glu Ser Cys Asn Leu Phe Leu
 55                  60                  65                  70 aaa tcc ctt aag gag tgg aac tat cct cta ttt cag gac ttg aat gga      293
Lys Ser Leu Lys Glu Trp Asn Tyr Pro Leu Phe Gln Asp Leu Asn Gly
                 75                  80                  85 caa agt ctt ttt cat cag aca tca gaa gga gac ttg gac gat ttg gct      341
Gln Ser Leu Phe His Gln Thr Ser Glu Gly Asp Leu Asp Asp Leu Ala
             90                  95                 100 cag gat tta aag gac ttg tac cat acc cca tct ttt ctg aac ttt tat      389
Gln Asp Leu Lys Asp Leu Tyr His Thr Pro Ser Phe Leu Asn Phe Tyr
        105                 110                 115 ccc ctt ggt gaa gat att gac att att ttt aac ttg aaa agc acc ttc      437
Pro Leu Gly Glu Asp Ile Asp Ile Ile Phe Asn Leu Lys Ser Thr Phe
    120                 125                 130 aca gaa cct gtc ctg tgg agg aag gac caa cac cat cac cgc gtg gag      485
Thr Glu Pro Val Leu Trp Arg Lys Asp Gln His His His Arg Val Glu
135                 140                 145                 150 cag ctg acc ctg aat ggc ctc ctg cag gct ctt cag agc ccc tgc atc      533
Gln Leu Thr Leu Asn Gly Leu Leu Gln Ala Leu Gln Ser Pro Cys Ile
                155                 160                 165 att gaa ggg gaa tct ggc aaa ggc aag tcc act ctg ctg cag cgc att      581
Ile Glu Gly Glu Ser Gly Lys Gly Lys Ser Thr Leu Leu Gln Arg Ile
            170                 175                 180 gcc atg ctc tgg ggc tcc gga aag tgc aag gct ctg acc aag ttc aaa      629
```

```
                    Ala Met Leu Trp Gly Ser Gly Lys Cys Lys Ala Leu Thr Lys Phe Lys
                            185                 190                 195 ttc gtc ttc ttc ctc cgt ctc agc agg gcc cag ggt gga ctt ttt gaa                677
Phe Val Phe Phe Leu Arg Leu Ser Arg Ala Gln Gly Gly Leu Phe Glu
    200                 205                 210 acc ctc tgt gat caa ctc ctg gat ata cct ggc aca atc agg aag cag                725
Thr Leu Cys Asp Gln Leu Leu Asp Ile Pro Gly Thr Ile Arg Lys Gln
215                 220                 225                 230 aca ttc atg gcc atg ctg ctg aag ctg cgg cag agg gtt ctt ttc ctt                773
Thr Phe Met Ala Met Leu Leu Lys Leu Arg Gln Arg Val Leu Phe Leu
                235                 240                 245 ctt gat ggc tac aat gaa ttc aag ccc cag aac tgc cca gaa atc gaa                821
Leu Asp Gly Tyr Asn Glu Phe Lys Pro Gln Asn Cys Pro Glu Ile Glu
            250                 255                 260 gcc ctg ata aag gaa aac cac cgc ttc aag aac atg gtc atc gtc acc                869
Ala Leu Ile Lys Glu Asn His Arg Phe Lys Asn Met Val Ile Val Thr
        265                 270                 275 act acc act gag tgc ctg agg cac ata cgg cag ttt ggt gcc ctg act                917
Thr Thr Thr Glu Cys Leu Arg His Ile Arg Gln Phe Gly Ala Leu Thr
    280                 285                 290 gct gag gtg ggg gat atg aca gaa gac agc gcc cag gct ctc atc cga                965
Ala Glu Val Gly Asp Met Thr Glu Asp Ser Ala Gln Ala Leu Ile Arg
295                 300                 305                 310 gaa gtg ctg atc aag gag ctt gct gaa ggc ttg ttg ctc caa att cag               1013
Glu Val Leu Ile Lys Glu Leu Ala Glu Gly Leu Leu Leu Gln Ile Gln
                315                 320                 325 aaa tcc agg tgc ttg agg aat ctc atg aag acc cct ctc ttt gtg gtc               1061
Lys Ser Arg Cys Leu Arg Asn Leu Met Lys Thr Pro Leu Phe Val Val
            330                 335                 340 atc act tgt gca atc cag atg ggt gaa agt gag ttc cac tct cac aca               1109
Ile Thr Cys Ala Ile Gln Met Gly Glu Ser Glu Phe His Ser His Thr
        345                 350                 355 caa aca acg ctg ttc cat acc ttc tat gat ctg ttg ata cag aaa aac               1157
Gln Thr Thr Leu Phe His Thr Phe Tyr Asp Leu Leu Ile Gln Lys Asn
    360                 365                 370 aaa cac aaa cat aaa ggt gtg gct gca agt gac ttc att cgg agc ctg               1205
Lys His Lys His Lys Gly Val Ala Ala Ser Asp Phe Ile Arg Ser Leu
375                 380                 385                 390 gac cac tgt gga gac cta gct ctg gag ggt gtg ttc tcc cac aag ttt               1253
Asp His Cys Gly Asp Leu Ala Leu Glu Gly Val Phe Ser His Lys Phe
                395                 400                 405 gat ttc gaa ctg cag gat gtg tcc agc gtg aat gag gat gtc ctg ctg               1301
Asp Phe Glu Leu Gln Asp Val Ser Ser Val Asn Glu Asp Val Leu Leu
            410                 415                 420 aca act ggg ctc ctc tgt aaa tat aca gct caa agg ttc aag cca aag               1349
Thr Thr Gly Leu Leu Cys Lys Tyr Thr Ala Gln Arg Phe Lys Pro Lys
        425                 430                 435 tat aaa ttc ttt cac aag tca ttc cag gag tac aca gca gga cga aga               1397
Tyr Lys Phe Phe His Lys Ser Phe Gln Glu Tyr Thr Ala Gly Arg Arg
    440                 445                 450 ctc agc agt tta ttg acg tct cat gag cca gag gag gtg acc aag ggg               1445
Leu Ser Ser Leu Leu Thr Ser His Glu Pro Glu Glu Val Thr Lys Gly
455                 460                 465                 470 aat ggt tac ttg cag aaa atg gtt tcc att tcg gac att aca tcc act               1493
Asn Gly Tyr Leu Gln Lys Met Val Ser Ile Ser Asp Ile Thr Ser Thr
                475                 480                 485 tat agc agc ctg ctc cgg tac acc tgt ggg tca tct gtg gaa gcc acc               1541
Tyr Ser Ser Leu Leu Arg Tyr Thr Cys Gly Ser Ser Val Glu Ala Thr
            490                 495                 500
```

-continued

```
agg gct gtt atg aag cac ctc gca gca gtg tat caa cac ggc tgc ctt      1589
Arg Ala Val Met Lys His Leu Ala Ala Val Tyr Gln His Gly Cys Leu
        505                 510                 515 ctc gga ctt tcc atc gcc aag agg cct ctc tgg aga cag gaa tct ttg      1637
Leu Gly Leu Ser Ile Ala Lys Arg Pro Leu Trp Arg Gln Glu Ser Leu
520                 525                 530 caa agt gtg aaa aac acc act gag caa gaa att ctg aaa gcc ata aac      1685
Gln Ser Val Lys Asn Thr Thr Glu Gln Glu Ile Leu Lys Ala Ile Asn
535                 540                 545                 550 atc aat tcc ttt gta gag tgt ggc atc cat tta tat caa gag agt aca      1733
Ile Asn Ser Phe Val Glu Cys Gly Ile His Leu Tyr Gln Glu Ser Thr
                555                 560                 565 tcc aaa tca gcc ctg agc caa gaa ttt gaa gct ttc ttt caa ggt aaa      1781
Ser Lys Ser Ala Leu Ser Gln Glu Phe Glu Ala Phe Phe Gln Gly Lys
            570                 575                 580 agc tta tat atc aac tca ggg aac atc ccc gat tac tta ttt gac ttc      1829
Ser Leu Tyr Ile Asn Ser Gly Asn Ile Pro Asp Tyr Leu Phe Asp Phe
        585                 590                 595 ttt gaa cat ttg ccc aat tgt gca agt gct ctg gac ttc att aaa ctg      1877
Phe Glu His Leu Pro Asn Cys Ala Ser Ala Leu Asp Phe Ile Lys Leu
600                 605                 610 gac ttt tat ggg gga gct atg gct tca tgg gaa aag gct gca gaa gac      1925
Asp Phe Tyr Gly Gly Ala Met Ala Ser Trp Glu Lys Ala Ala Glu Asp
615                 620                 625                 630 aca ggt gga atc cac atg gaa gag gcc cca gaa acc tac att ccc agc      1973
Thr Gly Gly Ile His Met Glu Glu Ala Pro Glu Thr Tyr Ile Pro Ser
                635                 640                 645 agg gct gta tct ttg ttc ttc aac tgg aag cag gaa ttc agg act ctg      2021
Arg Ala Val Ser Leu Phe Phe Asn Trp Lys Gln Glu Phe Arg Thr Leu
            650                 655                 660 gag gtc aca ctc cgg gat ttc agc aag ttg aat aag caa gat atc aca      2069
Glu Val Thr Leu Arg Asp Phe Ser Lys Leu Asn Lys Gln Asp Ile Thr
        665                 670                 675 tat ctg ggg aaa ata ttc agc tct gcc aca agc ctc agg ctg caa ata      2117
Tyr Leu Gly Lys Ile Phe Ser Ser Ala Thr Ser Leu Arg Leu Gln Ile
680                 685                 690 aag aga tgt gct ggt gtg gct gga agc ctc agt ttg gtc ctc agc acc      2165
Lys Arg Cys Ala Gly Val Ala Gly Ser Leu Ser Leu Val Leu Ser Thr
695                 700                 705                 710 tgt aag aac att tat tct ctc atg gtg gaa gcc agt ccc ctc acc ata      2213
Cys Lys Asn Ile Tyr Ser Leu Met Val Glu Ala Ser Pro Leu Thr Ile
                715                 720                 725 gaa gat gag agg cac atc aca tct gta aca aac ctg aaa acc ttg agt      2261
Glu Asp Glu Arg His Ile Thr Ser Val Thr Asn Leu Lys Thr Leu Ser
            730                 735                 740 att cat gac cta cag aat caa cgg ctg ccg ggt ggt ctg act gac agc      2309
Ile His Asp Leu Gln Asn Gln Arg Leu Pro Gly Gly Leu Thr Asp Ser
        745                 750                 755 ttg ggt aac ttg aag aac ctt aca aag ctc ata atg gat aac ata aag      2357
Leu Gly Asn Leu Lys Asn Leu Thr Lys Leu Ile Met Asp Asn Ile Lys
760                 765                 770 atg aat gaa gaa gat gct ata aaa cta gct gaa ggc ctg aaa aac ctg      2405
Met Asn Glu Glu Asp Ala Ile Lys Leu Ala Glu Gly Leu Lys Asn Leu
775                 780                 785                 790 aag aag atg tgt tta ttt cat ttg acc cac ttg tct gac att gga gag      2453
Lys Lys Met Cys Leu Phe His Leu Thr His Leu Ser Asp Ile Gly Glu
                795                 800                 805 gga atg gat tac ata gtc aag tct ctg tca agt gaa ccc tgt gac ctt      2501
Gly Met Asp Tyr Ile Val Lys Ser Leu Ser Ser Glu Pro Cys Asp Leu
            810                 815                 820
```

```
gaa gaa att caa tta gtc tcc tgc tgc ttg tct gca aat gca gtg aaa    2549
Glu Glu Ile Gln Leu Val Ser Cys Cys Leu Ser Ala Asn Ala Val Lys
            825                 830                 835 atc cta gct cag aat ctt cac aat ttg gtc aaa ctg agc att ctt gat    2597
Ile Leu Ala Gln Asn Leu His Asn Leu Val Lys Leu Ser Ile Leu Asp
840                 845                 850 tta tca gaa aat tac ctg gaa aaa gat gga aat gaa gct ctt cat gaa    2645
Leu Ser Glu Asn Tyr Leu Glu Lys Asp Gly Asn Glu Ala Leu His Glu
    855                 860                 865                 870 ctg atc gac agg atg aac gtg cta gaa cag ctc acc gca ctg atg ctg    2693
Leu Ile Asp Arg Met Asn Val Leu Glu Gln Leu Thr Ala Leu Met Leu
                875                 880                 885 ccc tgg ggc tgt gac gtg caa ggc agc ctg agc agc ctg ttg aaa cat    2741
Pro Trp Gly Cys Asp Val Gln Gly Ser Leu Ser Ser Leu Leu Lys His
            890                 895                 900 ttg gag gag gtc cca caa ctc gtc aag ctt ggg ttg aaa aac tgg aga    2789
Leu Glu Glu Val Pro Gln Leu Val Lys Leu Gly Leu Lys Asn Trp Arg
        905                 910                 915 ctc aca gat aca gag att aga att tta ggt gca ttt ttt gga aag aac    2837
Leu Thr Asp Thr Glu Ile Arg Ile Leu Gly Ala Phe Phe Gly Lys Asn
    920                 925                 930 cct ctg aaa aac ttc cag cag ttg aat ttg gcg gga aat cgt gtg agc    2885
Pro Leu Lys Asn Phe Gln Gln Leu Asn Leu Ala Gly Asn Arg Val Ser
935                 940                 945                 950 agt gat gga tgg ctt gcc ttc atg ggt gta ttt gag aat ctt aag caa    2933
Ser Asp Gly Trp Leu Ala Phe Met Gly Val Phe Glu Asn Leu Lys Gln
                955                 960                 965 tta gtg ttt ttt gac ttt agt act aaa gaa ttt cta cct gat cca gca    2981
Leu Val Phe Phe Asp Phe Ser Thr Lys Glu Phe Leu Pro Asp Pro Ala
            970                 975                 980 tta gtc aga aaa ctt agc caa gtg tta tcc aag tta act ttt ctg caa    3029
Leu Val Arg Lys Leu Ser Gln Val Leu Ser Lys Leu Thr Phe Leu Gln
        985                 990                 995 gaa gct agg ctt gtt ggg tgg caa ttt gat gat gat gat ctc agt gtt    3077
Glu Ala Arg Leu Val Gly Trp Gln Phe Asp Asp Asp Asp Leu Ser Val
    1000                1005                1010 att aca ggt gct ttt aaa cta gta act gct taaataaagt gtactcgaag     3127
Ile Thr Gly Ala Phe Lys Leu Val Thr Ala
1015                1020 ccagta                                                            3133

<210> SEQ ID NO 2
<211> LENGTH: 1024
<212> TYPE: PRT
<213> ORGANISM: Homo sapiens

<400> SEQUENCE: 2

Met Asn Phe Ile Lys Asp Asn Ser Arg Ala Leu Ile Gln Arg Met Gly
1               5                   10                  15

Met Thr Val Ile Lys Gln Ile Thr Asp Asp Leu Phe Trp Asn Val
            20                  25                  30

Leu Asn Arg Glu Glu Val Asn Ile Cys Cys Glu Lys Val Glu Gln
        35                  40                  45

Asp Ala Ala Arg Gly Ile Ile His Met Ile Leu Lys Lys Gly Ser Glu
    50                  55                  60

Ser Cys Asn Leu Phe Leu Lys Ser Leu Lys Glu Trp Asn Tyr Pro Leu
65                  70                  75                  80

Phe Gln Asp Leu Asn Gly Gln Ser Leu Phe His Gln Thr Ser Glu Gly
```

```
                    85                  90                  95
Asp Leu Asp Asp Leu Ala Gln Asp Leu Lys Asp Leu Tyr His Thr Pro
                100                 105                 110
Ser Phe Leu Asn Phe Tyr Pro Leu Gly Glu Asp Ile Asp Ile Ile Phe
            115                 120                 125
Asn Leu Lys Ser Thr Phe Thr Glu Pro Val Leu Trp Arg Lys Asp Gln
        130                 135                 140
His His His Arg Val Glu Gln Leu Thr Leu Asn Gly Leu Leu Gln Ala
145                 150                 155                 160
Leu Gln Ser Pro Cys Ile Ile Glu Gly Glu Ser Gly Lys Gly Lys Ser
                165                 170                 175
Thr Leu Leu Gln Arg Ile Ala Met Leu Trp Gly Ser Gly Lys Cys Lys
                180                 185                 190
Ala Leu Thr Lys Phe Lys Phe Val Phe Phe Leu Arg Leu Ser Arg Ala
                195                 200                 205
Gln Gly Gly Leu Phe Glu Thr Leu Cys Asp Gln Leu Leu Asp Ile Pro
            210                 215                 220
Gly Thr Ile Arg Lys Gln Thr Phe Met Ala Met Leu Leu Lys Leu Arg
225                 230                 235                 240
Gln Arg Val Leu Phe Leu Leu Asp Gly Tyr Asn Glu Phe Lys Pro Gln
                245                 250                 255
Asn Cys Pro Glu Ile Glu Ala Leu Ile Lys Glu Asn His Arg Phe Lys
                260                 265                 270
Asn Met Val Ile Val Thr Thr Thr Thr Glu Cys Leu Arg His Ile Arg
                275                 280                 285
Gln Phe Gly Ala Leu Thr Ala Glu Val Gly Asp Met Thr Glu Asp Ser
        290                 295                 300
Ala Gln Ala Leu Ile Arg Glu Val Leu Ile Lys Glu Leu Ala Glu Gly
305                 310                 315                 320
Leu Leu Leu Gln Ile Gln Lys Ser Arg Cys Leu Arg Asn Leu Met Lys
                325                 330                 335
Thr Pro Leu Phe Val Val Ile Thr Cys Ala Ile Gln Met Gly Glu Ser
                340                 345                 350
Glu Phe His Ser His Thr Gln Thr Thr Leu Phe His Thr Phe Tyr Asp
            355                 360                 365
Leu Leu Ile Gln Lys Asn Lys His Lys His Lys Gly Val Ala Ala Ser
        370                 375                 380
Asp Phe Ile Arg Ser Leu Asp His Cys Gly Asp Leu Ala Leu Glu Gly
385                 390                 395                 400
Val Phe Ser His Lys Phe Asp Phe Glu Leu Gln Asp Val Ser Ser Val
                405                 410                 415
Asn Glu Asp Val Leu Leu Thr Thr Gly Leu Leu Cys Lys Tyr Thr Ala
                420                 425                 430
Gln Arg Phe Lys Pro Lys Tyr Lys Phe Phe His Lys Ser Phe Gln Glu
            435                 440                 445
Tyr Thr Ala Gly Arg Arg Leu Ser Ser Leu Leu Thr Ser His Glu Pro
        450                 455                 460
Glu Glu Val Thr Lys Gly Asn Gly Tyr Leu Gln Lys Met Val Ser Ile
465                 470                 475                 480
Ser Asp Ile Thr Ser Thr Tyr Ser Ser Leu Leu Arg Tyr Thr Cys Gly
                485                 490                 495
Ser Ser Val Glu Ala Thr Arg Ala Val Met Lys His Leu Ala Ala Val
                500                 505                 510
```

-continued

```
Tyr Gln His Gly Cys Leu Leu Gly Leu Ser Ile Ala Lys Arg Pro Leu
            515                 520                 525
Trp Arg Gln Glu Ser Leu Gln Ser Val Lys Asn Thr Thr Glu Gln Glu
        530                 535                 540
Ile Leu Lys Ala Ile Asn Ile Asn Ser Phe Val Glu Cys Gly Ile His
545                 550                 555                 560
Leu Tyr Gln Glu Ser Thr Ser Lys Ser Ala Leu Ser Gln Glu Phe Glu
                565                 570                 575
Ala Phe Phe Gln Gly Lys Ser Leu Tyr Ile Asn Ser Gly Asn Ile Pro
            580                 585                 590
Asp Tyr Leu Phe Asp Phe Phe Glu His Leu Pro Asn Cys Ala Ser Ala
        595                 600                 605
Leu Asp Phe Ile Lys Leu Asp Phe Tyr Gly Gly Ala Met Ala Ser Trp
    610                 615                 620
Glu Lys Ala Ala Glu Asp Thr Gly Gly Ile His Met Glu Glu Ala Pro
625                 630                 635                 640
Glu Thr Tyr Ile Pro Ser Arg Ala Val Ser Leu Phe Phe Asn Trp Lys
                645                 650                 655
Gln Glu Phe Arg Thr Leu Glu Val Thr Leu Arg Asp Phe Ser Lys Leu
            660                 665                 670
Asn Lys Gln Asp Ile Thr Tyr Leu Gly Lys Ile Phe Ser Ser Ala Thr
        675                 680                 685
Ser Leu Arg Leu Gln Ile Lys Arg Cys Ala Gly Val Ala Gly Ser Leu
    690                 695                 700
Ser Leu Val Leu Ser Thr Cys Lys Asn Ile Tyr Ser Leu Met Val Glu
705                 710                 715                 720
Ala Ser Pro Leu Thr Ile Glu Asp Glu Arg His Ile Thr Ser Val Thr
                725                 730                 735
Asn Leu Lys Thr Leu Ser Ile His Asp Leu Gln Asn Gln Arg Leu Pro
            740                 745                 750
Gly Gly Leu Thr Asp Ser Leu Gly Asn Leu Lys Asn Leu Thr Lys Leu
        755                 760                 765
Ile Met Asp Asn Ile Lys Met Asn Glu Glu Asp Ala Ile Lys Leu Ala
    770                 775                 780
Glu Gly Leu Lys Asn Leu Lys Lys Met Cys Leu Phe His Leu Thr His
785                 790                 795                 800
Leu Ser Asp Ile Gly Glu Gly Met Asp Tyr Ile Val Lys Ser Leu Ser
                805                 810                 815
Ser Glu Pro Cys Asp Leu Glu Glu Ile Gln Leu Val Ser Cys Cys Leu
            820                 825                 830
Ser Ala Asn Ala Val Lys Ile Leu Ala Gln Asn Leu His Asn Leu Val
        835                 840                 845
Lys Leu Ser Ile Leu Asp Leu Ser Glu Asn Tyr Leu Glu Lys Asp Gly
    850                 855                 860
Asn Glu Ala Leu His Glu Leu Ile Asp Arg Met Asn Val Leu Glu Gln
865                 870                 875                 880
Leu Thr Ala Leu Met Leu Pro Trp Gly Cys Asp Val Gln Gly Ser Leu
                885                 890                 895
Ser Ser Leu Leu Lys His Leu Glu Glu Val Pro Gln Leu Val Lys Leu
            900                 905                 910
Gly Leu Lys Asn Trp Arg Leu Thr Asp Thr Glu Ile Arg Ile Leu Gly
        915                 920                 925
```

-continued

| Ala | Phe | Phe | Gly | Lys | Asn | Pro | Leu | Lys | Asn | Phe | Gln | Gln | Leu | Asn | Leu |
| --- | --- | --- | --- | --- | --- | --- | --- | --- | --- | --- | --- | --- | --- | --- | --- |
|  | 930 |  |  |  | 935 |  |  |  | 940 |  |  |  |  |  |  |

| Ala | Gly | Asn | Arg | Val | Ser | Ser | Asp | Gly | Trp | Leu | Ala | Phe | Met | Gly | Val |
| --- | --- | --- | --- | --- | --- | --- | --- | --- | --- | --- | --- | --- | --- | --- | --- |
| 945 |  |  |  |  | 950 |  |  |  |  | 955 |  |  |  |  | 960 |

| Phe | Glu | Asn | Leu | Lys | Gln | Leu | Val | Phe | Phe | Asp | Phe | Ser | Thr | Lys | Glu |
| --- | --- | --- | --- | --- | --- | --- | --- | --- | --- | --- | --- | --- | --- | --- | --- |
|  |  |  |  | 965 |  |  |  |  | 970 |  |  |  |  | 975 |  |

| Phe | Leu | Pro | Asp | Pro | Ala | Leu | Val | Arg | Lys | Leu | Ser | Gln | Val | Leu | Ser |
| --- | --- | --- | --- | --- | --- | --- | --- | --- | --- | --- | --- | --- | --- | --- | --- |
|  |  |  | 980 |  |  |  |  | 985 |  |  |  |  | 990 |  |  |

| Lys | Leu | Thr | Phe | Leu | Gln | Glu | Ala | Arg | Leu | Val | Gly | Trp | Gln | Phe | Asp |
| --- | --- | --- | --- | --- | --- | --- | --- | --- | --- | --- | --- | --- | --- | --- | --- |
|  |  | 995 |  |  |  |  | 1000 |  |  |  |  | 1005 |  |  |  |

| Asp | Asp | Asp | Leu | Ser | Val | Ile | Thr | Gly | Ala | Phe | Lys | Leu | Val | Thr | Ala |
| --- | --- | --- | --- | --- | --- | --- | --- | --- | --- | --- | --- | --- | --- | --- | --- |
|  |  | 1010 |  |  |  |  | 1015 |  |  |  |  | 1020 |  |  |  |

<210> SEQ ID NO 3
<211> LENGTH: 3072
<212> TYPE: DNA
<213> ORGANISM: Homo sapiens

<400> SEQUENCE: 3

| atgaatttca taaaggacaa tagccgagcc cttattcaaa gaatgggaat gactgttata | 60 |
| --- | --- |
| aagcaaatca cagatgacct atttgtatgg aatgttctga atcgcgaaga agtaaacatc | 120 |
| atttgctgcg agaaggtgga gcaggatgct gctagaggga tcattcacat gattttgaaa | 180 |
| aagggttcag agtcctgtaa cctctttctt aaatccctta aggagtggaa ctatcctcta | 240 |
| tttcaggact tgaatggaca agtcttttt catcagacat cagaaggaga cttggacgat | 300 |
| ttggctcagg atttaaagga cttgtaccat accccatctt ttctgaactt ttatcccctt | 360 |
| ggtgaagata ttgacattat ttttaacttg aaaagcacct tcacagaacc tgtcctgtgg | 420 |
| aggaaggacc aacaccatca ccgcgtggag cagctgaccc tgaatggcct cctgcaggct | 480 |
| cttcagagcc cctgcatcat tgaaggggaa tctggcaaag gcaagtccac tctgctgcag | 540 |
| cgcattgcca tgctctgggg ctccggaaag tgcaaggctc tgaccaagtt caaattcgtc | 600 |
| ttcttcctcc gtctcagcag ggcccagggt ggactttttg aaaccctctg tgatcaactc | 660 |
| ctggatatac ctggcacaat caggaagcag acattcatgg ccatgctgct gaagctgcgg | 720 |
| cagagggttc ttttccttct tgatggctac aatgaattca gccccagaa ctgcccagaa | 780 |
| atcgaagccc tgataaagga aaaccaccgc ttcaagaaca tggtcatcgt caccactacc | 840 |
| actgagtgcc tgaggcacat acggcagttt ggtgccctga ctgctgaggt gggggatatg | 900 |
| acagaagaca gcgcccaggc tctcatccga gaagtgctga tcaaggagct tgctgaaggc | 960 |
| ttgttgctcc aaattcagaa atccaggtgc ttgaggaatc tcatgaagac ccctctcttt | 1020 |
| gtggtcatca cttgtgcaat ccagatgggt gaaagtgagt ccactctca cacacaaaca | 1080 |
| acgctgttcc ataccttcta tgatctgttg atacagaaaa acaaacacaa acataaaggt | 1140 |
| gtggctgcaa gtgacttcat tcggagcctg accactgtg agacctagc tctggagggt | 1200 |
| gtgttctccc acaagtttga tttcgaactg caggatgtgt ccagcgtgaa tgaggatgtc | 1260 |
| ctgctgacaa ctgggctcct ctgtaaatat acagctcaaa ggttcaagcc aaagtataaa | 1320 |
| ttctttcaca agtcattcca ggagtacaca gcaggacgaa gactcagcag tttattgacg | 1380 |
| tctcatgagc cagaggaggt gaccaagggg aatggttact gcagaaaat ggtttccatt | 1440 |
| tcggacatta catccactta tagcagcctg ctccggtaca cctgtgggtc atctgtggaa | 1500 |
| gccaccaggg ctgttatgaa gcacctcgca gcagtgtatc aacacggctg ccttctcgga | 1560 |
| ctttccatcg ccaagaggcc tctctggaga caggaatctt tgcaaagtgt gaaaaacacc | 1620 |

-continued

```
actgagcaag aaattctgaa agccataaac atcaattcct tgtagagtg tggcatccat    1680 ttatatcaag agagtacatc caaatcagcc ctgagccaag aatttgaagc tttctttcaa    1740
ggtaaaagct tatatatcaa ctcagggaac atccccgatt acttatttga cttctttgaa    1800
catttgccca attgtgcaag tgctctggac ttcattaaac tggactttta tggggagct    1860 atggcttcat gggaaaaggc tgcagaagac acaggtggaa tccacatgga agaggcccca    1920
gaaacctaca ttcccagcag ggctgtatct tgttcttca actggaagca ggaattcagg     1980
actctggagg tcacactccg ggatttcagc aagttgaata agcaagatat cacatatctg    2040
gggaaaatat tcagctctgc cacaagcctc aggctgcaaa taaagagatg tgctggtgtg    2100
gctggaagcc tcagtttggt cctcagcacc tgtaagaaca tttattctct catggtggaa    2160
gccagtcccc tcaccataga agatgagagg cacatcacat ctgtaacaaa cctgaaaacc    2220
ttgagtattc atgacctaca gaatcaacgg ctgccgggtg gtctgactga cagcttgggt    2280
aacttgaaga accttacaaa gctcataatg gataacataa agatgaatga agaagatgct    2340
ataaaactag ctgaaggcct gaaaaacctg aagaagatgt gtttatttca tttgacccac    2400
ttgtctgaca ttggagaggg aatggattac atagtcaagt ctctgtcaag tgaaccctgt    2460
gaccttgaag aaattcaatt agtctcctgc tgcttgtctg caaatgcagt gaaaatccta    2520
gctcagaatc ttcacaattt ggtcaaactg agcattcttg attatcaga aaattacctg     2580 gaaaaagatg gaaatgaagc tcttcatgaa ctgatcgaca ggatgaacgt gctagaacag    2640
ctcaccgcac tgatgctgcc ctggggctgt gacgtgcaag gcagcctgag cagcctgttg    2700
aaacatttgg aggaggtccc acaactcgtc aagcttgggt tgaaaaactg gagactcaca    2760
gatacagaga ttagaatttt aggtgcattt ttttggaaaga accctctgaa aaacttccag    2820
cagttgaatt tggcgggaaa tcgtgtgagc agtgatggat ggcttgcctt catgggtgta    2880
tttgagaatc ttaagcaatt agtgtttttt gactttagta ctaaagaatt tctacctgat    2940
ccagcattag tcagaaaact tagccaagtg ttatccaagt taacttttct gcaagaagct    3000
aggcttgttg ggtggcaatt tgatgatgat gatctcagtg ttattacagg tgcttttaaa    3060
ctagtaactg ct                                                       3072
```

```
<210> SEQ ID NO 4
<211> LENGTH: 3615
<212> TYPE: DNA
<213> ORGANISM: Homo sapiens
<220> FEATURE:
<221> NAME/KEY: CDS
<222> LOCATION: (1)...(3612)

<400> SEQUENCE: 4
```

```
atg ctg aac gct ggt ccc ctg ggc tcc ctt att tct ttc tct ata ctt      48
Met Leu Asn Ala Gly Pro Leu Gly Ser Leu Ile Ser Phe Ser Ile Leu
 1               5                  10                  15 tgt ctc tgt gtc ttt ttc ttt tcc aag tct ctc gtt cca cct aac gag      96
Cys Leu Cys Val Phe Phe Phe Ser Lys Ser Leu Val Pro Pro Asn Glu
            20                  25                  30 aaa cac cca cag aac aag aag gta tct ggt cta caa gaa ctc gag gcc    144
Lys His Pro Gln Asn Lys Lys Val Ser Gly Leu Gln Glu Leu Glu Ala
        35                  40                  45 tca ctg aaa cgg aaa gca aat aca aag aaa ctt tat ttt aaa aac atg    192
Ser Leu Lys Arg Lys Ala Asn Thr Lys Lys Leu Tyr Phe Lys Asn Met
    50                  55                  60 tct tgg tct ccc aag aag agg gca att gga ttg ctc agc cag aga ccc    240
```

-continued

```
Ser Trp Ser Pro Lys Lys Arg Ala Ile Gly Leu Leu Ser Gln Arg Pro
 65                  70                  75                  80 ttg cag gca gac aca caa gcg gct gga cgt cga gag gaa cac atc ggc      288
Leu Gln Ala Asp Thr Gln Ala Ala Gly Arg Arg Glu Glu His Ile Gly
                 85                  90                  95 gga aga aca tac aag cag ctg gac gtc cag agg acg ttg aag gga gaa      336
Gly Arg Thr Tyr Lys Gln Leu Asp Val Gln Arg Thr Leu Lys Gly Glu
            100                 105                 110 tgc tgg cgg aag agc aca caa cag aca tcg gca cgc cag cag gcc atc      384
Cys Trp Arg Lys Ser Thr Gln Gln Thr Ser Ala Arg Gln Gln Ala Ile
        115                 120                 125 cac cag agg aac gac tcg gag ttt ggc ctg gag gtg aat ttc ata aag      432
His Gln Arg Asn Asp Ser Glu Phe Gly Leu Glu Val Asn Phe Ile Lys
    130                 135                 140 gac aat agc cga gcc ctt att caa aga atg gga atg act gtt ata aag      480
Asp Asn Ser Arg Ala Leu Ile Gln Arg Met Gly Met Thr Val Ile Lys
145                 150                 155                 160 caa atc aca gat gac cta ttt gta tgg aat gtt ctg aat cgc gaa gaa      528
Gln Ile Thr Asp Asp Leu Phe Val Trp Asn Val Leu Asn Arg Glu Glu
                165                 170                 175 gta aac atc att tgc tgc gag aag gtg gag cag gat gct gct aga ggg      576
Val Asn Ile Ile Cys Cys Glu Lys Val Glu Gln Asp Ala Ala Arg Gly
            180                 185                 190 atc att cac atg att ttg aaa aag ggt tca gag tcc tgt aac ctc ttt      624
Ile Ile His Met Ile Leu Lys Lys Gly Ser Glu Ser Cys Asn Leu Phe
        195                 200                 205 ctt aaa tcc ctt aag gag tgg aac tat cct cta ttt cag gac ttg aat      672
Leu Lys Ser Leu Lys Glu Trp Asn Tyr Pro Leu Phe Gln Asp Leu Asn
    210                 215                 220 gga caa agt ttt gag gag aca cag aat tgg gtc ttc ttt aac atc acc      720
Gly Gln Ser Phe Glu Glu Thr Gln Asn Trp Val Phe Phe Asn Ile Thr
225                 230                 235                 240 tct tct cta ata ggt ctt ttt cat cag aca tca gaa gga gac ttg gac      768
Ser Ser Leu Ile Gly Leu Phe His Gln Thr Ser Glu Gly Asp Leu Asp
                245                 250                 255 gat ttg gct cag gat tta aag gac ttg tac cat acc cca tct ttt ctg      816
Asp Leu Ala Gln Asp Leu Lys Asp Leu Tyr His Thr Pro Ser Phe Leu
            260                 265                 270 aac ttt tat ccc ctt ggt gaa gat att gac att att ttt aac ttg aaa      864
Asn Phe Tyr Pro Leu Gly Glu Asp Ile Asp Ile Ile Phe Asn Leu Lys
        275                 280                 285 agc acc ttc aca gaa cct gtc ctg tgg agg aag gac caa cac cat cac      912
Ser Thr Phe Thr Glu Pro Val Leu Trp Arg Lys Asp Gln His His His
    290                 295                 300 cgc gtg gag cag ctg acc ctg aat ggc ctc ctg cag gct ctt cag agc      960
Arg Val Glu Gln Leu Thr Leu Asn Gly Leu Leu Gln Ala Leu Gln Ser
305                 310                 315                 320 ccc tgc atc att gaa ggg gaa tct ggc aaa ggc aag tcc act ctg ctg     1008
Pro Cys Ile Ile Glu Gly Glu Ser Gly Lys Gly Lys Ser Thr Leu Leu
                325                 330                 335 cag cga att gcc atg ctc tgg ggc tcc gga aag tgc aag gct ctg acc     1056
Gln Arg Ile Ala Met Leu Trp Gly Ser Gly Lys Cys Lys Ala Leu Thr
            340                 345                 350 aag ttc aaa ttc gtc ttc ttc ctc cgt ctc agc agg gcc cag ggt gga     1104
Lys Phe Lys Phe Val Phe Phe Leu Arg Leu Ser Arg Ala Gln Gly Gly
        355                 360                 365 ctt ttt gaa acc ctc tgt gat caa ctc ctg gat ata cct ggc aca atc     1152
Leu Phe Glu Thr Leu Cys Asp Gln Leu Leu Asp Ile Pro Gly Thr Ile
    370                 375                 380
```

-continued

| | |
|---|---|
| agg aag cag aca ttc atg gcc atg ctg ctg aag ctg cgg cag agg gtt<br>Arg Lys Gln Thr Phe Met Ala Met Leu Leu Lys Leu Arg Gln Arg Val<br>385                         390                       395                    400 | 1200 |
| ctt ttc ctt ctt gat ggc tac aat gaa ttc aag ccc cag aac tgc cca<br>Leu Phe Leu Leu Asp Gly Tyr Asn Glu Phe Lys Pro Gln Asn Cys Pro<br>                         405                       410                    415 | 1248 |
| gaa atc gaa gcc ctg ata aag gaa aac cac cgc ttc aag aac atg gtc<br>Glu Ile Glu Ala Leu Ile Lys Glu Asn His Arg Phe Lys Asn Met Val<br>                  420                     425                   430 | 1296 |
| atc gtc acc act acc act gag tgc ctg agg cac ata cgg cag ttt ggt<br>Ile Val Thr Thr Thr Thr Glu Cys Leu Arg His Ile Arg Gln Phe Gly<br>          435                     440                    445 | 1344 |
| gcc ctg act gct gag gtg ggg gat atg aca gaa gac agc gcc cag gct<br>Ala Leu Thr Ala Glu Val Gly Asp Met Thr Glu Asp Ser Ala Gln Ala<br>450                         455                       460 | 1392 |
| ctc atc cga gaa gtg ctg atc aag gag ctt gct gaa ggc ttg ttg ctc<br>Leu Ile Arg Glu Val Leu Ile Lys Glu Leu Ala Glu Gly Leu Leu Leu<br>465                         470                     475                    480 | 1440 |
| caa att cag aaa tcc agg tgc ttg agg aat ctc atg aag acc cct ctc<br>Gln Ile Gln Lys Ser Arg Cys Leu Arg Asn Leu Met Lys Thr Pro Leu<br>                  485                     490                   495 | 1488 |
| ttt gtg gtc atc act tgt gca atc cag atg ggt gaa agt gag ttc cac<br>Phe Val Val Ile Thr Cys Ala Ile Gln Met Gly Glu Ser Glu Phe His<br>               500                     505                    510 | 1536 |
| tct cac aca caa aca acg ctg ttc cat acc ttc tat gat ctg ttg ata<br>Ser His Thr Gln Thr Thr Leu Phe His Thr Phe Tyr Asp Leu Leu Ile<br>          515                     520                    525 | 1584 |
| cag aaa aac aaa cac aaa cat aaa ggt gtg gct gca agt gac ttc att<br>Gln Lys Asn Lys His Lys His Lys Gly Val Ala Ala Ser Asp Phe Ile<br>530                         535                       540 | 1632 |
| cgg agc ctg gac cac tgt gga gac cta gct ctg gag ggt gtg ttc tcc<br>Arg Ser Leu Asp His Cys Gly Asp Leu Ala Leu Glu Gly Val Phe Ser<br>545                         550                     555                    560 | 1680 |
| cac aag ttt gat ttc gaa ctg cag gat gtg tcc agc gtg aat gag gat<br>His Lys Phe Asp Phe Glu Leu Gln Asp Val Ser Ser Val Asn Glu Asp<br>                  565                     570                   575 | 1728 |
| gtc ctg ctg aca act ggg ctc ctc tgt aaa tat aca gct caa agg ttc<br>Val Leu Leu Thr Thr Gly Leu Leu Cys Lys Tyr Thr Ala Gln Arg Phe<br>               580                     585                    590 | 1776 |
| aag cca aag tat aaa ttc ttt cac aag tca ttc cag gag tac aca gca<br>Lys Pro Lys Tyr Lys Phe Phe His Lys Ser Phe Gln Glu Tyr Thr Ala<br>          595                     600                    605 | 1824 |
| gga cga aga ctc agc agt tta ttg acg tct cat gag cca gag gag gtg<br>Gly Arg Arg Leu Ser Ser Leu Leu Thr Ser His Glu Pro Glu Glu Val<br>610                         615                       620 | 1872 |
| acc aag ggg aat ggt tac ttg cag aaa atg gtt tcc att tcg gac att<br>Thr Lys Gly Asn Gly Tyr Leu Gln Lys Met Val Ser Ile Ser Asp Ile<br>625                         630                     635                    640 | 1920 |
| aca tcc act tat agc agc ctg ctc cgg tac acc tgt ggg tca tct gtg<br>Thr Ser Thr Tyr Ser Ser Leu Leu Arg Tyr Thr Cys Gly Ser Ser Val<br>               645                     650                    655 | 1968 |
| gaa gcc acc agg gct gtt atg aag cac ctc gca gca gtg tat caa cac<br>Glu Ala Thr Arg Ala Val Met Lys His Leu Ala Ala Val Tyr Gln His<br>          660                     665                    670 | 2016 |
| ggc tgc ctt ctc gga ctt tcc atc gcc aag agg cct ctc tgg aga cag<br>Gly Cys Leu Leu Gly Leu Ser Ile Ala Lys Arg Pro Leu Trp Arg Gln<br>675                         680                     685 | 2064 |
| gaa tct ttg caa agt gtg aaa aac acc act gag caa gaa att ctg aaa<br>Glu Ser Leu Gln Ser Val Lys Asn Thr Thr Glu Gln Glu Ile Leu Lys<br>690                         695                     700 | 2112 |

```
gcc ata aac atc aat tcc ttt gta gag tgt ggc atc cat tta tat caa    2160
Ala Ile Asn Ile Asn Ser Phe Val Glu Cys Gly Ile His Leu Tyr Gln
705                 710                 715                 720 gag agt aca tcc aaa tca gcc ctg agc caa gaa ttt gaa gct ttc ttt    2208
Glu Ser Thr Ser Lys Ser Ala Leu Ser Gln Glu Phe Glu Ala Phe Phe
                725                 730                 735 caa ggt aaa agc tta tat atc aac tca ggg aac atc ccc gat tac tta    2256
Gln Gly Lys Ser Leu Tyr Ile Asn Ser Gly Asn Ile Pro Asp Tyr Leu
            740                 745                 750 ttt gac ttc ttt gaa cat ttg ccc aat tgt gca agt gcc ctg gac ttc    2304
Phe Asp Phe Phe Glu His Leu Pro Asn Cys Ala Ser Ala Leu Asp Phe
        755                 760                 765 att aaa ctg gac ttt tat ggg gga gct atg gct tca tgg gaa aag gct    2352
Ile Lys Leu Asp Phe Tyr Gly Gly Ala Met Ala Ser Trp Glu Lys Ala
    770                 775                 780 gca gaa gac aca ggt gga atc cac atg gaa gag gcc cca gaa acc tac    2400
Ala Glu Asp Thr Gly Gly Ile His Met Glu Glu Ala Pro Glu Thr Tyr
785                 790                 795                 800 att ccc agc agg gct gta tct ttg ttc ttc aac tgg aag cag gaa ttc    2448
Ile Pro Ser Arg Ala Val Ser Leu Phe Phe Asn Trp Lys Gln Glu Phe
                805                 810                 815 agg act ctg gag gtc aca ctc cgg gat ttc agc aag ttg aat aag caa    2496
Arg Thr Leu Glu Val Thr Leu Arg Asp Phe Ser Lys Leu Asn Lys Gln
            820                 825                 830 gat atc aga tat ctg ggg aaa ata ttc agc tct gcc aca agc ctc agg    2544
Asp Ile Arg Tyr Leu Gly Lys Ile Phe Ser Ser Ala Thr Ser Leu Arg
        835                 840                 845 ctg caa ata aag aga tgt gct ggt gtg gct gga agc ctc agt ttg gtc    2592
Leu Gln Ile Lys Arg Cys Ala Gly Val Ala Gly Ser Leu Ser Leu Val
    850                 855                 860 ctc agc acc tgt aag aac att tat tct ctc atg gtg gaa gcc agt ccc    2640
Leu Ser Thr Cys Lys Asn Ile Tyr Ser Leu Met Val Glu Ala Ser Pro
865                 870                 875                 880 ctc acc ata gaa gat gag agg cac atc aca tct gta aca aac ctg aaa    2688
Leu Thr Ile Glu Asp Glu Arg His Ile Thr Ser Val Thr Asn Leu Lys
                885                 890                 895 acc ttg agt att cat gac cta cag aat caa cgg ctg ccg ggt ggt ctg    2736
Thr Leu Ser Ile His Asp Leu Gln Asn Gln Arg Leu Pro Gly Gly Leu
            900                 905                 910 act gac agc ttg ggt aac ttg aag aac ctt aca aag ctc ata atg gat    2784
Thr Asp Ser Leu Gly Asn Leu Lys Asn Leu Thr Lys Leu Ile Met Asp
        915                 920                 925 aac ata aag atg aat gaa gaa gat gct ata aaa cta gct gaa ggc ctg    2832
Asn Ile Lys Met Asn Glu Glu Asp Ala Ile Lys Leu Ala Glu Gly Leu
    930                 935                 940 aaa aac ctg aag aag atg tgt tta ttt cat ttg acc cac ttg tct gac    2880
Lys Asn Leu Lys Lys Met Cys Leu Phe His Leu Thr His Leu Ser Asp
945                 950                 955                 960 att gga gag gga atg gat tac ata gtc aag tct ctg tca agt gaa ccc    2928
Ile Gly Glu Gly Met Asp Tyr Ile Val Lys Ser Leu Ser Ser Glu Pro
                965                 970                 975 tgt gac ctt gaa gaa att caa tta gtc tcc tgc tgc ttg tct gca aat    2976
Cys Asp Leu Glu Glu Ile Gln Leu Val Ser Cys Cys Leu Ser Ala Asn
            980                 985                 990 gca gtg aaa atc cta gct cag aat ctt cac aat ttg gtc aaa ctg agc    3024
Ala Val Lys Ile Leu Ala Gln Asn Leu His Asn Leu Val Lys Leu Ser
        995                 1000                1005 att ctt gat tta tca gaa aat tac ctg gaa aaa gat gga aat gaa gct    3072
Ile Leu Asp Leu Ser Glu Asn Tyr Leu Glu Lys Asp Gly Asn Glu Ala
```

```
                1010                1015                1020
ctt cat gaa ctg atc gac agg atg aac gtg cta gaa cag ctc acc gca        3120
Leu His Glu Leu Ile Asp Arg Met Asn Val Leu Glu Gln Leu Thr Ala
1025                1030                1035                1040 ctg atg ctg ccc tgg ggc tgt gac gtg caa ggc agc ctg agc agc ctg        3168
Leu Met Leu Pro Trp Gly Cys Asp Val Gln Gly Ser Leu Ser Ser Leu
                1045                1050                1055 ttg aaa cat ttg gag gag gtc cca caa ctc gtc aag ctt ggg ttg aaa        3216
Leu Lys His Leu Glu Glu Val Pro Gln Leu Val Lys Leu Gly Leu Lys
        1060                1065                1070 aac tgg aga ctc aca gat aca gag att aga att tta ggt gca ttt ttt        3264
Asn Trp Arg Leu Thr Asp Thr Glu Ile Arg Ile Leu Gly Ala Phe Phe
    1075                1080                1085 gga aag aac cct ctg aaa aac ttc cag cag ttg aat ttg gcg gga aat        3312
Gly Lys Asn Pro Leu Lys Asn Phe Gln Gln Leu Asn Leu Ala Gly Asn
1090                1095                1100 cgt gtg agc agt gat gga tgg ctt gcc ttc atg ggt gta ttt gag aat        3360
Arg Val Ser Ser Asp Gly Trp Leu Ala Phe Met Gly Val Phe Glu Asn
1105                1110                1115                1120 ctt aag caa tta gtg ttt ttt gac ttt agt act aaa gaa ttt cta cct        3408
Leu Lys Gln Leu Val Phe Phe Asp Phe Ser Thr Lys Glu Phe Leu Pro
            1125                1130                1135 gat cca gca tta gtc aga aaa ctt agc caa gtg tta tcc aag tta act        3456
Asp Pro Ala Leu Val Arg Lys Leu Ser Gln Val Leu Ser Lys Leu Thr
    1140                1145                1150 ttt ctg caa gaa gct agg ctt gtt ggg tgg caa ttt gat gat gat gat        3504
Phe Leu Gln Glu Ala Arg Leu Val Gly Trp Gln Phe Asp Asp Asp Asp
        1155                1160                1165 ctc agt gtt att aca gat gag aaa gct cag atg att tgc cca tgg gtt        3552
Leu Ser Val Ile Thr Asp Glu Lys Ala Gln Met Ile Cys Pro Trp Val
1170                1175                1180 ata aaa cta ctt cct tac aca gtg gca gca tca gaa ctg gaa ttc aga        3600
Ile Lys Leu Leu Pro Tyr Thr Val Ala Ala Ser Glu Leu Glu Phe Arg
1185                1190                1195                1200 tct ctt gcc tcc tag                                                    3615
Ser Leu Ala Ser <210> SEQ ID NO 5
<211> LENGTH: 1204
<212> TYPE: PRT
<213> ORGANISM: Homo sapiens

<400> SEQUENCE: 5

Met Leu Asn Ala Gly Pro Leu Gly Ser Leu Ile Ser Phe Ser Ile Leu
1               5                   10                  15

Cys Leu Cys Val Phe Phe Ser Lys Ser Leu Val Pro Pro Asn Glu
            20                  25                  30

Lys His Pro Gln Asn Lys Lys Val Ser Gly Leu Gln Glu Leu Glu Ala
        35                  40                  45

Ser Leu Lys Arg Lys Ala Asn Thr Lys Lys Leu Tyr Phe Lys Asn Met
    50                  55                  60

Ser Trp Ser Pro Lys Lys Arg Ala Ile Gly Leu Leu Ser Gln Arg Pro
65                  70                  75                  80

Leu Gln Ala Asp Thr Gln Ala Ala Gly Arg Glu Glu His Ile Gly
            85                  90                  95

Gly Arg Thr Tyr Lys Gln Leu Asp Val Gln Arg Thr Leu Lys Gly Glu
            100                 105                 110

Cys Trp Arg Lys Ser Thr Gln Gln Thr Ser Ala Arg Gln Gln Ala Ile
```

-continued

```
            115                 120                 125
His Gln Arg Asn Asp Ser Glu Phe Gly Leu Glu Val Asn Phe Ile Lys
    130                 135                 140

Asp Asn Ser Arg Ala Leu Ile Gln Arg Met Gly Met Thr Val Ile Lys
145                 150                 155                 160

Gln Ile Thr Asp Asp Leu Phe Val Trp Asn Val Leu Asn Arg Glu Glu
                165                 170                 175

Val Asn Ile Ile Cys Cys Glu Lys Val Glu Gln Asp Ala Ala Arg Gly
                180                 185                 190

Ile Ile His Met Ile Leu Lys Lys Gly Ser Glu Ser Cys Asn Leu Phe
                195                 200                 205

Leu Lys Ser Leu Lys Glu Trp Asn Tyr Pro Leu Phe Gln Asp Leu Asn
    210                 215                 220

Gly Gln Ser Phe Glu Glu Thr Gln Asn Trp Val Phe Phe Asn Ile Thr
225                 230                 235                 240

Ser Ser Leu Ile Gly Leu Phe His Gln Thr Ser Glu Gly Asp Leu Asp
                245                 250                 255

Asp Leu Ala Gln Asp Leu Lys Asp Leu Tyr His Thr Pro Ser Phe Leu
                260                 265                 270

Asn Phe Tyr Pro Leu Gly Glu Asp Ile Asp Ile Phe Asn Leu Lys
                275                 280                 285

Ser Thr Phe Thr Glu Pro Val Leu Trp Arg Lys Asp Gln His His His
    290                 295                 300

Arg Val Glu Gln Leu Thr Leu Asn Gly Leu Leu Gln Ala Leu Gln Ser
305                 310                 315                 320

Pro Cys Ile Ile Glu Gly Glu Ser Gly Lys Gly Lys Ser Thr Leu Leu
                325                 330                 335

Gln Arg Ile Ala Met Leu Trp Gly Ser Gly Lys Cys Lys Ala Leu Thr
                340                 345                 350

Lys Phe Lys Phe Val Phe Phe Leu Arg Leu Ser Arg Ala Gln Gly Gly
    355                 360                 365

Leu Phe Glu Thr Leu Cys Asp Gln Leu Leu Asp Ile Pro Gly Thr Ile
    370                 375                 380

Arg Lys Gln Thr Phe Met Ala Met Leu Leu Lys Leu Arg Gln Arg Val
385                 390                 395                 400

Leu Phe Leu Leu Asp Gly Tyr Asn Glu Phe Lys Pro Gln Asn Cys Pro
                405                 410                 415

Glu Ile Glu Ala Leu Ile Lys Glu Asn His Arg Phe Lys Asn Met Val
                420                 425                 430

Ile Val Thr Thr Thr Thr Glu Cys Leu Arg His Ile Arg Gln Phe Gly
                435                 440                 445

Ala Leu Thr Ala Glu Val Gly Asp Met Thr Glu Asp Ser Ala Gln Ala
    450                 455                 460

Leu Ile Arg Glu Val Leu Ile Lys Glu Leu Ala Glu Gly Leu Leu Leu
465                 470                 475                 480

Gln Ile Gln Lys Ser Arg Cys Leu Arg Asn Leu Met Lys Thr Pro Leu
                485                 490                 495

Phe Val Val Ile Thr Cys Ala Ile Gln Met Gly Glu Ser Glu Phe His
                500                 505                 510

Ser His Thr Gln Thr Thr Leu Phe His Thr Phe Tyr Asp Leu Leu Ile
    515                 520                 525

Gln Lys Asn Lys His Lys His Lys Gly Val Ala Ala Ser Asp Phe Ile
    530                 535                 540
```

-continued

```
Arg Ser Leu Asp His Cys Gly Asp Leu Ala Leu Glu Gly Val Phe Ser
545                 550                 555                 560

His Lys Phe Asp Phe Glu Leu Gln Asp Val Ser Ser Val Asn Glu Asp
                565                 570                 575

Val Leu Leu Thr Thr Gly Leu Leu Cys Lys Tyr Thr Ala Gln Arg Phe
            580                 585                 590

Lys Pro Lys Tyr Lys Phe Phe His Lys Ser Phe Gln Glu Tyr Thr Ala
        595                 600                 605

Gly Arg Arg Leu Ser Ser Leu Leu Thr Ser His Glu Pro Glu Glu Val
    610                 615                 620

Thr Lys Gly Asn Gly Tyr Leu Gln Lys Met Val Ser Ile Ser Asp Ile
625                 630                 635                 640

Thr Ser Thr Tyr Ser Ser Leu Leu Arg Tyr Thr Cys Gly Ser Ser Val
                645                 650                 655

Glu Ala Thr Arg Ala Val Met Lys His Leu Ala Ala Val Tyr Gln His
            660                 665                 670

Gly Cys Leu Leu Gly Leu Ser Ile Ala Lys Arg Pro Leu Trp Arg Gln
        675                 680                 685

Glu Ser Leu Gln Ser Val Lys Asn Thr Thr Glu Gln Glu Ile Leu Lys
    690                 695                 700

Ala Ile Asn Ile Asn Ser Phe Val Glu Cys Gly Ile His Leu Tyr Gln
705                 710                 715                 720

Glu Ser Thr Ser Lys Ser Ala Leu Ser Gln Glu Phe Glu Ala Phe Phe
                725                 730                 735

Gln Gly Lys Ser Leu Tyr Ile Asn Ser Gly Asn Ile Pro Asp Tyr Leu
            740                 745                 750

Phe Asp Phe Phe Glu His Leu Pro Asn Cys Ala Ser Ala Leu Asp Phe
        755                 760                 765

Ile Lys Leu Asp Phe Tyr Gly Gly Ala Met Ala Ser Trp Glu Lys Ala
    770                 775                 780

Ala Glu Asp Thr Gly Gly Ile His Met Glu Glu Ala Pro Glu Thr Tyr
785                 790                 795                 800

Ile Pro Ser Arg Ala Val Ser Leu Phe Phe Asn Trp Lys Gln Glu Phe
                805                 810                 815

Arg Thr Leu Glu Val Thr Leu Arg Asp Phe Ser Lys Leu Asn Lys Gln
            820                 825                 830

Asp Ile Arg Tyr Leu Gly Lys Ile Phe Ser Ser Ala Thr Ser Leu Arg
        835                 840                 845

Leu Gln Ile Lys Arg Cys Ala Gly Val Ala Gly Ser Leu Ser Leu Val
    850                 855                 860

Leu Ser Thr Cys Lys Asn Ile Tyr Ser Leu Met Val Glu Ala Ser Pro
865                 870                 875                 880

Leu Thr Ile Glu Asp Glu Arg His Ile Thr Ser Val Thr Asn Leu Lys
                885                 890                 895

Thr Leu Ser Ile His Asp Leu Gln Asn Gln Arg Leu Pro Gly Gly Leu
            900                 905                 910

Thr Asp Ser Leu Gly Asn Leu Lys Asn Leu Thr Lys Leu Ile Met Asp
        915                 920                 925

Asn Ile Lys Met Asn Glu Glu Asp Ala Ile Lys Leu Ala Glu Gly Leu
    930                 935                 940

Lys Asn Leu Lys Lys Met Cys Leu Phe His Leu Thr His Leu Ser Asp
945                 950                 955                 960
```

```
Ile Gly Glu Gly Met Asp Tyr Ile Val Lys Ser Leu Ser Ser Glu Pro
            965                 970                 975
Cys Asp Leu Glu Glu Ile Gln Leu Val Ser Cys Cys Leu Ser Ala Asn
            980                 985                 990
Ala Val Lys Ile Leu Ala Gln Asn Leu His Asn Leu Val Lys Leu Ser
            995                 1000                1005
Ile Leu Asp Leu Ser Glu Asn Tyr Leu Glu Lys Asp Gly Asn Glu Ala
        1010                1015                1020
Leu His Glu Leu Ile Asp Arg Met Asn Val Leu Glu Gln Leu Thr Ala
1025                1030                1035                1040
Leu Met Leu Pro Trp Gly Cys Asp Val Gln Gly Ser Leu Ser Ser Leu
                1045                1050                1055
Leu Lys His Leu Glu Glu Val Pro Gln Leu Val Lys Leu Gly Leu Lys
                1060                1065                1070
Asn Trp Arg Leu Thr Asp Thr Glu Ile Arg Ile Leu Gly Ala Phe Phe
            1075                1080                1085
Gly Lys Asn Pro Leu Lys Asn Phe Gln Gln Leu Asn Leu Ala Gly Asn
        1090                1095                1100
Arg Val Ser Ser Asp Gly Trp Leu Ala Phe Met Gly Val Phe Glu Asn
1105                1110                1115                1120
Leu Lys Gln Leu Val Phe Phe Asp Phe Ser Thr Lys Glu Phe Leu Pro
                1125                1130                1135
Asp Pro Ala Leu Val Arg Lys Leu Ser Gln Val Leu Ser Lys Leu Thr
                1140                1145                1150
Phe Leu Gln Glu Ala Arg Leu Val Gly Trp Gln Phe Asp Asp Asp Asp
            1155                1160                1165
Leu Ser Val Ile Thr Asp Glu Lys Ala Gln Met Ile Cys Pro Trp Val
        1170                1175                1180
Ile Lys Leu Leu Pro Tyr Thr Val Ala Ala Ser Glu Leu Glu Phe Arg
1185                1190                1195                1200
Ser Leu Ala Ser

<210> SEQ ID NO 6
<211> LENGTH: 3612
<212> TYPE: DNA
<213> ORGANISM: Homo sapiens

<400> SEQUENCE: 6
atgctgaacg ctggtcccct gggctcccct atttctttct ctatactttg tctctgtgtc    60
tttttctttt ccaagtctct cgttccacct aacgagaaac acccacagaa caagaaggta   120
tctggtctac aagaactcga ggcctcactg aaacggaaag caaatacaaa gaaactttat   180
tttaaaaaca tgtcttggtc tcccaagaag agggcaattg gattgctcag ccagagaccc   240
ttgcaggcag acacacaagc ggctggacgt cgagaggaac acatcggcgg aagaacatac   300
aagcagctgg acgtccagag gacgttgaag ggagaatgct ggcggaagag cacacaacag   360
acatcggcac gccagcaggc catccaccag aggaacgact cggagtttgg cctggaggtg   420
aatttcataa aggacaatag ccgagccctt attcaaagaa tgggaatgac tgttataaag   480
caaatcacag atgacctatt tgtatggaat gttctgaatc gcaagaagt aaacatcatt   540
tgctgcgaga aggtggagca ggatgctgct agagggatca ttcacatgat tttgaaaaag   600
ggttcagagt cctgtaacct ctttcttaaa tcccttaagg agtggaacta tcctctattt   660
caggacttga atggacaaag ttttgaggag acacagaatt gggtcttctt taacatcacc   720
```

```
tcttctctaa taggtctttt tcatcagaca tcagaaggag acttggacga tttggctcag      780
gatttaaagg acttgtacca tacccoatct tttctgaact tttatcccct tggtgaagat      840
attgacatta ttttaactt gaaaagcacc ttcacagaac ctgtcctgtg gaggaaggac       900
caacaccatc accgcgtgga gcagctgacc ctgaatggcc tcctgcaggc tcttcagagc      960
ccctgcatca ttgaagggga atctggcaaa ggcaagtcca ctctgctgca gcgaattgcc     1020
atgctctggg gctccggaaa gtgcaaggct ctgaccaagt tcaaattcgt cttcttcctc     1080
cgtctcagca gggcccaggg tggacttttt gaaaccctct gtgatcaact cctggatata     1140
cctggcacaa tcaggaagca gacattcatg gccatgctgc tgaagctgcg gcagagggtt     1200
cttttccttc ttgatggcta caatgaattc aagccccaga actgcccaga aatcgaagcc     1260
ctgataaagg aaaaccaccg cttcaagaac atggtcatcg tcaccactac cactgagtgc     1320
ctgaggcaca tacggcagtt tggtgccctg actgctgagg tgggggatat gacagaagac     1380
agcgcccagg ctctcatccg agaagtgctg atcaaggagc ttgctgaagg cttgttgctc     1440
caaattcaga aatccaggtg cttgaggaat ctcatgaaga cccctctctt tgtggtcatc     1500
acttgtgcaa tccagatggg tgaaagtgag ttccactctc acacacaaac aacgctgttc     1560
catacctttc tatgatctgtt gatacagaaa acaaacaca aacataaagg tgtggctgca     1620
agtgacttca ttcggagcct ggaccactgt ggagacctag ctctggaggg tgtgttctcc     1680
cacaagtttg atttcgaact gcaggatgtg tccagcgtga atgaggatgt cctgctgaca     1740
actgggctcc tctgtaaata tacagctcaa aggttcaagc caaagtataa attcttttcac    1800 aagtcattcc aggagtacac agcaggacga agactcagca gtttattgac gtctcatgag     1860
ccagaggagg tgaccaaggg gaatggttac ttgcagaaaa tggtttccat ttcggacatt     1920
acatccactt atagcagcct gctccggtac acctgtgggt catctgtgga agccaccagg     1980
gctgttatga agcacctcgc agcagtgtat caacacggct gccttctcgg actttccatc     2040
gccaagaggc ctctctggag acaggaatct ttgcaaagtg tgaaaaacac cactgagcaa     2100
gaaattctga agccataaa catcaattcc tttgtagagt gtggcatcca tttatatcaa      2160
gagagtacat ccaaatcagc cctgagccaa gaatttgaag ctttctttca aggtaaaagc     2220
ttatatatca actcagggaa catccccgat tacttatttg acttctttga acatttgccc     2280
aattgtgcaa gtgccctgga cttcattaaa ctggactttt atgggggagc tatggcttca     2340
tgggaaaagg ctgcagaaga cacaggtgga atccacatgg aagaggcccc agaaacctac     2400
attcccagca gggctgtatc tttgttcttc aactggaagc aggaattcag gactctggag     2460
gtcacactcc gggatttcag caagttgaat aagcaagata tcagatatct ggggaaaata     2520
ttcagctctg ccacaagcct caggctgcaa ataaagagat gtgctggtgt ggctggaagc     2580
ctcagtttgg tcctcagcac ctgtaagaac atttattctc tcatggtgga agccagtccc     2640
ctcaccatag aagatgagag gcacatcaca tctgtaacaa acctgaaaac cttgagtatt     2700
catgacctac agaatcaacg gctgccgggt ggtctgactg acagcttggg taacttgaag     2760
aaccttacaa agctcataat ggataacata agatgaatg aagaagatgc tataaaacta      2820
gctgaaggcc tgaaaaacct gaagaagatg tgtttatttc atttgaccca cttgtctgac     2880 attgagagg gaatggatta catagtcaag tctctgtcaa gtgaacoctg tgaccttgaa      2940 gaaattcaat tagtctcctg ctgcttgtct gcaaatgcag tgaaaatcct agctcagaat     3000
cttcacaatt tggtcaaact gagcattctt gatttatcag aaaattacct ggaaaaagat     3060
ggaaatgaag ctcttcatga actgatcgac aggatgaacg tgctagaaca gctcaccgca     3120
```

-continued

```
ctgatgctgc cctggggctg tgacgtgcaa ggcagcctga gcagcctgtt gaaacatttg    3180
gaggaggtcc cacaactcgt caagcttggg ttgaaaaact ggagactcac agatacagag    3240
attagaattt taggtgcatt ttttggaaag aaccctctga aaacttcca gcagttgaat    3300 ttggcgggaa atcgtgtgag cagtgatgga tggcttgcct tcatgggtgt atttgagaat    3360
cttaagcaat tagtgttttt tgactttagt actaaagaat ttctacctga tccagcatta    3420
gtcagaaaac ttagccaagt gttatccaag ttaactttc tgcaagaagc taggcttgtt    3480
gggtggcaat tgatgatga tgatctcagt gttattacag atgagaaagc tcagatgatt    3540
tgcccatggg ttataaaact acttccttac acagtggcag catcagaact ggaattcaga    3600
tctcttgcct cc                                                        3612
```

<210> SEQ ID NO 7
<211> LENGTH: 90
<212> TYPE: PRT
<213> ORGANISM: Artificial Sequence
<220> FEATURE:
<223> OTHER INFORMATION: consensus sequence

<400> SEQUENCE: 7

```
Ala Glu Asp Asp Arg Arg Leu Leu Arg Lys Asn Arg Leu Glu Leu Leu
 1               5                  10                  15

Gly Glu Leu Thr Leu Ser Gly Leu Leu Asp His Leu Leu Glu Lys Asn
            20                  25                  30

Val Leu Thr Glu Glu Glu Glu Lys Ile Lys Ala Lys Asn Thr Thr
        35                  40                  45

Arg Arg Asp Lys Ala Arg Glu Leu Ile Asp Ser Val Gln Lys Lys Gly
    50                  55                  60

Asn Gln Ala Phe Gln Ile Phe Leu Gln Ala Leu Arg Glu Thr Asp Gln
65                  70                  75                  80

Glu Leu Leu Ala Asp Leu Leu Leu Asp Glu
                85                  90
```

<210> SEQ ID NO 8
<211> LENGTH: 23
<212> TYPE: PRT
<213> ORGANISM: Artificial Sequence
<220> FEATURE:
<223> OTHER INFORMATION: consensus sequence

<400> SEQUENCE: 8

```
Asn Leu Glu Glu Leu Asp Leu Ser Asn Asn Leu Thr Ser Leu Pro Pro
 1               5                  10                  15

Gly Leu Phe Ser Asn Leu Pro
            20
```

<210> SEQ ID NO 9
<211> LENGTH: 781
<212> TYPE: PRT
<213> ORGANISM: Homo sapiens

<400> SEQUENCE: 9

```
Glu Leu Val Leu Pro Glu Val Phe Gly Asn Leu Asn Ser Val Met Cys
 1               5                  10                  15

Val Glu Gly Glu Ala Gly Ser Gly Lys Thr Val Leu Leu Lys Lys Ile
            20                  25                  30

Ala Phe Leu Trp Ala Ser Gly Cys Cys Pro Leu Leu Asn Arg Phe Gln
        35                  40                  45
```

```
Leu Val Phe Tyr Leu Ser Leu Ser Ser Thr Arg Pro Asp Glu Gly Leu
         50                  55                  60

Ala Ser Ile Ile Cys Asp Gln Leu Leu Glu Lys Glu Gly Ser Val Thr
65                  70                  75                  80

Glu Met Cys Met Arg Asn Ile Ile Gln Gln Leu Lys Asn Gln Val Leu
                 85                  90                  95

Phe Leu Leu Asp Asp Tyr Lys Glu Ile Cys Ser Ile Pro Gln Val Ile
            100                 105                 110

Gly Lys Leu Ile Gln Lys Asn His Leu Ser Arg Thr Cys Leu Leu Ile
        115                 120                 125

Ala Val Arg Thr Asn Arg Ala Arg Asp Ile Arg Arg Tyr Leu Glu Thr
    130                 135                 140

Ile Leu Glu Ile Gln Ala Phe Pro Phe Tyr Asn Thr Val Cys Ile Leu
145                 150                 155                 160

Arg Lys Leu Phe Ser His Asn Met Thr Arg Leu Arg Lys Phe Met Val
                165                 170                 175

Tyr Phe Gly Lys Asn Gln Ser Leu Gln Lys Ile Gln Lys Thr Pro Leu
            180                 185                 190

Phe Val Ala Ala Ile Cys Ala His Trp Phe Gln Tyr Pro Phe Asp Pro
        195                 200                 205

Ser Phe Asp Asp Val Ala Val Phe Lys Ser Tyr Met Glu Arg Leu Ser
    210                 215                 220

Leu Arg Asn Lys Ala Thr Ala Glu Ile Leu Lys Ala Thr Val Ser Ser
225                 230                 235                 240

Cys Gly Glu Leu Ala Leu Lys Gly Phe Phe Ser Cys Cys Phe Glu Phe
                245                 250                 255

Asn Asp Asp Asp Leu Ala Glu Ala Gly Val Asp Glu Asp Glu Asp Leu
            260                 265                 270

Thr Met Cys Leu Met Ser Lys Phe Thr Ala Gln Arg Leu Arg Pro Phe
        275                 280                 285

Tyr Arg Phe Leu Ser Pro Ala Phe Gln Glu Phe Leu Ala Gly Met Arg
    290                 295                 300

Leu Ile Glu Leu Leu Asp Ser Asp Arg Gln Glu His Gln Asp Leu Gly
305                 310                 315                 320

Leu Tyr His Leu Lys Gln Ile Asn Ser Pro Met Met Thr Val Ser Ala
                325                 330                 335

Tyr Asn Asn Phe Leu Asn Tyr Val Ser Ser Leu Pro Ser Thr Lys Ala
            340                 345                 350

Gly Pro Lys Ile Val Ser His Leu Leu His Leu Val Asp Asn Lys Glu
        355                 360                 365

Ser Leu Glu Asn Ile Ser Glu Asn Asp Asp Tyr Leu Lys His Gln Pro
    370                 375                 380

Glu Ile Ser Leu Gln Met Gln Leu Leu Arg Gly Leu Trp Gln Ile Cys
385                 390                 395                 400

Pro Gln Ala Tyr Phe Ser Met Val Ser Glu His Leu Leu Val Leu Ala
                405                 410                 415

Leu Lys Thr Ala Tyr Gln Ser Asn Thr Val Ala Ala Cys Ser Pro Phe
            420                 425                 430

Val Leu Gln Phe Leu Gln Gly Arg Thr Leu Thr Leu Gly Ala Leu Asn
        435                 440                 445

Leu Gln Tyr Phe Phe Asp His Pro Glu Ser Leu Ser Leu Leu Arg Ser
    450                 455                 460
```

```
Ile His Phe Ser Ile Arg Gly Asn Lys Thr Ser Pro Arg Ala His Phe
465                 470                 475                 480

Ser Val Leu Glu Thr Cys Phe Asp Lys Ser Gln Val Pro Thr Ile Asp
                485                 490                 495

Gln Asp Tyr Ala Ser Ala Phe Glu Pro Met Asn Glu Trp Glu Arg Asn
            500                 505                 510

Leu Ala Glu Lys Glu Asp Asn Val Lys Ser Tyr Met Asp Met Gln Arg
            515                 520                 525

Arg Ala Ser Pro Asp Leu Ser Thr Gly Tyr Trp Lys Leu Ser Pro Lys
            530                 535                 540

Gln Tyr Lys Ile Pro Cys Leu Glu Val Asp Val Asn Asp Ile Asp Val
545                 550                 555                 560

Val Gly Gln Asp Met Leu Glu Ile Leu Met Thr Val Phe Ser Ala Ser
                565                 570                 575

Gln Arg Ile Glu Leu His Leu Asn His Ser Arg Gly Phe Ile Glu Ser
                580                 585                 590

Ile Arg Pro Ala Leu Glu Leu Ser Lys Ala Ser Val Thr Lys Cys Ser
            595                 600                 605

Ile Ser Lys Leu Glu Leu Ser Ala Ala Glu Gln Glu Leu Leu Leu Thr
            610                 615                 620

Leu Pro Ser Leu Glu Ser Leu Glu Val Ser Gly Thr Ile Gln Ser Gln
625                 630                 635                 640

Asp Gln Ile Phe Pro Asn Leu Asp Lys Phe Leu Cys Leu Lys Glu Leu
                645                 650                 655

Ser Val Asp Leu Glu Gly Asn Ile Asn Val Phe Ser Val Ile Pro Glu
                660                 665                 670

Glu Phe Pro Asn Phe His His Met Glu Lys Leu Leu Ile Gln Ile Ser
                675                 680                 685

Ala Glu Tyr Asp Pro Ser Lys Leu Val Ala Ser Leu Pro Asn Phe Ile
            690                 695                 700

Ser Leu Lys Ile Leu Asn Leu Glu Gly Gln Gln Phe Pro Asp Glu Glu
705                 710                 715                 720

Thr Ser Glu Lys Phe Ala Tyr Ile Leu Gly Ser Leu Ser Asn Leu Glu
                725                 730                 735

Glu Leu Ile Leu Pro Thr Gly Asp Gly Ile Tyr Arg Val Ala Lys Leu
                740                 745                 750

Ile Ile Gln Gln Cys Gln Gln Leu His Cys Leu Arg Val Leu Ser Phe
            755                 760                 765

Phe Lys Thr Leu Asn Asp Asp Ser Val Val Glu Ile Gly
            770                 775                 780

<210> SEQ ID NO 10
<211> LENGTH: 202
<212> TYPE: PRT
<213> ORGANISM: Artificial Sequence
<220> FEATURE:
<223> OTHER INFORMATION: consensus sequence

<400> SEQUENCE: 10

Glu Leu Leu Leu Ser Glu Gly Glu Gly Gly Lys Leu Leu Ile Ala Leu
 1               5                  10                  15

Trp Ser Gly Cys Leu Phe Val Phe Leu Leu Ser Arg Gly Leu Cys Asp
            20                  25                  30

Gln Leu Leu Gly Leu Val Leu Phe Leu Leu Asp Tyr Glu Cys Ile Leu
            35                  40                  45
```

-continued

```
Ile Asn His Thr Arg Ile Arg Glu Arg Lys Leu Lys Thr Pro Leu Phe
 50                  55                  60

Val Cys Ala Phe Phe Leu Asn Lys Ala Cys Gly Leu Ala Leu Gly Phe
 65                  70                  75                  80

Ser Phe Phe Asp Val Glu Asp Leu Thr Leu Lys Thr Ala Gln Arg Pro
                 85                  90                  95

Tyr Phe Phe Gln Glu Ala Gly Arg Leu Leu Ser Glu Gly Leu Ser
                100                 105                 110

Ser Tyr Leu Tyr Ser Ala His Leu Leu Ser Leu Gln Leu Gln Val Tyr
            115                 120                 125

Gln Thr Phe Gln Gly Leu Asn Tyr Phe His Pro Ser Leu Ile Gly
        130                 135                 140

Pro Tyr Ala Trp Glu Leu Ile Cys Leu Val Ser Gln Arg Leu Ser Ile
145                 150                 155                 160

Lys Cys Leu Ser Ser Leu Ser Leu Glu Gln Asn Leu Lys Leu Leu Glu
                165                 170                 175

Gly Asn Ile Leu Ser Leu Leu Leu Leu Asp Glu Ala Leu Asn Leu
            180                 185                 190

Leu Gly Lys Leu Leu Leu Phe Asp Asp Ile
        195                 200
```

<210> SEQ ID NO 11
<211> LENGTH: 898
<212> TYPE: PRT
<213> ORGANISM: Artificial Sequence
<220> FEATURE:
<223> OTHER INFORMATION: majority sequence

<400> SEQUENCE: 11

```
Glu Gln Leu Val Leu Asn Gly Val Leu Gly Ala Leu Asn Ser Val Cys
  1               5                  10                  15

Ile Val Glu Gly Glu Ala Gly Ser Gly Lys Ser Val Leu Leu Gln Lys
                 20                  25                  30

Ile Ala Phe Leu Trp Gly Ser Gly Lys Cys Lys Ala Leu Thr Lys Phe
             35                  40                  45

Gln Leu Val Phe Phe Leu Ser Leu Ser Ser Thr Arg Ala Asp Gly Gly
 50                  55                  60

Leu Ala Ser Ile Leu Cys Asp Gln Leu Leu Asp Ile Glu Gly Ser Val
 65                  70                  75                  80

Thr Glu Gln Thr Phe Arg Ala Ile Leu Leu Gln Leu Lys Asn Gln Val
                 85                  90                  95

Leu Phe Leu Leu Asp Gly Tyr Asn Glu Ile Lys Pro Gln Asn Cys Ser
                100                 105                 110

Ile Pro Gln Val Ile Gly Ala Leu Ile Gln Glu Asn His Leu Ser Lys
            115                 120                 125

Thr Cys Val Leu Val Ala Val Thr Thr Glu Arg Ala Arg Asp Ile Arg
        130                 135                 140

Gln Phe Gly Ala Leu Ile Ala Glu Val Gly Ala Phe Thr Glu Asp Ser
145                 150                 155                 160

Ala Val Ala Leu Leu Arg Glu Val Leu Ile Lys Glu Leu Ala Glu Leu
                165                 170                 175

Arg Gly Leu Leu Val Gln Ile Gly Lys Ser Gln Ser Leu Gln Asn Leu
            180                 185                 190

Gln Lys Thr Pro Leu Phe Val Ala Ala Ile Cys Ala Ile Gln Trp Gly
        195                 200                 205
```

-continued

```
Glu Ser Glu Phe Asp Ser Ser Phe Thr Asp Val Ala Val Phe Lys Ser
    210                 215                 220
Phe Tyr Asp Leu Leu Ile Leu Lys Asn Lys His Lys His Gly Val Ala
225                 230                 235                 240
Ala Ala Asp Ile Leu Lys Ala Thr Val Ser Ser Cys Gly Asp Leu Ala
                245                 250                 255
Leu Glu Gly Val Phe Ser His Lys Phe Asp Phe Glu Leu Asp Asp Val
            260                 265                 270
Ala Glu Ala Gly Val Asp Glu Asp Val Leu Leu Thr Thr Gly Leu Leu
        275                 280                 285
Ser Lys Phe Thr Ala Gln Arg Leu Lys Pro Lys Tyr Lys Phe Leu Ser
    290                 295                 300
Lys Ala Phe Gln Glu Phe Leu Ala Gly Arg Arg Leu Ile Ser Leu Leu
305                 310                 315                 320
Thr Ser Asp Glu Gln Glu Val Thr Leu Gly Leu Gly His Leu Gln
                325                 330                 335
Gln Ile Val Ser Ile Ser Asp Ile Val Ser Ala Tyr Ser Ser Leu Leu
            340                 345                 350
Asn Tyr Val Ser Gly Leu Ser Ser Val Glu Ala Gly Arg Ala Val Val
        355                 360                 365
Ser His Leu Ala Ala Val Val Asp Asn Lys Gly Ser Leu Leu Gly Leu
    370                 375                 380
Ser Ile Ala Asp Asp Tyr Leu Lys His Gln Glu Ser Ile Ser Leu Gln
385                 390                 395                 400
Met Gln Leu Leu Gln Gly Val Lys Asn Ile Thr Glu Gln Ala Ile Leu
                405                 410                 415
Ser Ala Val Ser Ile Asn Leu Leu Val Leu Ala Gly Ile Thr Ala Tyr
            420                 425                 430
Gln Ser Ser Thr Val Ala Ala Ala Leu Ser Gln Val Leu Glu Ala Phe
        435                 440                 445
Leu Gln Gly Lys Ser Leu Thr Leu Gly Ala Gly Asn Leu Pro Asp Tyr
    450                 455                 460
Leu Phe Asp Phe Phe Asp His Leu Pro Glu Ser Ala Ser Ala Leu Asp
465                 470                 475                 480
Ser Ile Lys Leu Ser Ile Arg Gly Gly Ala Thr Ala Ser Arg Ala Lys
                485                 490                 495
Ala Ala Val Leu Thr Gly Gly Ile Asp Lys Ser Glu Ala Pro Thr Ile
            500                 505                 510
Asp Glu Thr Tyr Ile Pro Ala Ser Ala Val Ser Leu Phe Asn Glu Trp
        515                 520                 525
Glu Gln Glu Leu Ala Thr Leu Glu Val Thr Val Lys Ser Phe Ser Asp
    530                 535                 540
Leu Asn Lys Gln Ala Ile Thr Asp Leu Gly Thr Gly Phe Ser Ser Ala
545                 550                 555                 560
Ser Ser Leu Gln Leu Gln Ile Lys Arg Cys Ala Gly Val Ala Gly Ser
                565                 570                 575
Leu Ser Leu Val Leu Ser Thr Cys Lys Asn Ile Tyr Ser Leu Glu Val
            580                 585                 590
Asp Ala Ser Asp Leu Thr Val Val Gly Glu Asp His Leu Thr Ile Val
        595                 600                 605
Thr Asn Leu Thr Val Leu Ser Ile His Asp Leu Ala Ser Gln Arg Leu
    610                 615                 620
Glu Gly Gly Leu Thr Asp Ser Leu Gly Asn Leu Lys Gly Leu Ile Glu
```

```
                625                 630                 635                 640
Leu Ile Arg Asp Ala Leu Glu Leu Ser Glu Ala Ser Ala Ile Lys Leu
                    645                 650                 655
Ala Glu Gly Leu Lys Asn Leu Lys Lys Met Cys Leu Ile Ser Leu Leu
                660                 665                 670
Glu Leu Ser Ala Ala Gly Glu Gly Leu Leu Leu Ile Val Lys Ser Leu
            675                 680                 685
Ser Ser Glu Pro Cys Asp Leu Glu Glu Ile Gln Leu Val Ser Cys Cys
        690                 695                 700
Leu Val Ala Gly Ala Val Gln Ile Leu Ala Gln Ile Leu His Asn Leu
705                 710                 715                 720
Val Lys Leu Ser Ile Leu Asp Leu Ser Glu Leu Ser Val Asp Leu Asp
                    725                 730                 735
Gly Asn Ile Ala Val His Ser Val Ile Pro Asp Glu Phe Asn Val Leu
                740                 745                 750
Glu Gln Leu Thr Ala Leu Leu Leu Gln Ile Gly Ala Asp Val Asp Gly
            755                 760                 765
Ser Leu Ser Ser Leu Val Ala Ser Leu Glu Glu Val Ile Ser Leu Val
        770                 775                 780
Ile Leu Gly Leu Glu Gly Gln Gln Leu Thr Asp Thr Glu Ile Ser Ile
785                 790                 795                 800
Leu Gly Ala Phe Ile Gly Leu Gly Ser Leu Ser Asn Leu Glu Glu Leu
                    805                 810                 815
Ile Leu Ala Gly Gly Asp Val Ser Ser Asp Gly Trp Leu Ala Phe Met
                820                 825                 830
Gly Val Phe Glu Val Ala Lys Leu Leu Val Phe Phe Asp Phe Ser Thr
            835                 840                 845
Lys Glu Phe Leu Pro Asp Pro Ala Leu Val Gln Gln Leu Ser Gln Val
        850                 855                 860
Leu Ser Val Leu Ser Phe Leu Gln Thr Ala Arg Leu Val Gly Trp Gln
865                 870                 875                 880
Leu Asp Asp Asp Ser Val Val Val Ile Thr Gly Ala Phe Lys Leu Val
                    885                 890                 895
Thr Gly

<210> SEQ ID NO 12
<211> LENGTH: 3615
<212> TYPE: DNA
<213> ORGANISM: Homo sapiens

<400> SEQUENCE: 12
ctaggaggca agagatctga attccagttc tgatgctgcc actgtgtaag gaagtagttt      60 tataaacccat gggcaaatca tctgagcttt ctcatctgta ataacactga gatcatcatc    120
atcaaattgc cacccaacaa gcctagcttt tgcagaaaa gttaacttgg ataacacttg      180
gctaagtttt ctgactaatg ctggatcagg tagaaattct ttagtactaa agtcaaaaaa    240
cactaattgc ttaagattct caaatacacc catgaaggca agccatccat cactgctcac    300
acgatttccc gccaaattca actgctggaa gttttttcaga gggttctttc caaaaaatgc    360
acctaaaatt ctaatctctg tatctgtgag tctccagttt ttcaacccaa gcttgacgag    420
ttgtgggacc tcctccaaat gtttcaacag gctgctcagg ctgccttgca cgtcacagcc    480
ccagggcagc atcagtgcgg tgagctgttc tagcacgttc atcctgtcga tcagttcatg    540
aagagcttca tttccatctt tttccaggta attttctgat aaatcaagaa tgctcagttt    600
```

```
gaccaaattg tgaagattct gagctaggat tttcactgca tttgcagaca agcagcagga       660
gactaattga atttcttcaa ggtcacaggg ttcacttgac agagacttga ctatgtaatc       720
cattccctct ccaatgtcag acaagtgggt caaatgaaat aaacacatct tcttcaggtt       780
tttcaggcct tcagctagtt ttatagcatc ttcttcattc atctttatgt tatccattat       840
gagctttgta aggttcttca agttacccaa gctgtcagtc agaccacccg gcagccgttg       900
attctgtagg tcatgaatac tcaaggtttt caggtttgtt acagatgtga tgtgcctctc       960
atcttctatg gtgagtggac tggcttccac catgagagaa taaatgttct tacaggtgct      1020
gaggaccaaa ctgaggcttc cagccacacc agcacatctc tttatttgca gcctgaggct      1080
tgtggcagag ctgaatattt tccccagata tctgatatct tgcttattca acttgctgaa      1140
atcccggagt gtgacctcca gagtcctgaa ttcctgcttc cagttgaaga acaaagatac      1200
agccctgctg ggaatgtagg tttctggggc ctcttccatg tggattccac ctgtgtcttc      1260
tgcagccttt tcccatgaag ccatagctcc cccataaaag tccagtttaa tgaagtccag      1320
ggcacttgca caattgggca aatgttcaaa gaagtcaaat aagtaatcgg gatgttccc      1380 tgagttgata tataagcttt taccttgaaa gaaagcttca aattcttggc tcagggctga      1440
tttggatgta ctctcttgat ataaatggat gccacactct acaaaggaat tgatgtttat      1500
ggctttcaga atttcttgct cagtggtgtt tttcacactt tgcaaagatt cctgtctcca      1560
gagaggcctc ttggcgatgg aaagtccgag aaggcagccg tgttgataca ctgctgcgag      1620
gtgcttcata acagccctgg tggcttccac agatgaccca caggtgtacc ggagcaggct      1680
gctataagtg gatgtaatgt ccgaaatgga aaccattttc tgcaagtaac cattcccctt      1740
ggtcacctcc tctggctcat gagacgtcaa taaactgctg agtcttcgtc ctgctgtgta      1800
ctcctggaat gacttgtgaa agaatttata ctttggcttg aacctttgag ctgtatattt      1860
acagaggagc ccagttgtca gcaggacatc ctcattcacg ctggacacat cctgcagttc      1920
gaaatcaaac ttgtgggaga acacaccctc cagagctagg tctccacagt ggtccaggct      1980
ccgaatgaag tcacttgcag ccacaccttt atgtttgtgt tgtttttct gtatcaacag       2040 atcatagaag gtatggaaca gcgttgtttg tgtgtgagag tggaactcac tttcacccat      2100
ctggattgca caagtgatga ccacaaagag aggggtcttc atgagattcc tcaagcacct      2160
ggatttctga atttggagca acaagccttc agcaagctcc ttgatcagca cttctcggat      2220
gagagcctgg gcgctgtctt ctgtcatatc ccccacctca gcagtcaggg caccaaactg      2280
ccgtatgtgc ctcaggcact cagtggtagt ggtgacgatg accatgttct tgaagcggtg      2340
gttttccttt atcagggctt cgatttctgg gcagttctgg ggcttgaatt cattgtagcc      2400
atcaagaagg aaaagaaccc tctgccgcag cttcagcagc atggccatga atgtctgctt      2460
cctgattgtg ccaggtatat ccaggagttg atcacagagg gtttcaaaaa gtccaccctg      2520
ggccctgctg agacggagga agaagacgaa tttgaacttg gtcagagcct tgcactttcc      2580
ggagccccag agcatggcaa ttcgctgcag cagagtggac ttgcctttgc cagattcccc      2640
ttcaatgatg caggggctct gaagagcctg caggaggcca ttcagggtca gctgctccac      2700
gcggtgatgg tgttggtcct tcctccacag gacaggttct gtgaaggtgc ttttcaagtt      2760
aaaaataatg tcaatatctt caccaagggg ataaaagttc agaaaagatg gggtatggta      2820
caagtccttt aaatcctgag ccaaatcgtc caagtctcct tctgatgtct gatgaaaaag      2880
acctattaga agagagtga tgttaaagaa gacccaattc tgtgtctcct caaaactttg      2940
```

| | | | | | |
|---|---|---|---|---|---|
| tccattcaag | tcctgaaata | gaggatagtt | ccactcctta | agggatttaa | gaaagaggtt | 3000 |
| acaggactct | gaacccttt | tcaaaatcat | gtgaatgatc | cctctagcag | catcctgctc | 3060 |
| caccttctcg | cagcaaatga | tgtttacttc | ttcgcgattc | agaacattcc | atacaaatag | 3120 |
| gtcatctgtg | atttgcttta | taacagtcat | tcccattctt | tgaataaggg | ctcggctatt | 3180 |
| gtcctttatg | aaattcacct | ccaggccaaa | ctccgagtcg | ttcctctggt | ggatggcctg | 3240 |
| ctggcgtgcc | gatgtctgtt | gtgtgctctt | ccgccagcat | tctcccttca | acgtcctctg | 3300 |
| gacgtccagc | tgcttgtatg | ttcttccgcc | gatgtgttcc | tctcgacgtc | cagccgcttg | 3360 |
| tgtgtctgcc | tgcaagggtc | tctggctgag | caatccaatt | gccctcttct | tgggagacca | 3420 |
| agacatgttt | ttaaaataaa | gtttctttgt | atttgctttc | cgtttcagtg | aggcctcgag | 3480 |
| ttcttgtaga | ccagatacct | tcttgttctg | tgggtgtttc | tcgttaggtg | gaacgagaga | 3540 |
| cttggaaaag | aaaaagacac | agagacaaag | tatagagaaa | gaaataaggg | agcccagggg | 3600 |
| accagcgttc | agcat | | | | | 3615 |

MOLECULES OF THE CARD-RELATED PROTEIN FAMILY AND USES THEREOF

RELATED APPLICATION INFORMATION

This application claims priority from provisional application Ser. No. 60/161,822, filed Oct. 27, 1999. The entire content of this application is herein incorporated by reference.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as *C. elegans*, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Apoptotic signaling is dependent on protein—protein interactions. At least three different protein—protein interaction domains, the death domain, the death effector domain and the caspase recruitment domain (CARD), have been identified within proteins involved in apoptosis. A fourth protein—protein interaction domain, the death recruiting domain (DRD) was recently identified in murine FLASH (Imai et al. (1999) *Nature* 398:777–85).

Caspases comprise a multi-gene family having at least 12 distinct family members (Nicholson (1999) *Cell Death and Differentiation* 6:1028). A relatively small fraction of cellular polypeptides (less than 200) are thought to serve as targets for cleavage by caspases. Because many of these caspase targets perform key cellular functions, their proteolysis is thought to account for the cellular and morphological events that occur during apoptosis. Members of the caspase gene family can be divided by phylogenetic analysis into two major subfamilies, based upon their relatedness to ICE (interleukin-1β converting enzyme; caspase-1) and CED-3. Alternate groupings of caspases can be made based upon their substrate specificities.

Many caspases and proteins that interact with caspases possess a CARD domain. Hofmann et al. ((1997) *TIBS* 22:155) and others have postulated that certain apoptotic proteins bind to each other via their CARD domains and that different subtypes of CARD domains may confer binding specificity, regulating the activity of various caspases, for example.

CARD-4 is a member of the CED-4/Apaf-1 family that interacts with RICK, a serine threonine kinase, and induces NF-κB via the signaling protein TRAF-6 and NIK (Bertin et al. (1999) *J. Biol. Chem.* 274:12955). CARD-4 includes domains that are similar to the nucleotide binding site domain (NBS) and leucine rich repeat (LRR) domains found in plant R proteins that mediate resistance to pathogens.

SUMMARY OF THE INVENTION

The invention features nucleic acid molecules encoding human CARD-12. CARD-12 has a CARD domain, a nucleotide binding site (NBS) domain, and a leucine rich repeat (LRR) domain. These domains are found in a number of proteins that transmit signals that activate apoptotic and inflammatory pathways in response to stress and other stimuli. Upon activation, CARD-12, like Apaf-1 (Zou et al. (1997) *Cell* 90:405–413), likely binds a nucleotide, allowing CARD-12 to bind to and activate a CARD-containing protein via a CARD—CARD interaction, leading to modulation of apoptosis.

CARD-12 nucleic acids and polypeptides, as well as modulators of CARD-12 activity or expression, are expected to be useful in the modulation of stress-related, apoptotic and inflammatory responses, e.g., for the treatment of apoptotic and inflammatory disorders. In addition, CARD-12 nucleic acids and polypeptides are expected to be useful in the diagnosis of apoptotic and inflammatory disorders as well as in screening assays which can be used to identify compounds which can be used to modulate stress-related, apoptotic and inflammatory responses.

Many cytoplasmic plant proteins involved in response to plant pathogens, generally referred to as "R" proteins, have both an NBS domain and an LRR domain (van der Bizen and Jones (1999) *Current Biology* 8:226–228). R proteins are involved in both a rapid defense response (hypersensitive response) and more long-term nonspecific resistance (systemic acquired resistance). The hypersensitive response involves cell and tissue death that is localized to the site of infection. The LRR domains of R proteins are believed to recognize and bind to pathogen proteins, triggering defensive responses. Many R proteins have an amino terminal effector domain (e.g., a TIR domain or a leucine zipper domain) that is thought to play a role in downstream signaling of events triggered by infection and, possibly, other stresses.

The R proteins have some structural similarity to APAF-1, a protein which mediates between Bcl-2, a negative regulator of apoptosis, and caspases. A domain, designated the NB-ARC domain ("nucleotide-binding adaptor shared by APAF-1, certain R gene products and CED-4") contains a series of motifs and residues that are conserved among R proteins and APAF-1 (van der Bizen and Jones (1999) Current Biology 8:226–228). In addition to the NBS domain, APAF-1 has a CARD domain, functionally analogous to the effector domain of R proteins, and a WD-40 domain, functionally analogous to the LRR domain of R proteins.

Similar to CARD-12, CARD-4 and CARD-7 have both an NBS domain and an LRR domain as well as a CARD domain (detailed information concerning CARD-4 and CARD-7 can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, and U.S. application Ser. No. 09/428,252, filed Oct. 27, 1999, all of which are incorporated herein by reference). The CARD domain, which is present in a number of apoptotic signaling molecules, is an effector domain that thought to be involved in homophilic protein—protein interactions, e.g., with downstream CARD-containing signaling molecules. For example, the CARD domain of CARD-4 interacts with the CARD domain of RICK (RIP2, CARDIAK), a serine-threonine kinase that activates NF-κB signaling pathways.

Other proteins structurally related to CARD-12 include NBS-1, Pyrin-1, PCD-1, PCD-2, and PCD-3.

NBS-1 has an NBS domain and a LRR domain, as well as a pyrin domain. Functionally analogous to the CARD domain of CARD-4, CARD-7, and CARD-12, the pyrin domain is an effector domain thought to be involved in homophilic protein—protein interactions. Pyrin-1 also contains a pyrin domain. Detailed information concerning NBS-1 and Pyrin-1 can be found in U.S. application Ser. No. 09/506,067, filed Feb. 17, 2000, which is incorporated herein by reference.

PCD-1, PCD-2, and PCD-3 each contain both an NBS domain and a leucine zipper domain. A leucine zipper domain, like the CARD domain and the pyrin domain, is an effector domain thought to be involved in homophilic protein—protein interactions. PCD-2 and PCD-3 also each contains LRR domains. PCD-1, which is truncated at is carboxy terminus, is also expected to contain an LRR domain. Detailed information concerning PCD-1, PCD-2, and PCD-3 can be found in U.S. application Ser. No. 09/563,876, filed May 3, 2000, which is incorporated herein by reference.

In general, an NBS domain includes a kinase 1a domain (P-loop), and a kinase 2 domain (Walker B box). An LRR domain usually is composed of several leucine rich repeats.

Without being bound by a particular theory, it is possible that CARD-12 participates in the network of interactions that lead to caspase activity. Human CARD-12 may play a functional role in caspase activation similar to that of Apaf-1 (Zou et al., Cell, 90:405–413, 1997). For example, upon activation, CARD-12 might bind a nucleotide, thus allowing CARD-12 to bind and activate a CARD-containing caspase via a CARD—CARD interaction, leading to apoptotic death of the cell.

Accordingly, CARD-12 molecules are useful as modulating agents in regulating a variety of cellular processes including cell growth and cell death. In one aspect, this invention provides isolated nucleic acid molecules encoding CARD-12 proteins or biologically active portions thereof, as well as nucleic acid fragments suitable as primers or hybridization probes for the detection of CARD-12 encoding nucleic acids.

The invention encompasses methods of diagnosing and treating patients who are suffering from a disorder associated with an abnormal level or rate (undesirably high or undesirably low) of apoptotic cell death, abnormal activity of stress-related pathways of the endoplasmic reticulum (ER), abnormal activity of the Fas/APO-1 receptor complex, abnormal activity of the TNF receptor complex, or abnormal activity of a caspase by administering a compound that modulates the expression of CARD-12 (at the DNA, mRNA or protein level, e.g., by altering mRNA splicing) or by altering the activity of CARD-12. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. CARD-12 and compounds that modulate the expression or activity of CARD-12 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, an autoimmune disorder can be caused by an undesirably low level of apoptosis. Accordingly, CARD-12 and modulators of CARD-12 activity or expression can be used to treat autoimmune disorders (e.g., systemic lupus erythematosis, immune-mediated glomerulonephritis, and arthritis).

Many diseases are associated with an undesirably high rate of apoptosis. CARD-12 and modulators of CARD-12 expression or activity can be used to treat or diagnose such disorders. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, Huntington's disease, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. Additional diseases associated with an undesirably high rate of apoptosis include: ischemic and hypoxic brain injury, traumatic and excitotoxic brain damage, neuronal transplantation, acute bacterial meningitis, kidney ischemia/reperfusion injury, and liver disease. CARD-12 and modulators of CARD-12 may therefore be useful in treating and diagnosing these conditions.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

CARD-12 polypeptides, nucleic acids and modulators of CARD-12 expression or activity can be used to treat inflammatory disorders and immune system disorders. The inflammatory and immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Ischemia is often accompanied by inflammation that causes cell death. Because CARD-12 is expected to play a role in stress-related response, inflammation and apoptosis, CARD-12 polypeptides, nucleic acids, and modulators of CARD-12 expression or activity can be used to treat cells death accompanying inflammatory responses triggered by ischemia.

Invasive infection with Gram-negative bacteria and Gram-positive bacteria often results in septic shock. CARD-12 may recognize and bind components of Gram-negative bacteria and Gram-positive bacteria or other infectious agents (e.g., intracellular parasites), triggering an inflammatory response. Thus, CARD-12 may play a role in innate immune system responses that is similar to that of Toll-like receptor 2 (TLR2), a receptor which has some structural similarity to plant R proteins and IL-1R. TLR2 is a signaling receptor that, in association with CD14, is activated by LPS in a response that requires LPS-binding protein. The interaction of TLR2 with LPS leads to TLR2 oligomerization and recruitment of IRAK (Yang et al. (1998) Nature 395:284–88; Yang et al (1999) J. Immunol. 163:639–43; and Yoshimura et al. (1999) J. Immunol. 163:105). Thus, TLR2 is thought to be a direct mediator of signaling by LPS. TLR2 is also thought to mediate cell activation induced by peptidoglycan and lipoteichoic acid, the main stimulatory components of Gram-positive bacteria (Schwandner et al. (1999) J. Biol. Chem. 274:17406–09).

In addition to the aforementioned disorders, CARD-12 polypeptides, nucleic acids, and modulators of CARD-12 expression or activity can be used to treat septic shock and other disorders associated with an innate immune response. For example, CARD-12 may bind to a component of an intracellular infectious agent or a component of an infectious agent that is brought into a cell expressing CARD-12, e.g., a component that enters a cell through a receptor or is expressed by a viral gene.

In addition to the aforementioned disorders, CARD-12 polypeptides, nucleic acids, and modulators of CARD-12 expression or activity can be used to treat disorders of cell signaling and disorders of tissues in which CARD-12 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, or a complement thereof.

The invention features a nucleic acid molecule which includes a fragment of at least 150 (300, 325, 350, 375, 400, 425, 450, 500, 550, 600, 650, 700, 800, 900, 1000, 1300, 1600, 1900, 2100, 2400, 2700, 3000, or 3100) nucleotides of the nucleotide sequence shown in SEQ ID NO: 1, or SEQ ID NO:3, or a complement thereof.

In an embodiment, a CARD-12 nucleic acid molecule has the nucleotide sequence shown in SEQ ID NO:1 or SEQ ID NO:3.

Also within the invention is a nucleic acid molecule which encodes a fragment of a polypeptide having the amino acid sequence of SEQ ID NO:2.

The invention includes a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 or SEQ ID NO:3 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:3 under stringent conditions (e.g., hybridization in 6× sodium chloride/sodium citrate (SSC) at about 60° C., followed by one or more washes in 0.2× SSC, 0.1% SDS at 65° C.), and wherein the nucleic acid encodes a polypeptide of 1020–1028 amino acids in length, preferably 1024 amino acids, having a molecular weight of about 116.1 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-12 protein having an amino acid sequence that is at least about 65%, preferably 75%, 85%, 95%, or 98% identical to the amino acid sequence of SEQ ID NO:2; an isolated CARD-12 protein having an amino acid sequence that is at least about 85%, 95%, or 98% identical to the P-loop domain of SEQ ID NO:2 (e.g., about amino acid residues 169 to 179 of SEQ ID NO:2); an isolated CARD-12 protein having an amino acid sequence that is at least about 85%, 95%, or 98% identical to the CARD domain of SEQ ID NO:2 (e.g., about amino acid residues 1 to 88 of SEQ ID NO:2); an isolated CARD-12 protein having an amino acid sequence that is at least about 65%, preferably 75%, 85%, 95%, or 98% identical to the nucleotide binding site core domain of SEQ ID NO:2 (e.g., about amino acid residues 161 to 323 of SEQ ID NO:2); an isolated CARD-12 protein having an amino acid sequence that is at least about 65%, preferably 75%, 85%, 95%, or 98% identical to one or more of the leucine rich repeats of SEQ ID NO:2 (e.g., about amino acids residues 762–789, 819–846, 847–874, and 938–965 of SEQ ID NO:2); and an isolated CARD-12 protein having an amino acid sequence that is at least about 85%, 95%, or 98% identical to the NAIP homology region of SEQ ID NO:2 (e.g., about amino acid residues 150 to 1024 of SEQ ID NO:2).

Also within the invention are: an isolated CARD-12 protein which is encoded by a nucleic acid molecule having a nucleotide sequence that is at least about 65%, preferably 75%, 85%, or 95% identical to SEQ ID NO:3; an isolated CARD-12 protein which is encoded by a nucleic acid molecule having a nucleotide sequence at least about 85%, 95%, or 98% identical to the P-loop domain encoding portion of SEQ ID NO:3; an isolated CARD-12 protein which is encoded by a nucleic acid molecule having a nucleotide sequence at least about 65% preferably 75%, 85%, or 95% identical the CARD domain encoding portion of SEQ ID NO:3; an isolated CARD-12 protein which is encoded by a nucleic acid molecule having a nucleotide sequence at least about 65% preferably 75%, 85%, or 95% identical the NAIP homology encoding portion of SEQ ID NO:3; an isolated CARD-12 protein which is encoded by a nucleic acid molecule having a nucleotide sequence at least about 65% preferably 75%, 85%, or 95% identical the nucleotide binding site domain encoding portion of SEQ ID NO:3; an isolated CARD-12 protein which is encoded by a nucleic acid molecule having a nucleotide sequence at least about 65% preferably 75%, 85%, or 95% identical to the LRR domain encoding portion of SEQ ID NO:3 or one or more leucine rich repeat encoding portions of SEQ ID NO:3; and an isolated CARD-12 protein which is encoded by a nucleic acid molecule having a nucleotide sequence which hybridizes under stringent hybridization conditions to a nucleic acid molecule having the nucleotide sequence of SEQ ID NO:3.

The CARD-12 nucleic acids, polypeptides, and antibodies of the invention may be useful for mapping the location of the CARD-12 gene.

Another embodiment of the invention features CARD-12 nucleic acid molecules which specifically detect CARD-12 nucleic acid molecules, relative to nucleic acid molecules encoding other members of the CARD superfamily and/or members of the NBS/LRR superfamily. For example, in one embodiment, a CARD-12 nucleic acid molecule hybridizes under stringent conditions to a nucleic acid molecule comprising the nucleotide sequence of SEQ ID NO:1, SEQ ID NO:3, or a complement thereof. In another embodiment, the CARD-12 nucleic acid molecule is at least 300 (350, 400, 450, 500, 550, 600, 650, 700, 800, 900, 1000, 1300, 1600, 1900, 2100, 2400, 2700, 3000, or 3100) nucleotides in length and hybridizes under stringent conditions to a nucleic acid molecule comprising the nucleotide sequence shown in SEQ ID NO:1, SEQ ID NO:3, or a complement thereof. In another embodiment, an isolated CARD-12 nucleic acid molecule comprises the CARD domain encoding portion of SEQ ID NO:3, or a complement thereof. In yet another embodiment, the invention provides an isolated nucleic acid molecule which is antisense to the coding strand of a CARD-12 nucleic acid.

Another aspect of the invention provides a vector, e.g., a recombinant expression vector, comprising a CARD-12 nucleic acid molecule of the invention. In another embodiment the invention provides a host cell containing such a vector. The invention also provides a method for producing CARD-12 protein by culturing, in a suitable medium, a host cell of the invention containing a recombinant expression vector such that a CARD-12 protein is produced.

Another aspect of this invention features isolated or recombinant CARD-12 proteins and polypeptides. Preferred CARD-12 proteins and polypeptides possess at least one biological activity possessed by naturally occurring human CARD-12, e.g., (1) the ability to form protein:protein interactions with proteins in the apoptotic signaling pathway; (2) the ability to form CARD—CARD interactions with proteins in the apoptotic signaling pathway; (3) the ability to bind a CARD-12 ligand; and (4) the ability to bind to an intracellular target. Other activities include: (1) modulation of cellular proliferation; (2) modulation of cellular differentiation; (3) modulation of cellular death; (4) modulation of ER-specific apoptosis pathways; (5) modulation of the NF-kB pathway; (6) modulation of stress-responsive signaling pathways; and (7) modulation of an innate immune response.

The CARD-12 proteins of the present invention, or biologically active portions thereof, can be operatively linked to a non-CARD-12 polypeptide (e.g., heterologous amino acid sequences) to form CARD-12 fusion proteins, respectively. The invention further features antibodies that specifically bind CARD-12 proteins, such as monoclonal or polyclonal antibodies. In addition, the CARD-12 proteins or biologically active portions thereof can be incorporated into pharmaceutical compositions, which optionally include pharmaceutically acceptable carriers.

In another aspect, the present invention provides a method for detecting the presence of CARD-12 activity or expression in a biological sample by contacting the biological sample with an agent capable of detecting an indicator of CARD-12 activity such that the presence of CARD-12 activity is detected in the biological sample.

In another aspect, the invention provides a method for modulating CARD-12 activity comprising contacting a cell with an agent that modulates (inhibits or stimulates) CARD-12 activity or expression such that CARD-12 activity or expression in the cell is modulated. In one embodiment, the agent is an antibody that specifically binds to CARD-12 protein. In another embodiment, the agent modulates expression of CARD-12 by modulating transcription of a CARD-12 gene, splicing of a CARD-12 mRNA, or translation of a CARD-12 mRNA. In yet another embodiment, the agent is a nucleic acid molecule having a nucleotide sequence that is antisense to the coding strand of the CARD-12 mRNA or the CARD-12 gene.

In one embodiment, the methods of the present invention are used to treat a subject having a disorder characterized by aberrant CARD-12 protein or nucleic acid expression or activity or related to CARD-12 expression or activity by administering an agent which is a CARD-12 modulator to the subject. In one embodiment, the CARD-12 modulator is a CARD-12 protein. In another embodiment the CARD-12 modulator is a CARD-12 nucleic acid molecule. In other embodiments, the CARD-12 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-12 protein; (ii) mis-regulation of a gene encoding a CARD-12 protein; (iii) aberrant RNA splicing; and (iv) aberrant post-translational modification of a CARD-12 protein, wherein a wild-type form of the gene encodes a protein with a CARD-12 activity.

In another aspect, the invention provides a method for identifying a compound that binds to or modulates the activity of a CARD-12 protein. In general, such methods entail measuring a biological activity of a CARD-12 protein in the presence and absence of a test compound and identifying those compounds which alter the activity of the CARD-12 protein.

The invention also features methods for identifying a compound which modulates the expression of CARD-12 by measuring the expression of CARD-12 in the presence and absence of a compound.

The invention also features methods for treating disorders associated with inappropriate apoptosis (e.g., Alzheimer's diseases or other neurological disorders associated with neuronal apoptosis) by modulating the expression or activity of CARD-12.

Other features and advantages of the invention will be apparent from the following detailed description and claims.

BRIEF DESCRIPTION OF THE DRAWINGS

FIGS. 1A–1E depict the cDNA sequence (SEQ ID NO:1) and predicted amino acid sequence (SEQ ID NO:2) of human CARD-12. The open reading frame of CARD-12 (SEQ ID NO:1) extends from nucleotide 36 to nucleotide 3107 of SEQ ID NO:1 (SEQ ID NO:3).

FIGS. 2A–2E depict a predicted nucleotide sequence (SEQ ID NO:4) and predicted amino acid sequence (SEQ ID NO:5) of human CARD-12, based upon the CARD-12 sequence derived from a genomic clone. The nucleotide sequence depicted as complementary to SEQ ID NO:4 is SEQ ID NO:12.

FIG. 5A depicts an alignment of amino acids 2–88 of human CARD-12 (amino acid residues 2–88 of SEQ ID NO:2) with a CARD domain (SEQ ID NO:7) derived from a hidden Markov model.

FIG. 5B depicts an alignment of amino acids 764–791 of human CARD-12 (amino acid residues 764–791 of SEQ ID NO:2) with a consensus leucine rich repeat (SEQ ID NO:8) derived from a hidden Markov model.

FIG. 5C depicts an alignment of amino acids 821–848 of human CARD-12 (amino acid residues 821–848 of SEQ ID NO:2) with a consensus leucine rich repeat (SEQ ID NO:8) derived from a hidden Markov model.

FIG. 5D depicts an alignment of amino acids 849–872 of human CARD-12 (amino acid residues 849–872 of SEQ ID NO:2) with a consensus leucine rich repeat (SEQ ID NO:8) derived from a hidden Markov model.

FIG. 5E depicts an alignment of amino acids 938–965 of human CARD-12 (amino acid residues 938–965 of SEQ ID NO:2) with a consensus leucine rich repeat (SEQ ID NO:8) derived from a hidden Markov model.

FIGS. 6A–6C depict an alignment of amino acids 150–1024 of human CARD-12 (amino acid residues 150–1024 of SEQ ID NO:2) with amino acids 451–1232 of neuronal AIP (SEQ ID NO:9). The consensus (SEQ ID NO:10) and majority (SEQ ID NO:11) sequences are depicted above the alignment.

DETAILED DESCRIPTION OF THE INVENTION

Figure 3:
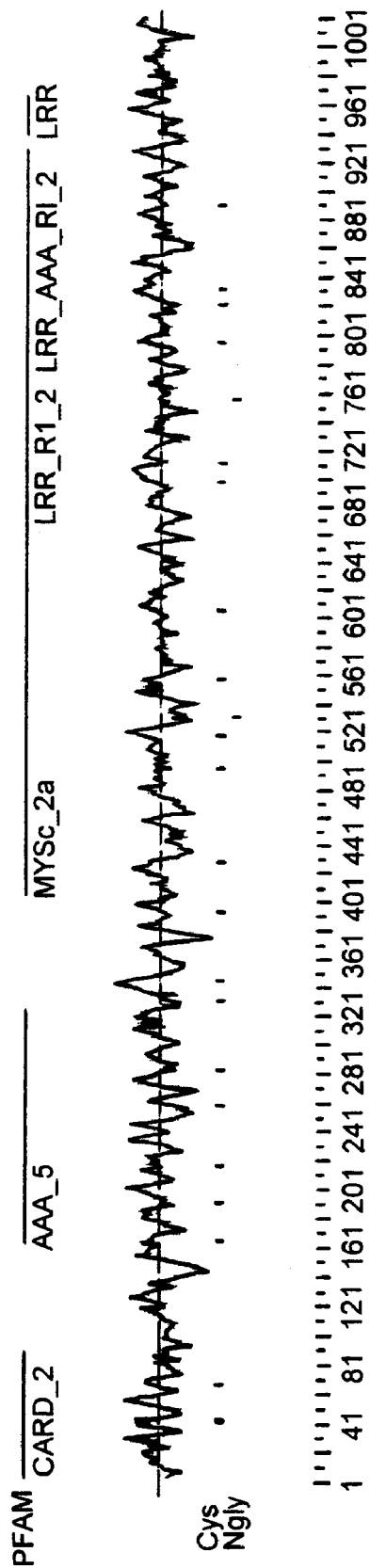
FIG. 3 depicts a hydropathy plot of CARD-12. Relatively hydrophobic residues are above the dashed horizontal line, and relatively hydrophilic residues are below the dashed horizontal line. The cysteine residues (cys) and N-glycosylation (Ngly) site are indicated by short vertical lines just below the hydropathy trace.

The present invention is based, in part, on the identification of a cDNA sequence encoding a human CARD-12 protein. A nucleotide sequence encoding a human CARD-12 protein is shown in FIGS. 1A–1E (SEQ ID NO:1; SEQ ID NO:3 includes the open reading frame only). A predicted amino acid sequence of CARD-12 protein is also shown in FIGS. 1A–1E (SEQ ID NO:2).

A BAC clone (GenBank™ Accession Number AL121653) was searched to identify potential exons. The predicted protein sequences were then searched using a profile of known CARD domains. This search led to the identification of a sequence predicted to encode a CARD domain-containing protein later identified as CARD-12. FIGS. 2A–2E depict a nucleotide sequence (SEQ ID NO:4) assembled from the BAC clone which includes a predicted open reading frame (SEQ ID NO:6; nucleotides 1–3612 of SEQ ID NO:4) encoding a 1204 amino acid protein (SEQ ID NO:5).

The CARD-12 sequence assembled from the BAC clone was used to further characterize the CARD-12 cDNA sequence. A search of a proprietary electronic cDNA database (created from a human lymphocyte library) using sequences derived from the 3' end of SEQ ID NO:4 led to the identification of a cDNA containing the 3' end of the CARD-12 cDNA. The sequence of the 5' end of the CARD-12 cDNA was determined by a search of the Incyte (Palo Alto, Calif.) Life Gold Templates cDNA electronic database using sequences from the 5' end of SEQ ID NO:4. A cDNA sequence was identified (Incyte clone number 328193) that contained 366 nucleotides of the 5' portion of the CARD-12 cDNA. Primers were designed corresponding to the 5' untranslated region and the 3' carboxy terminus coding region of CARD-12. PCR amplification using these primers was performed on a placenta cDNA library. The sequencing of PCR products led to the identification of the cDNA sequence of CARD-12 (SEQ ID NO:1).

The CARD-12 cDNA sequence (SEQ ID NO:1) has some differences compared to that predicted by the assembly of the predicted CARD-12 exons of the BAC clone (SEQ ID NO:4). These differences are generally located at the 5' and 3' end of the cDNA. Where the CARD-12 sequences depicted in SEQ ID NO:1 and SEQ ID NO:4 differ, SEQ ID NO:1 corresponds to the CARD-12 cDNA sequence.

FIGS. 1A–1E depict the sequence of a 3133 nucleotide cDNA (SEQ ID NO:1) which includes a predicted open reading frame (SEQ ID NO:3; nucleotides 36–3107 of SEQ ID NO:1) encoding a 1024 amino acid human CARD-12 protein (SEQ ID NO:2). Human CARD-12 is predicted to be an intracellular protein.

The predicted amino acid sequence of human CARD-12 was compared to amino acid sequences of known proteins and various motifs were identified. The 1024 amino acid human CARD-12 protein includes two N-glycosylation sites (e.g., about amino acid residues 539–542 and 764–767 of SEQ ID NO:2); a glycosaminoglycan attachment site (e.g., about amino acid residues 171–174 of SEQ ID NO:2); four cAMP- and cGMP-dependent protein kinase phosphorylation site (e.g., about amino acid residues 60–63, 228–231, 453–456, and 985–988 of SEQ ID NO:2); 11 protein kinase C phosphorylation sites (e.g., about amino acid residues 72–74, 171–173, 188–190, 226–228, 403–405, 536–538, 566–568, 665–667, 689–691, 710–712, and 973–975 of SEQ ID NO:2); 20 casein kinase II phosphorylation sites (e.g., about amino acid residues 72–75, 94–97, 133–136, 215–218, 279–282, 365–368, 415–418, 445–448, 460–463, 479–482, 497–500, 541–544, 553–556, 607–610, 665–668, 725–728, 742–745, 851–854, 920–923, and 973–976 of SEQ ID NO:2); a tyrosine kinase phosphorylation site (e.g., about amino acid residues 71–78 of SEQ ID NO:2); 15 N-myristoylation sites (e.g., about amino acid residues 62–67, 156–161, 187–192, 211–216, 291–296, 380–385, 516–521, 618–623, 699–704, 754–759, 760–765, 894–899, 928–933, 946–951, and 959–964 of SEQ ID NO:2); an amidation site (e.g., about amino acid residues 451–454 of SEQ ID NO:2); and an ATP/GTP-binding site motif A (P-loop) (e.g., about amino acid residues 169–179 of SEQ ID NO:2).

FIG. 3 depicts a hydropathy plot of CARD-12. Relatively hydrophobic residues are above the dashed horizontal line, and relatively hydrophilic residues are below the dashed horizontal line. The cysteine residues (cys) and N-glycosylation (Ngly) site are indicated by short vertical lines just below the hydropathy trace.

Figure 4:
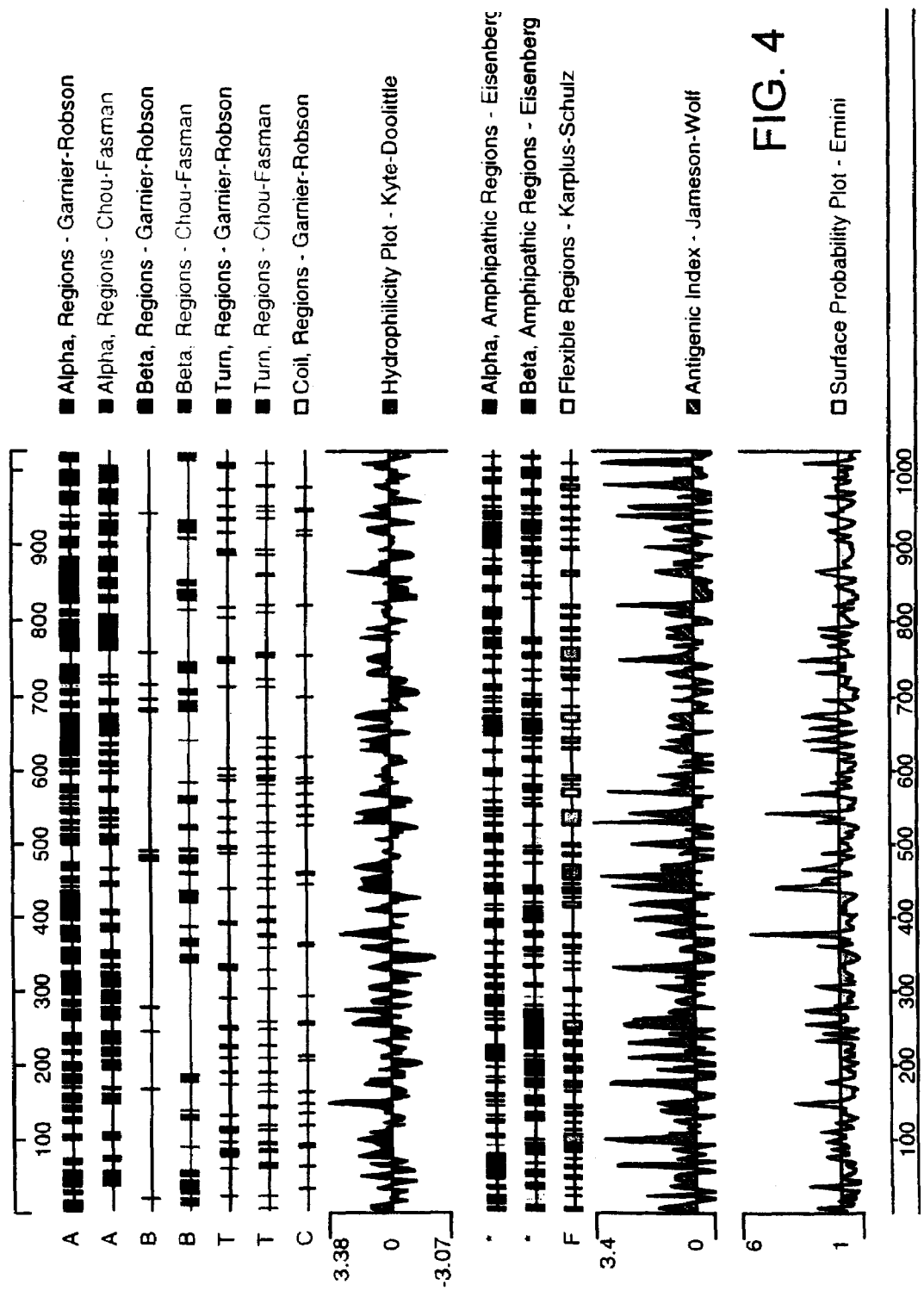
FIG. 4 depicts a plot showing the predicted structural features of CARD-12. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of CARD-12 is presented in FIG. 4. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted CARD-12 amino acid sequence showed it to contain a CARD domain (e.g., about amino acid residues 1–88 of SEQ ID NO:2), a nucleotide binding site (NBS) domain (e.g., about amino acid residues 161–323 of SEQ ID NO:2), and three leucine rich repeats (LRR; e.g., about amino acid residues 762–789, 819–846, 847–874, and 938–965 of SEQ ID NO:2) which form a LRR domain (e.g., about amino acid residues 762–965 of SEQ ID NO:2). Within the predicted NBS domain there is a kinase 1a domain (P-loop) (e.g., about amino acid residues 169–179 of SEQ ID NO:2) and a kinase 2 domains (e.g., about amino acid residues 245–248 of SEQ ID NO:2).

FIG. 5A depicts an alignment of amino acids 2–88 of human CARD-12 (amino acid residues 2–88 of SEQ ID NO:2) with a consensus CARD domain (SEQ ID NO:7) derived from a HMM.

FIGS. 5B–5E each depict an alignment of one of the four leucine rich repeats within the LRR domain of CARD-12 (amino acid residues 764–791 of SEQ ID NO:2 (FIG. 5B), amino acid residues 821–848 of SEQ ID NO:2 (FIG. 5C), amino acid residues 849–872 of SEQ ID NO:2 (FIG. 5D), and amino acid residues 938–965 of SEQ ID NO:2 (FIG. 5E)) with a consensus LRR (SEQ ID NO:8) derived from a HMM.

The domain alignments depicted in FIGS. 5A–5E were identified by homology searching using consensus domains derived from hidden Markov models (HMMs). HMMs can be used to perform multiple sequence alignment and very sensitive database searching, using statistical descriptions of a domain's consensus sequence. In the alignments of FIGS. 5A–5E a single letter amino acid designation at a position on the line between the CARD-12 sequence and the HMM-generated consensus domain sequence indicates an exact match between the two. A "+" in this middle line indicates a conservative substitution at the particular residue of CARD-12. Amino acid residues located in the domains identified by the HMM search may be important for the appropriate functioning of the CARD-12 protein. For this reason, amino acid substitutions with respect to the sequence of SEQ ID NO:2 that are outside of the domains homologous to HMM consensus domains may be less detrimental to the activity of the CARD-12 protein.

Figure 6B:
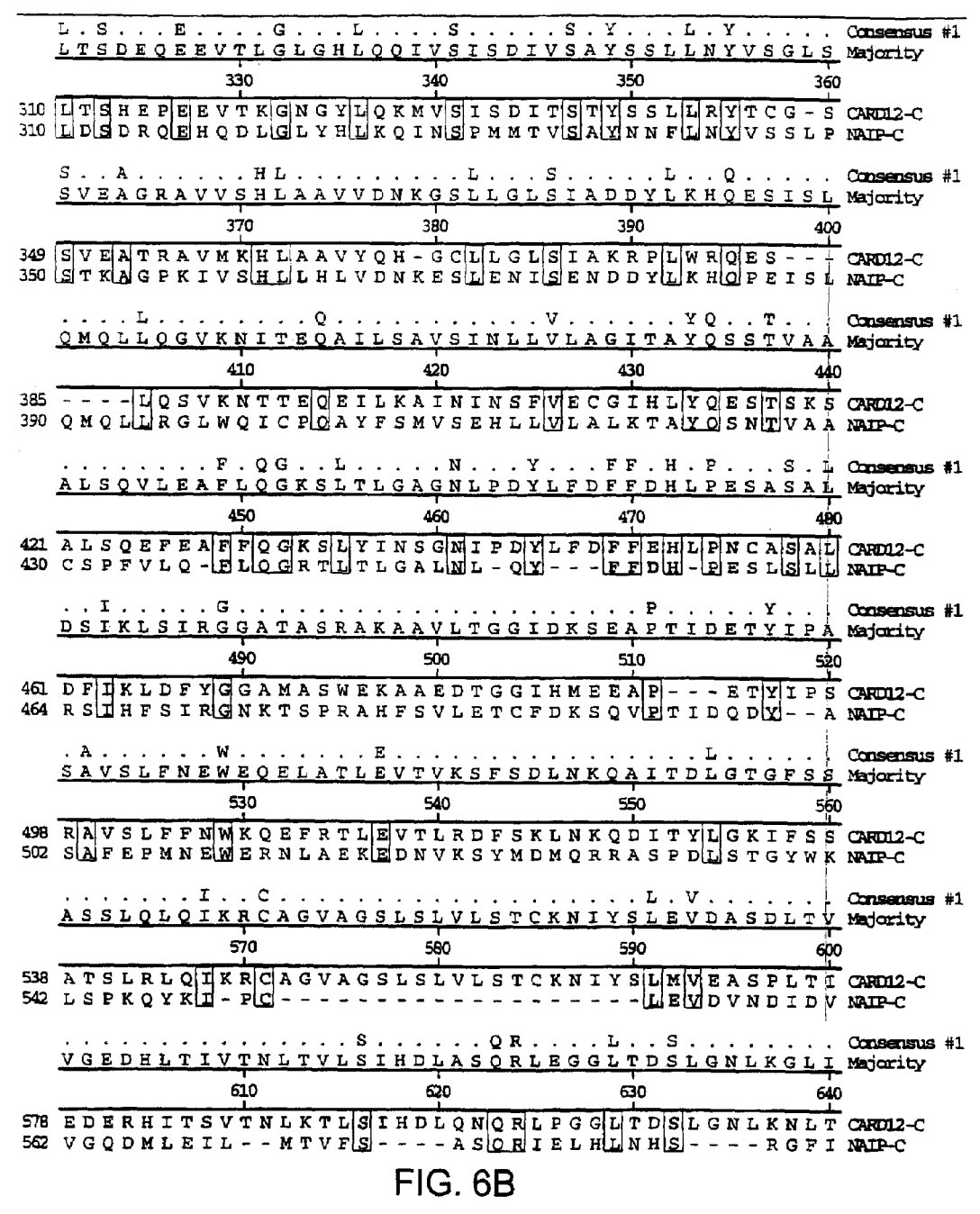

The C-terminal portion of CARD-12 (amino acids 150 to 1024 of SEQ ID NO:2) bears some similarity to the N-terminus of neuronal AIP (GenBank™ Accession Number Q13075; Roy et al. (1995) Cell 80:167–178). FIGS. 6A–6C depict an alignment of amino acids 451–1232 of neuronal AIP (SEQ ID NO:9) and amino acids 150–1024 of human CARD-12.

TABLE 1

Summary of Human CARD-12 Sequence Information

| Source of CARD-12 Sequence | Predicted cDNA | Predicted Protein | Predicted ORF | Figure |
|---|---|---|---|---|
| cDNA sequence | SEQ ID NO:1 | SEQ ID NO:2 | SEQ ID NO:3 | FIGS. 1A–1E |
| genomic sequence | SEQ ID NO:4 | SEQ ID NO:5 | SEQ ID NO:6 | FIGS. 2A–2E |

TABLE 2

Summary of Domains of CARD-12

| Domain | Location in CARD-12 |
|---|---|
| CARD | about amino acids 1–88 of SEQ ID NO:2 |
| NBS | about amino acids 161–323 of SEQ ID NO:2 |
| Kinase 1a domain (P-loop) | about amino acids 169–179 of SEQ ID NO:2 |
| Kinase 2 domain (Walker B box) | about amino acids 245–248 of SEQ ID NO:2 |
| Neuronal AIP Homology | about amino acids 150–1024 of SEQ ID NO:2 |
| Leucine rich repeats | about amino acids 762–789, 819–846, 847–874, and 938–965 of SEQ ID NO:2 |
| LRR | about amino acids 762–965 of SEQ ID NO:2 |

A region, the CARD domain, of human CARD-12 protein (SEQ ID NO:2) bears some similarity to the CARD domains of CARD-3, CARD-4, CARD-5, CARD-6, CARD-7, CARD-8, CARD-9, CARD-10, CARD-11, CARD-13, CARD-14, and CARD-15. Detailed information concerning CARD-3, CARD-4, CARD-5, CARD-6, CARD-7, CARD-8, CARD-9, CARD-10, CARD-11, CARD-13, CARD-14, and CARD-15, can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, U.S. Application Ser. No. 60/180,021, filed Feb. 3, 2000, U.S. application Ser. No. 09/573,641, filed May 17, 2000, U.S. Application Ser. No. 60/181,159 filed Feb. 9, 2000, U.S. Application Ser. No. 60/168,780 filed Dec. 3, 1999, U.S. application Ser. No. 09/507,533 filed Feb. 18, 2000, and U.S. application Ser. No. 09/513,904 filed Feb. 25, 2000. The entire content of each of these applications is incorporated herein by reference.

Human CARD-12 is a member of a family of molecules (the CARD-12 family) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

Preferred CARD-12 polypeptides of the present invention include an amino acid sequence sufficiently identical to one or more of the following domains: a CARD domain, an NBS domain, and a LRR domain.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-12 activity", "biological activity of CARD-12" or "functional activity of CARD-12", refers to an activity exerted by a CARD-12 protein, polypeptide or nucleic acid molecule on a CARD-12 responsive cell as determined in vivo, or in vitro, according to standard techniques. CARD-12 may act as a pro-apoptotic protein or an anti-apoptotic protein (i.e., it might act to decrease or increase apoptosis). A CARD-12 activity can be a direct activity, such as an association with or an enzymatic activity on a second protein or an indirect activity, such as a cellular signaling activity mediated by interaction of the CARD-12 protein with a second protein.

In one embodiment, a CARD-12 activity can include at least one or more of the following activities: (i) the ability to interact with proteins in an apoptotic signaling pathway (ii) the ability to interact with a CARD-12 ligand; or (iii) the ability to interact with an intracellular target protein; (iv) the ability to interact, directly or indirectly with one or more with proteins having a CARD domain, e.g., a caspase or an AIP (e.g., AIP-1 or AIP-2); (v) the ability to modulate the activity of a caspase, e.g., caspase-9; (vi) the ability to modulate the activity of NF-κB; (vii) the ability to modulate Apaf-1; (viii) the ability to interact directly or indirectly with a Bcl-2 family member; (ix) the ability to modulate the activity of a stress activated kinase (e.g., JNK/p38); and (x) the ability to modulate phosphorylation of CHOP (GADD 153). CARD-12 nucleic acid and polypeptides as well as modulators of activity of expression of CARD-12 might be used to modulate an Apaf-1 signaling pathway. CARD-12 may modulate the activity of a neurotrophin receptor and thus modulate apoptosis of neuronal cells. Accordingly, CARD-12 nucleic acids and polypeptides as well as modulators of CARD-12 activity or expression can be used to modulate apoptosis of neurons (e.g., for treatment of neurological disorders, particularly neurodegenerative disorders).

Accordingly, another embodiment of the invention features isolated CARD-12 proteins and polypeptides having a CARD-12 activity.

Various aspects of the invention are described in further detail in the following subsections.

I. Isolated Nucleic Acid Molecules

One aspect of the invention pertains to isolated nucleic acid molecules that encode CARD-12 proteins or biologically active portions thereof, as well as nucleic acid molecules sufficient for use as hybridization probes to identify CARD-12-encoding nucleic acids (e.g., CARD-12 mRNA) and fragments for use as PCR primers for the amplification or mutation of CARD-12 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated CARD-12 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or a complement of any of these nucleotide sequences, can be isolated using standard molecular biology techniques and the sequence information provided herein. Using all or portion of the nucleic acid sequences of SEQ ID NO:1 or SEQ ID NO:3 as a hybridization probe, CARD-12 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-12 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-12, for example, a fragment which can be used as a probe or primer or a fragment encoding a biologically active portion of CARD-12. The nucleotide sequence determined from the cloning of the human CARD-12 gene allows for the generation of probes and primers designed for use in identifying and/or cloning CARD-12 homologues in other cell types, e.g., from other tissues, as well as CARD-12 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1 or SEQ ID NO:3 or of a naturally occurring mutant of one of SEQ ID NO:1 or SEQ ID NO:3.

Probes based on the CARD-12 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-12 proteins of the present invention, identifying cells or tissue which mis-express a CARD-12 protein, such as by measuring a level of a CARD-12-encoding nucleic acid in a sample of cells from a subject, e.g., detecting CARD-12 mRNA levels or determining whether a genomic CARD-12 gene has been mutated or deleted.

A nucleic acid fragment encoding a "biologically active portion" of CARD-12 can be prepared by isolating a portion of SEQ ID NO:1 or SEQ ID NO:3 which encodes a polypeptide having a CARD-12 biological activity, expressing the encoded portion of CARD-12 protein (e.g., by recombinant expression in vitro) and assessing the activity of the encoded portion of CARD-12. For example, a nucleic acid fragment encoding a biologically active portion of CARD-12 includes a CARD domain, e.g., amino acids 1–88 of SEQ ID NO:2.

The invention further encompasses nucleic acid molecules that differ from the nucleotide sequence of SEQ ID NO:1 or SEQ ID NO:3 due to degeneracy of the genetic code and thus encode the same CARD-12 protein as that encoded by the nucleotide sequence shown in SEQ ID NO:1 or SEQ ID NO:3.

In addition to the CARD-12 nucleotide sequence shown in SEQ ID NO:1 and SEQ ID NO:3, it will be appreciated by those skilled in the art that DNA sequence polymorphisms that lead to changes in the amino acid sequences of CARD-12 may exist within a population (e.g., the human population). Such genetic polymorphism in the CARD-12 gene may exist among individuals within a population due to natural allelic variation. As used herein, the terms "gene" and "recombinant gene" refer to nucleic acid molecules comprising an open reading frame encoding a CARD-12 protein, preferably a mammalian CARD-12 protein. Such natural allelic variations can typically result in 1–5% variance in the nucleotide sequence of the CARD-12 gene. Any and all such nucleotide variations and resulting amino acid polymorphisms in CARD-12 that are the result of natural allelic variation and that do not alter the functional activity of CARD-12 are intended to be within the scope of the invention. Thus, e.g., 1%, 2%, 3%, 4%, or 5% of the amino acids in CARD-12 (e.g., 1, 2, 3, 4, 5, 6, 8, 10, 15, or 20 amino acids) are replaced by another amino acid, preferably by conservative substitution.

Moreover, nucleic acid molecules encoding CARD-12 proteins from other species (CARD-12 orthologs/homologues), which have a nucleotide sequence which differs from that of a CARD-12 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1300, 1600, 1900, 2100, 2400, 2700, 3000, or 3100) nucleotides in length and hybridizes under stringent conditions to the nucleic acid molecule comprising the nucleotide sequence, preferably the coding sequence, of SEQ ID NO:1 or SEQ ID NO:3.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2× SSC, 0.1% SDS at 50–65 C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the CARD-12 sequence that may exist in the population, the skilled artisan will further appreciate that changes can be introduced by mutation into the nucleotide sequence of SEQ ID NO:1 or SEQ ID NO:3, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of CARD-12 protein without altering the biological activity, whereas an "essential" amino acid residue is required for biological activity. For example, amino acid residues that are conserved among the CARD-12, proteins of various species are predicted to be particularly unamenable to alteration.

For example, preferred CARD-12 proteins of the present invention contain at least one CARD domain. Additionally, a CARD-12 protein also contains at least one kinase-2 domain, at least one P-loop domain, at least one nucleotide binding site domain, and at least one LRR domain. Such conserved domains are less likely to be amenable to mutation. Other amino acid residues, however, (e.g., those that are not conserved or only semi-conserved among CARD-12 of various species) may not be essential for activity and thus are likely to be amenable to alteration.

Accordingly, another aspect of the invention pertains to nucleic acid molecules encoding CARD-12 proteins that contain changes in amino acid residues that are not essential for activity. Such CARD-12 proteins differ in amino acid sequence from SEQ ID NO:2, and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2. An isolated nucleic acid molecule encoding a CARD-12 protein having a sequence which differs from that of SEQ ID NO:1 or SEQ ID NO:3 can be created by introducing one or more nucleotide substitutions, additions or deletions into the nucleotide sequence of CARD-12 (SEQ ID NO:1 or SEQ ID NO:3) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CARD-12 is preferably replaced with another amino acid residue from the same side chain family. Alternatively, mutations can be introduced randomly along all or part of a CARD-12 coding sequence, such as by saturation mutagenesis, and the resultant mutants can be screened for CARD-12 biological activity to identify mutants that retain activity. Following mutagenesis, the encoded protein can be expressed recombinantly and the activity of the protein can be determined.

In an embodiment, a mutant CARD-12 protein can be assayed for: (1) the ability to form protein:protein interactions with proteins in the apoptotic signaling pathway; (2) the ability to bind a CARD-12 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-12 coding strand, or to only a portion thereof, e.g., all or part of the protein coding region (or open reading frame). An antisense nucleic acid molecule can be antisense to a noncoding region of the coding strand of a nucleotide sequence encoding CARD-12. The noncoding regions ("5' and 3"untranslated regions") are the 5' and 3' sequences that flank the coding region and are not translated into amino acids. Given the coding strand sequences encoding CARD-12 disclosed herein, antisense nucleic acids of the invention can be designed according to the rules of Watson and Crick base pairing. The antisense nucleic acid molecule can be complementary to the entire coding region of CARD-12 mRNA, but more preferably is an oligonucleotide which is antisense to only a portion of the coding or noncoding region of CARD-12 mRNA. For example, the antisense oligonucleotide can be complementary to the region surrounding the translation start site of CARD-12 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-12 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-12 mRNA transcripts to thereby inhibit translation of CARD-12 mRNA. A ribozyme having specificity for a CARD-12-encoding nucleic acid can be designed based upon the nucleotide sequence of a CARD-12 cDNA disclosed herein. For example, a derivative of a Tetrahymena L-19 IVS RNA can be constructed in which the nucleotide sequence of the active site is complementary to the nucleotide sequence to be cleaved in a CARD-12-encoding mRNA. See, e.g., Cech et al. U.S. Pat. No. 4,987,071; and Cech et al. U.S. Pat. No. 5,116,742. Alternatively, CARD-12 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, CARD-12 gene expression can be inhibited by targeting nucleotide sequences complementary to the regulatory region of the CARD-12 (e.g., the CARD-12 promoter and/or enhancers) to form triple helical structures that prevent transcription of the CARD-12 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of CARD-12 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-12 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of CARD-12 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-12 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-12 Proteins and Anti-CARD-12 Antibodies.

One aspect of the invention pertains to isolated CARD-12 proteins, and biologically active portions thereof, as well as polypeptide fragments suitable for use as immunogens to raise anti-CARD-12 antibodies. In one embodiment, native CARD-12 proteins can be isolated from cells or tissue sources by an appropriate purification scheme using standard protein purification techniques. In another embodiment, CARD-12 proteins are produced by recombinant DNA techniques. Alternative to recombinant expression, a CARD-12 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-12 protein is derived, or substantially free from chemical precursors or other chemicals when chemically synthesized. The language "substantially free of cellular material" includes preparations of CARD-12 protein in which the protein is separated from cellular components of the cells from which it is isolated or recombinantly produced. Thus, CARD-12 protein that is substantially free of cellular material includes preparations of CARD-12 protein having less than about 30%, 20%, 10%, or 5% (by dry weight) of non-CARD-12 protein (also referred to herein as a "contaminating protein"). When the CARD-12 protein or biologically active portion thereof is recombinantly produced, it is also preferably substantially free of culture medium, i.e., culture medium represents less than about 20%, 10%, or 5% of the volume of the protein preparation. When CARD-12 protein is produced by chemical synthesis, it is preferably substantially free of chemical precursors or other chemicals, i.e., it is separated from chemical precursors or other chemicals which are involved in the synthesis of the protein. Accordingly such preparations of CARD-12 protein have less than about 30%, 20%, 10%, 5% (by dry weight) of chemical precursors or non-CARD-12 chemicals.

Biologically active portions of a CARD-12 protein include peptides comprising amino acid sequences sufficiently identical to or derived from the amino acid sequence of the CARD-12 protein (e.g., the amino acid sequence shown in SEQ ID NO:2), which include less amino acids than the full length CARD-12 protein, and exhibit at least one activity of a CARD-12 protein. Typically, biologically active portions comprise a domain or motif with at least one activity of the CARD-12 protein. A biologically active portion of a CARD-12 protein can be a polypeptide which is, for example, 10, 25, 50, 100, 150, 200, 250, 300 or more amino acids in length. Preferred biologically active polypeptides include one or more identified CARD-12 structural domains, e.g., the CARD domain (amino acids 1–88 of SEQ ID NO:2).

Moreover, other biologically active portions, in which other regions of the protein are deleted, can be prepared by recombinant techniques and evaluated for one or more of the functional activities of a native CARD-12 protein.

CARD-12 protein has the amino acid sequence shown of SEQ ID NO:2. Other useful CARD-12 proteins are substantially identical to SEQ ID NO:2 and retain the functional activity of the protein of SEQ ID NO:2, yet differ in amino acid sequence due to natural allelic variation or mutagenesis.

A useful CARD-12 protein is a protein which includes an amino acid sequence at least about 45%, preferably 55%, 65%, 75%, 85%, 95%, or 99% identical to the amino acid sequence of SEQ ID NO:2, and retains the functional activity of the CARD-12 protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-12 nucleic acid molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used.

The percent identity between two sequences can be determined using techniques similar to those described above, with or without allowing gaps. In calculating percent identity, typically exact matches are counted.

The invention also provides CARD-12 chimeric or fusion proteins. As used herein, a CARD-12 "chimeric protein" or "fusion protein" comprises a CARD-12 polypeptide operatively linked to a non-CARD-12 polypeptide. A "CARD-12 polypeptide" refers to a polypeptide having an amino acid sequence corresponding to all or a portion (preferably a biologically active portion) of a CARD-12, whereas a non-CARD-12 polypeptide" refers to a polypeptide having an amino acid sequence corresponding to a protein which is not substantially identical to the CARD-12 protein, e.g., a protein which is different from the CARD-12 proteins and which is derived from the same or a different organism. Within the fusion protein, the term "operatively linked" is intended to indicate that the CARD-12 polypeptide and the non-CARD-12 polypeptide are fused in-frame to each other. The heterologous polypeptide can be fused to the N-terminus or C-terminus of the CARD-12 polypeptide.

One useful fusion protein is a GST fusion protein in which the CARD-12 sequences are fused to the C-terminus of the GST sequences. Such fusion proteins can facilitate the purification of recombinant CARD-12. In another embodiment, the fusion protein contains a signal sequence from another protein. In certain host cells (e.g., mammalian host cells), expression and/or secretion of CARD-12 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a CARD-12-immunoglobulin fusion protein in which all or part of CARD-12 is fused to sequences derived from a member of the immunoglobulin protein family. The CARD-12-immunoglobulin fusion proteins of the invention can be incorporated into pharmaceutical compositions and administered to a subject to inhibit an interaction between a CARD-12 ligand and a CARD-12 protein on the surface of a cell, to thereby suppress CARD-12-mediated signal transduction in vivo. The CARD-12-immunoglobulin fusion proteins can be used to affect the bioavailability of a CARD-12 cognate ligand. Inhibition of the CARD-12 ligand/CARD-12 interaction may be useful therapeutically for both the treatment of proliferative and differentiative disorders, as well as modulating (e.g., promoting or inhibiting) cell survival. Moreover, the CARD-12-immunoglobulin fusion proteins of the invention can be used as immunogens to produce anti-CARD-12 antibodies in a subject, to purify CARD-12 ligands and in screening assays to identify molecules which inhibit the interaction of CARD-12 with a CARD-12 ligand.

Preferably, a CARD-12 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-12-encoding nucleic acid can be cloned into such an expression vector such that the fusion moiety is linked in-frame to the CARD-12 protein.

The present invention also pertains to variants of the CARD-12 proteins which function as either CARD-12 agonists (mimetics) or as CARD-12 antagonists. Variants of the CARD-12 protein can be generated by mutagenesis, e.g., discrete point mutation or truncation of the CARD-12 protein. An agonist of the CARD-12 protein can retain substantially the same, or a subset, of the biological activities of the naturally occurring form of the CARD-12 protein. An antagonist of the CARD-12 protein can inhibit one or more of the activities of the naturally occurring form of the CARD-12 protein by, for example, competitively binding to a downstream or upstream member of a cellular signaling cascade which includes the CARD-12 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-12 proteins.

Variants of the CARD-12 protein which function as either CARD-12 agonists (mimetics) or as CARD-12 antagonists can be identified by screening combinatorial libraries of mutants, e.g., truncation mutants of the CARD-12 protein for CARD-12 protein agonist or antagonist activity. In one embodiment, a variegated library of CARD-12 variants is generated by combinatorial mutagenesis at the nucleic acid level and is encoded by a variegated gene library. A variegated library of CARD-12 variants can be produced by, for example, enzymatically ligating a mixture of synthetic oligonucleotides into gene sequences such that a degenerate set of potential CARD-12 sequences is expressible as individual polypeptides, or alternatively, as a set of larger fusion proteins (e.g., for phage display) containing the set of CARD-12 sequences therein. There are a variety of methods which can be used to produce libraries of potential CARD-12 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-12 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-12, include fragments comprising or consisting of a domain or subdomain described herein, e.g., a kinase-2 domain or a CARD domain.

In addition, libraries of fragments of the CARD-12 protein coding sequence can be used to generate a variegated population of CARD-12 fragments for screening and subsequent selection of variants of a CARD-12 protein. In one embodiment, a library of coding sequence fragments can be generated by treating a double stranded PCR fragment of a CARD-12 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-12 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-12 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-12 variants (Arkin and Yourvan (1992) Proc. Natl. Acad. Sci. USA 89:7811–7815; Delgrave et al. (1993) Protein Engineering 6(3):327–331).

An isolated CARD-12 protein, or a portion or fragment thereof, can be used as an immunogen to generate antibodies that bind CARD-12 using standard techniques for polyclonal and monoclonal antibody preparation. The full-length CARD-12 protein can be used or, alternatively, the invention provides antigenic peptide fragments of CARD-12 for use as immunogens. The antigenic peptide of CARD-12 comprises at least 8 (preferably 10, 15, 20, or 30) amino acid residues of the amino acid sequence shown in SEQ ID NO:2 and encompasses an epitope of CARD-12 such that an antibody raised against the peptide forms a specific immune complex with CARD-12.

Useful antibodies include antibodies which bind to a domain or subdomain of CARD-12 described herein (e.g., a kinase-2 domain, a CARD domain, an NBS domain, a P-loop domain, or a LRR domain).

Preferred epitopes encompassed by the antigenic peptide are regions of CARD-12 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIG. 4).

A CARD-12 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-12 protein or a chemically synthesized CARD-12 polypeptide. The preparation can further include an adjuvant, such as Freund's complete or incomplete adjuvant, or similar immunostimulatory agent. Immunization of a suitable subject with an immunogenic CARD-12 preparation induces a polyclonal anti-CARD-12 antibody response.

Accordingly, another aspect of the invention pertains to anti-CARD-12 antibodies. The term "antibody" as used herein refers to immunoglobulin molecules and immunologically active portions of immunoglobulin molecules, i.e., molecules that contain an antigen binding site which specifically binds an antigen, such as CARD-12. A molecule which specifically binds to CARD-12 is a molecule which binds CARD-12, but does not substantially bind other molecules in a sample, e.g., a biological sample, which naturally contains CARD-12. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-12. The term "monoclonal antibody" or "monoclonal antibody composition", as used herein, refers to a population of antibody molecules that contain only one species of an antigen binding site capable of immunoreacting with a particular epitope of CARD-12. A monoclonal antibody composition thus typically displays a single binding affinity for a particular CARD-12 protein with which it immunoreacts.

Polyclonal anti-CARD-12 antibodies can be prepared as described above by immunizing a suitable subject with a CARD-12 immunogen. The anti-CARD-12 antibody titer in the immunized subject can be monitored over time by standard techniques, such as with an enzyme linked immunosorbent assay (ELISA) using immobilized CARD-12. If desired, the antibody molecules directed against CARD-12 can be isolated from the mammal (e.g., from the blood) and further purified by well-known techniques, such as protein A chromatography to obtain the IgG fraction. At an appropriate time after immunization, e.g., when the anti-CARD-12 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-12 immunogen as described above, and the culture supernatants of the resulting hybridoma cells are screened to identify a hybridoma producing a monoclonal antibody that binds CARD-12.

Any of the many well known protocols used for fusing lymphocytes and immortalized cell lines can be applied for the purpose of generating an anti-CARD-12 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-12, e.g., using a standard ELISA assay.

Alternative to preparing monoclonal antibody-secreting hybridomas, a monoclonal anti-CARD-12 antibody can be identified and isolated by screening a recombinant combinatorial immunoglobulin library (e.g., an antibody phage display library) with CARD-12 to thereby isolate immunoglobulin library members that bind CARD-12. Kits for generating and screening phage display libraries are commercially available (e.g., the Pharmacia Recombinant Phage Antibody System, Catalog No. 27–9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-CARD-12 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141: 4053–4060.

An anti-CARD-12 antibody (e.g., monoclonal antibody) can be used to isolate CARD-12 by standard techniques, such as affinity chromatography or immunoprecipitation. An anti-CARD-12 antibody can facilitate the purification of natural CARD-12 from cells and of recombinantly produced CARD-12 expressed in host cells. Moreover, an anti-CARD-12 antibody can be used to detect CARD-12 protein (e.g., in a cellular lysate or cell supernatant) in order to evaluate the abundance and pattern of expression of the CARD-12 protein. Anti-CARD-12 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243–56 (Alan R. Liss, Inc. 1985); Hellstrom et al., "Antibodies for Drug Delivery", in Controlled Drug Delivery (2nd Ed.), Robinson et al. (eds.), pp. 623–53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475–506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303–16 (Academic Press 1985), and Thorpe et al., "The Preparation and Cytotoxic Properties of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a CARD-12 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a CARD-12 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a CARD-12 polypeptide of the present invention wherein the composition comprises a polypeptide or polynucleotide of CARD-12. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially available software for conducting search means are and can be used in the computer-based systems of the present invention. Examples of such software include, but is not limited to, MacPattern (EMBL), BLASTIN and BLASTX (NCBIA).

For example, software that implements the BLAST (Altschul et al. (1990) *J. of Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding CARD-12 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-12 proteins, mutant forms of CARD-12, fusion proteins, etc.).

The recombinant expression vectors of the invention can be designed for expression of CARD-12 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident ë prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the CARD-12 expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (InVitrogen Corp, San Diego, Calif.).

Alternatively, CARD-12 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-12 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-12 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-12 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARD-12 protein. Accordingly, the invention further provides methods for producing CARD-12 protein using the host cells of the invention. In one embodiment, the method comprises culturing the host cell of the invention (into which a recombinant expression vector or isolated nucleic acid molecule encoding CARD-12 has been introduced) in a suitable medium such that CARD-12 protein is produced. In another embodiment, the method further comprises isolating CARD-12 from the medium or the host cell.

CARD-12 nucleic acid molecules can be used in viral gene delivery systems for gene therapy, e.g., adenoviral or retroviral gene delivery systems.

CARD-12 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) Nonviral Vectors for Gene Therapy, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by biobalistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site.

For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the HelioS™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyethyleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) BioTechniques 28:304–315).

The host cells of the invention can also be used to produce nonhuman transgenic animals. For example, in one embodiment, a host cell of the invention is a fertilized oocyte or an embryonic stem cell into which CARD-12-coding sequences have been introduced. Such host cells can then be used to create non-human transgenic animals in which exogenous CARD-12 sequences have been introduced into their genome or homologous recombinant animals in which endogenous CARD-12 sequences have been altered. Such animals are useful for studying the function and/or activity of CARD-12 and for identifying and/or evaluating modulators of CARD-12 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-12 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-12-encoding nucleic acid into the male pronuclei of a fertilized oocyte, e.g., by microinjection, retroviral infection, and allowing the oocyte to develop in a pseudopregnant female foster animal. The CARD-12 cDNA sequence, e.g., that of SEQ ID NO:1 or SEQ ID NO:3 can be introduced as a transgene into the genome of a non-human animal. Alternatively, a nonhuman homolog or ortholog of the human CARD-12 gene, such as a mouse CARD-12 gene, can be isolated based on hybridization to the human CARD-12 cDNA and used as a transgene. Intronic sequences and polyadenylation signals can also be included in the transgene to increase the efficiency of expression of the transgene. A tissue-specific regulatory sequence(s) can be operably linked to the CARD-12 transgene to direct expression of CARD-12 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-12 transgene in its genome and/or expression of CARD-12 mRNA in tissues or cells of the animals. A transgenic founder animal can then be used to breed additional animals carrying the transgene. Moreover, transgenic animals carrying a transgene encoding CARD-12 can further be bred to other transgenic animals carrying other transgenes.

To create an homologous recombinant animal, a vector is prepared which contains at least a portion of a CARD-12 gene (e.g., a human or a non-human homolog of the CARD-12 gene, e.g., a murine CARD-12 gene) into which a deletion, addition or substitution has been introduced to thereby alter, e.g., functionally disrupt, the CARD-12 gene. In an embodiment, the vector is designed such that, upon homologous recombination, the endogenous CARD-12 gene is functionally disrupted (i.e., no longer encodes a functional protein; also referred to as a "knock out" vector). Alternatively, the vector can be designed such that, upon homologous recombination, the endogenous CARD-12 gene is mutated or otherwise altered but still encodes functional protein (e.g., the upstream regulatory region can be altered to thereby alter the expression of the endogenous CARD-12 protein). In the homologous recombination vector, the altered portion of the CARD-12 gene is flanked at its 5' and 3' ends by additional nucleic acid of the CARD-12 gene to allow for homologous recombination to occur between the exogenous CARD-12 gene carried by the vector and an endogenous CARD-12 gene in an embryonic stem cell. The additional flanking CARD-12 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-12 gene has homologously recombined with the endogenous CARD-12 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

The CARD-12 nucleic acid molecules, CARD-12 proteins, and anti-CARD-12 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more addtional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-12 protein or anti-CARD-12 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304–315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-12 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-12 protein (e.g., via a recombinant expression vector in a host cell in gene therapy applications), to detect CARD-12 mRNA (e.g., in a biological sample) or a genetic lesion in a CARD-12 gene, and to modulate CARD-12 activity. In addition, the CARD-12 proteins can be used to screen drugs or compounds which modulate the CARD-12 activity or expression as well as to treat disorders characterized by insufficient or excessive production of CARD-12 protein or production of CARD-12 protein forms which have decreased or aberrant activity compared to CARD-12 wild type protein. In addition, the anti-CARD-12 antibodies of the invention can be used to detect and isolate CARD-12 proteins and modulate CARD-12 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-12 proteins or biologically active portions thereof or have a stimulatory or inhibitory effect on, for example, CARD-12 expression or CARD-12 activity. An example of a biologically active portion of human CARD-12 is amino acids 1–88 encoding a CARD domain.

Among the screening assays provided by the invention are screening to identify molecules that prevent the dimerization of CARD-12, screening to identify molecules which block the binding of a CARD containing polypeptide to CARD-12, and screening to identify a competitive inhibitor of the binding of a nucleotide to the nucleotide binding site of CARD-12. Screening assays, e.g., dimerization assays, can employ full-length CARD-12 or a portion of CARD-12, e.g., the CARD domain, the nucleotide binding site domain, or the NAIP homology domain.

In one embodiment, the invention provides assays for screening candidate or test compounds which bind to or modulate the activity of a CARD-12 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

Determining the ability of the test compound to modulate the activity of CARD-12 or a biologically active portion thereof can be accomplished, for example, by determining the ability of the CARD-12 protein to bind to or interact with a CARD-12 target molecule. As used herein, a "target molecule" is a molecule with which a CARD-12 protein binds or interacts in nature, for example, a molecule associated with the internal surface of a cell membrane or a cytoplasmic molecule. A CARD-12 target molecule can be a non-CARD-12 molecule or a CARD-12 protein or polypeptide of the present invention. In one embodiment, a CARD-12 target molecule is a component of an apoptotic signal transduction pathway. The target, for example, can be a second intracellular protein which has catalytic activity or a protein which facilitates the association of downstream signaling molecules with CARD-12.

Determining the ability of the test compound to modulate the activity of CARD-12 or a biologically active portion thereof can be accomplished, for example, by determining the ability of the CARD-12 protein to bind to or interact with any of the specific proteins listed in the previous paragraph as CARD-12 target molecules. In another embodiment, CARD-12 target molecules include all proteins that bind to a CARD-12 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the CARD-12 protein to bind to or interact with a CARD-12 target molecule can be accomplished by one of the methods described above for determining direct binding. In an embodiment, determining the ability of the CARD-12 protein to bind to or interact with a CARD-12 target molecule can be accomplished by determining the activity of the target molecule. For example, the activity of the target molecule can be determined by detecting the induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a CARD-12-responsive regulatory element operatively linked to a nucleic acid encoding a detectable marker, e.g. luciferase), or detecting a cellular response, for example, cell survival, cellular differentiation, or cell proliferation. In addition, and in another embodiment, genes induced by CARD-12 expression can be identified by expressing CARD-12 in a cell line and conducting a transcriptional profiling experiment wherein the mRNA expression patterns of the cell line transformed with an empty expression vector and the cell line transformed with a CARD-12 expression vector are compared. The promoters of genes induced by CARD-12 expression can be operatively linked to reporter genes suitable for screening such as luciferase, secreted alkaline phosphatase, or beta-galactosidase and the resulting constructs could be introduced into appropriate expression vectors. A recombinant cell line containing CARD-12 and transfected with an expression vector containing a CARD-12 responsive promoter operatively linked to a reporter gene can be used to identify test compounds that modulate CARD-12 activity by assaying the expression of the reporter gene in response to contacting the recombinant cell line with test compounds. CARD-12 agonists can be identified as increasing the expression of the reporter gene and CARD-12 antagonists can be identified as decreasing the expression of the reporter gene.

In another embodiment of the invention, the ability of a test compound to modulate the activity of CARD-12, or biologically active portions thereof can be determined by assaying the ability of the test compound to modulate CARD-12-dependent pathways or processes where the CARD-12 target proteins that mediate the CARD-12 effect are known or unknown. Potential CARD-12-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-12-dependent pathways or processes could be assayed by standard cell-based or cell free assays appropriate for the specific pathway or process under study.

In yet another embodiment, an assay of the present invention is a cell-free assay comprising contacting a CARD-12 protein or biologically active portion thereof with a test compound and determining the ability of the test compound to bind to the CARD-12 protein or biologically active portion thereof. Binding of the test compound to the CARD-12 protein can be determined either directly or indirectly as described above. In one embodiment, a competitive binding assay includes contacting the CARD-12 protein or biologically active portion thereof with a compound known to bind CARD-12 to form an assay mixture, contacting the assay mixture with a test compound, and determining the ability of the test compound to interact with a CARD-12 protein, wherein determining the ability of the test compound to interact with a CARD-12 protein comprises determining the ability of the test compound to preferentially bind to CARD-12 or biologically active portion thereof as compared to the known binding compound.

In another embodiment, an assay is a cell-free assay comprising contacting CARD-12 protein or biologically active portion thereof with a test compound and determining the ability of the test compound to modulate (e.g., stimulate or inhibit) the activity of the CARD-12 protein or biologically active portion thereof. Determining the ability of the test compound to modulate the activity of CARD-12 can be accomplished, for example, by determining the ability of the CARD-12 protein to bind to a CARD-12 target molecule by one of the methods described above for determining direct binding. In an alternative embodiment, determining the ability of the test compound to modulate the activity of CARD-12 can be accomplished by determining the ability of the CARD-12 protein to further modulate a CARD-12 target molecule. For example, the catalytic/enzymatic activity of the target molecule on an appropriate substrate can be determined as previously described.

In yet another embodiment, the cell-free assay comprises contacting the CARD-12 protein or biologically active portion thereof with a known compound which binds CARD-12 to form an assay mixture, contacting the assay mixture with a test compound, and determining the ability of the test compound to interact with a CARD-12 protein, wherein determining the ability of the test compound to interact with a CARD-12 protein comprises determining the ability of the CARD-12 protein to preferentially bind to or modulate the activity of a CARD-12 target molecule. The cell-free assays of the present invention are amenable to use of either the soluble form or a membrane-associated form of CARD-12. A membrane-associated form of CARD-12 refers to CARD-12 that interacts with a membrane-bound target molecule. In the case of cell-free assays comprising the membrane-associated form of CARD-12, it may be desirable to utilize a solubilizing agent such that the membrane-associated form of CARD-12 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CARD-12 or its target molecule to facilitate separation of complexed from uncomplexed forms of one or both of the proteins, as well as to accommodate automation of the assay. Binding of a test compound to CARD-12, or interaction of CARD-12 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CARD-12 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-12 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-12 binding or activity determined using standard techniques. In an alternative embodiment, MYC or HA epitope tag CARD-12 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-12 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-12 binding or activity determined using standard techniques.

Other techniques for immobilizing proteins on matrices can also be used in the screening assays of the invention. For example, CARD-12 or its target molecule can be immobilized utilizing conjugation of biotin and streptavidin. Biotinylated CARD-12 target molecules can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-12 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-12 or target molecule, as well as enzyme-linked assays which rely on detecting an enzymatic activity associated with the CARD-12 or a target molecule.

In another embodiment, modulators of CARD-12 expression are identified in a method in which a cell is contacted with a candidate compound and the expression of the CARD-12 promoter, mRNA or protein in the cell is determined. The level of expression of CARD-12 mRNA or protein in the presence of the candidate compound is compared to the level of expression of CARD-12 mRNA or protein in the absence of the candidate compound. The candidate compound can then be identified as a modulator of CARD-12 expression based on this comparison. For example, when expression of CARD-12 mRNA or protein is greater (statistically significantly greater) in the presence of the candidate compound than in its absence, the candidate compound is identified as a stimulator of CARD-12 mRNA or protein expression. Alternatively, when expression of CARD-12 mRNA or protein is less (statistically significantly less) in the presence of the candidate compound than in its absence, the candidate compound is identified as an inhibitor of CARD-12 mRNA or protein expression. The level of CARD-12 mRNA or protein expression in the cells can be determined by methods described herein for detecting CARD-12 mRNA or protein. The activity of the CARD-12 promoter can be assayed by linking the CARD-12 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the CARD-12 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-12 ("CARD-12-binding proteins" or "CARD-12-bp") and modulate CARD-12 activity. Such CARD-12-binding proteins are also likely to be involved in the propagation of signals by the CARD-12 proteins as, for example, upstream or downstream elements of the CARD-12 pathway.

The two-hybrid system is based on the modular nature of most transcription factors, which consist of separable DNA-binding and activation domains. Briefly, the assay utilizes two different DNA constructs. In one construct, the gene that codes for CARD-12 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CARD-12-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-12.

In an embodiment of the invention, the ability of a test compound to modulate the activity of CARD-12, or a biologically active portion thereof can be determined by assaying the ability of the test compound to block the binding of CARD-12 to its target proteins in a yeast or mammalian two-hybrid system assay. This assay could be automated for high throughput drug screening purposes. In another embodiment of the invention, CARD-12 and a target protein could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a CARD-12 physical interaction with a target protein would result in induction of a reporter gene in contrast to the normal two-hybrid system where inhibition of CARD-12 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to CARD-12. CARD-12 interactors could be configured into two-hybrid system baits and used in two-hybrid screens to identify additional members of the CARD-12 pathway. The interactors of CARD-12 interactors identified in this way could be useful targets for therapeutic intervention in CARD-12 related diseases and pathologies and an assay of their enzymatic or binding activity could be useful for the identification of test compounds that modulate CARD-12 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-12 nucleic acid molecules described herein or fragments thereof, can be used to map the location of CARD-12 genes on a chromosome. The mapping of the CARD-12 sequences to chromosomes is an important first step in correlating these sequences with genes associated with disease.

Briefly, CARD-12 genes can be mapped to chromosomes by preparing PCR primers (preferably 15–25 bp in length) from the CARD-12 sequences. Computer analysis of CARD-12 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-12 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-12 sequences to design oligonucleotide primers, sublocalization can be achieved with panels of fragments from specific chromosomes. Other mapping strategies which can similarly be used to map a CARD-12 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-12 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A CARD-12 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of the CARD-12 polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

2. Tissue Typing

The CARD-12 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-12 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-12 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from CARD-12 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the CARD-12 sequences or portions thereof, e.g., fragments derived from the noncoding regions of SEQ ID NO:1 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-12 probes can be used to identify tissue by species and/or by organ type.

In a similar fashion, these reagents, e.g., CARD-12 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-12 protein and/or nucleic acid expression as well as CARD-12 activity, in the context of a biological sample (e.g., blood, serum, cells, tissue) to thereby determine whether an individual is afflicted with a disease or disorder, or is at risk of developing a disorder, associated with aberrant CARD-12 expression or activity. The invention also provides for prognostic (or predictive) assays for determining whether an individual is at risk of developing a disorder associated with CARD-12 protein, nucleic acid expression or activity. For example, mutations in a CARD-12 gene can be assayed in a biological sample. Such assays can be used for prognostic or predictive purpose to thereby prophylactically treat an individual prior to the onset of a disorder characterized by or associated with CARD-12 protein, nucleic acid expression or activity.

Another aspect of the invention provides methods for determining CARD-12 protein, nucleic acid expression or CARD-12 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-12 in clinical trials.

These and other agents are described in further detail in the following sections.

1. Diagnostic Assays

An exemplary method for detecting the presence or absence of CARD-12 in a biological sample involves obtaining a biological sample from a test subject and contacting the biological sample with a compound or an agent capable of detecting CARD-12 protein or nucleic acid (e.g., mRNA, genomic DNA) that encodes CARD-12 protein such that the presence of CARD-12 is detected in the biological sample. An agent for detecting CARD-12 mRNA or genomic DNA is a labeled nucleic acid probe capable of hybridizing to CARD-12 mRNA or genomic DNA. The nucleic acid probe can be, for example, a full-length CARD-12 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to mRNA or genomic DNA. Other suitable probes for use in the diagnostic assays of the invention are described herein.

An agent for detecting CARD-12 protein can be an antibody capable of binding to CARD-12 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-12 mRNA, protein, or genomic DNA in a biological sample in vitro as well as in vivo. For example, in vitro techniques for detection of CARD-12 mRNA include Northern hybridizations and in situ hybridizations. In vitro techniques for detection of CARD-12 protein include enzyme linked immunosorbent assays (ELISAs), Western blots, immunoprecipitations and immunofluorescence. In vitro techniques for detection of CARD-12 genomic DNA include Southern hybridizations. Furthermore, in vivo techniques for detection of CARD-12 protein include introducing into a subject a labeled anti- CARD-12 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting CARD-12 protein, mRNA, or genomic DNA, such that the presence of CARD-12 protein, mRNA or genomic DNA is detected in the biological sample, and comparing the presence of CARD-12 protein, mRNA or genomic DNA in the control sample with the presence of CARD-12 protein, mRNA or genomic DNA in the test sample.

The invention also encompasses kits for detecting the presence of CARD-12 in a biological sample (a test sample). Such kits can be used to determine if a subject is suffering from or is at increased risk of developing a disorder associated with aberrant expression of CARD-12 (e.g., an immunological disorder). For example, the kit can comprise a labeled compound or agent capable of detecting CARD-12 protein or mRNA in a biological sample and means for determining the amount of CARD-12 in the sample (e.g., an anti-CARD-12 antibody or an oligonucleotide probe which binds to DNA encoding CARD-12, e.g., SEQ ID NO:1 or SEQ ID NO:3). Kits may also include instruction for observing that the tested subject is suffering from or is at risk of developing a disorder associated with aberrant expression of CARD-12 if the amount of CARD-12 protein or mRNA is above or below a normal level.

For antibody-based kits, the kit may comprise, for example: (1) a first antibody (e.g., attached to a solid support) which binds to CARD-12 protein; and, optionally, (2) a second, different antibody which binds to CARD-12 protein or the first antibody and is conjugated to a detectable agent. For oligonucleotide-based kits, the kit may comprise, for example: (1) a oligonucleotide, e.g., a detectably labelled oligonucleotide, which hybridizes to a CARD-12 nucleic acid sequence or (2) a pair of primers useful for amplifying a CARD-12 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-12.

2. Prognostic Assays

The methods described herein can furthermore be utilized as diagnostic or prognostic assays to identify subjects having or at risk of developing a disease or disorder associated with aberrant CARD-12 expression or activity. For example, the assays described herein, such as the preceding diagnostic assays or the following assays, can be utilized to identify a subject having or at risk of developing a disorder associated with CARD-12 protein, nucleic acid expression or activity.

Alternatively, the prognostic assays can be utilized to identify a subject having or at risk for developing such a disease or disorder. Thus, the present invention provides a method in which a test sample is obtained from a subject and CARD-12 protein or nucleic acid (e.g., mRNA, genomic DNA) is detected, wherein the presence of CARD-12 protein or nucleic acid is diagnostic for a subject having or at risk of developing a disease or disorder associated with aberrant CARD-12 expression or activity. As used herein, a "test sample" refers to a biological sample obtained from a subject of interest. For example, a test sample can be a biological fluid (e.g., serum), cell sample, or tissue. Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-12 expression or activity. For example, such methods can be used to determine whether a subject can be effectively treated with a specific agent or class of agents (e.g., agents of a type which decrease CARD-12 activity). Thus, the present invention provides methods for determining whether a subject can be effectively treated with an agent for a disorder associated with aberrant CARD-12 expression or activity in which a test sample is obtained and CARD-12 protein or nucleic acid is detected (e.g., wherein the presence of CARD-12 protein or nucleic acid is diagnostic for a subject that can be administered the agent to treat a disorder associated with aberrant CARD-12 expression or activity).

The methods of the invention can also be used to detect genetic lesions or mutations in a CARD-12 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-12-protein, or the mis-expression of the CARD-12 gene. For example, such genetic lesions can be detected by ascertaining the existence of at least one of 1) a deletion of one or more nucleotides from a CARD-12 gene; 2) an addition of one or more nucleotides to a CARD-12 gene; 3) a substitution of one or more nucleotides of a CARD-12 gene; 4) a chromosomal rearrangement of a CARD-12 gene; 5) an alteration in the level of a messenger RNA transcript of a CARD-12 gene; 6) aberrant modification of a CARD-12 gene, such as of the methylation pattern of the genomic DNA; 7) the presence of a non-wild type splicing pattern of a messenger RNA transcript of a CARD-12 gene (e.g., caused by a mutation in a splice donor or splice acceptor site); 8) a non-wild type level of a CARD-12-protein; 9) allelic loss of a CARD-12 gene; and 10) inappropriate post-translational modification of a CARD-12-protein. As described herein, there are a large number of assay techniques known in the art which can be used for detecting lesions in a CARD-12 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-12 gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-12 gene under conditions such that hybridization and amplification of the CARD-12-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-12 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in CARD-12 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-12 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-12 gene and detect mutations by comparing the sequence of the sample CARD-12 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-12 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type CARD-12 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl. Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-12 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-12 sequence, e.g., a wild-type CARD-12 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-12 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control CARD-12 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-12 gene.

Furthermore, any cell type or tissue, preferably peripheral blood leukocytes, in which CARD-12 is expressed may be utilized in the prognostic assays described herein.

3. Pharmacogenomics

Agents, or modulators which have a stimulatory or inhibitory effect on CARD-12 activity (e.g., CARD-12 gene expression) as identified by a screening assay described herein can be administered to individuals to treat (prophylactically or therapeutically) disorders (e.g., an immunological disorder) associated with aberrant CARD-12 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-12 protein, expression of CARD-12 nucleic acid, or mutation content of CARD-12 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of CARD-12 protein, expression of CARD-12 nucleic acid, or mutation content of CARD-12 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-12 modulator, such as a modulator identified by one of the exemplary screening assays described herein.

4. Monitoring of Effects During Clinical Trials

Monitoring the influence of agents (e.g., drugs, compounds) on the expression or activity of CARD-12 (e.g., the ability to modulate aberrant cell proliferation and/or differentiation) can be applied not only in basic drug screening, but also in clinical trials. For example, the effectiveness of an agent determined by a screening assay as described herein to increase CARD-12 gene expression, protein levels, or upregulate CARD-12 activity, can be monitored in clinical trails of subjects exhibiting decreased CARD-12 gene expression, protein levels, or downregulated CARD-12 activity. Alternatively, the effectiveness of an agent determined by a screening assay to decrease CARD-12 gene expression, protein levels, or downregulated CARD-12 activity, can be monitored in clinical trials of subjects exhibiting increased CARD-12 gene expression, protein levels, or upregulated CARD-12 activity. In such clinical trials, the expression or activity of CARD-12 and, preferably, other genes that have been implicated in, for example, a cellular proliferation disorder can be used as a "read out" or markers of the immune responsiveness of a particular cell.

For example, and not by way of limitation, genes, including CARD-12, that are modulated in cells by treatment with an agent (e.g., compound, drug or small molecule) which modulates CARD-12 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-12 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-12 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-12 protein, mRNA, or genomic DNA in the preadministration sample; (iii) obtaining one or more post-administration samples from the subject; (iv) detecting the level of expression or activity of the CARD-12 protein, mRNA, or genomic DNA in the post-administration samples; (v) comparing the level of expression or activity of the CARD-12 protein, mRNA, or genomic DNA in the pre-administration sample with the CARD-12 protein, mRNA, or genomic DNA in the post administration sample or samples; and (vi) altering the administration of the agent to the subject accordingly. For example, increased administration of the agent may be desirable to increase the expression or activity of CARD-12 to higher levels than detected, i.e., to increase the effectiveness of the agent. Alternatively, decreased administration of the agent may be desirable to decrease expression or activity of CARD-12 to lower levels than detected, i.e., to decrease the effectiveness of the agent.

5. Transcriptional Profiling

The CARD-12 nucleic acid molecules described herein, including small oligonucleotides, can be used in transcriptionally profiling. For example, these nucleic acids can be used to examine the expression of CARD-12 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-12, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-12 expression or activity, examples of which are provided herein.

1. Prophylactic Methods

In one aspect, the invention provides a method for preventing in a subject, a disease or condition associated with an aberrant CARD-12 expression or activity, by administering to the subject an agent which modulates CARD-12 expression or at least one CARD-12 activity. Subjects at risk for a disease which is caused or contributed to by aberrant CARD-12 expression or activity can be identified by, for example, any or a combination of diagnostic or prognostic assays as described herein. Administration of a prophylactic agent can occur prior to the manifestation of symptoms characteristic of the CARD-12 aberrancy, such that a disease or disorder is prevented or, alternatively, delayed in its progression. Depending on the type of CARD-12 aberrancy, for example, a CARD-12 agonist or CARD-12 antagonist agent can be used for treating the subject. The appropriate agent can be determined based on screening assays described herein.

2. Therapeutic Methods

Another aspect of the invention pertains to methods of modulating CARD-12 expression or activity for therapeutic purposes. The modulatory method of the invention involves contacting a cell with an agent that modulates one or more of the activities of CARD-12 protein activity associated with the cell. An agent that modulates CARD-12 protein activity can be an agent as described herein, such as a nucleic acid or a protein, a naturally-occurring cognate ligand of a CARD-12 protein, a peptide, a CARD-12 peptidomimetic, or other small molecule. In one embodiment, the agent stimulates one or more of the biological activities of CARD-12 protein. Examples of such stimulatory agents include active CARD-12 protein and a nucleic acid molecule encoding CARD-12 that has been introduced into the cell. In another embodiment, the agent inhibits one or more of the biological activities of CARD-12 protein. Examples of such inhibitory agents include antisense CARD-12 nucleic acid molecules and anti-CARD-12 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a CARD-12 protein or nucleic acid molecule or a disorder related to CARD-12 expression or activity. In one embodiment, the method involves administering an agent (e.g., an agent identified by a screening assay described herein), or combination of agents that modulates (e.g., upregulates or downregulates) CARD-12 expression or activity. In another embodiment, the method involves administering a CARD-12 protein or nucleic acid molecule as therapy to compensate for reduced or aberrant CARD-12 expression or activity.

Stimulation of CARD-12 activity is desirable in situations in which CARD-12 is abnormally downregulated and/or in which increased CARD-12 activity is likely to have a beneficial effect. Conversely, inhibition of CARD-12 activity is desirable in situations in which CARD-12 is abnormally upregulated, e.g., in myocardial infarction, and/or in which decreased CARD-12 activity is likely to have a beneficial effect.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising a nucleotide sequence that encodes a polypeptide comprising amino acid residues 1–88, 161–323, or 762–965 of SEQ ID NO:2.

2. The nucleic acid of claim 1, wherein the polypeptide comprises amino acid residues 1–88 of SEQ ID NO:2.

3. The nucleic acid of claim 1, wherein the polypeptide comprises amino acid residues 161–323 of SEQ ID NO:2.

4. The nucleic acid of claim 1, wherein the polypeptide comprises amino acid residues 762–965 of SEQ ID NO:2.

5. An isolated nucleic acid comprising a nucleotide sequence that encodes a polypeptide comprising the amino acid sequence of SEQ ID NO:2.

6. The nucleic acid of claim 5, wherein the polypeptide consists of the amino acid sequence of SEQ ID NO:2.

7. An isolated nucleic acid comprising a nucleotide sequence that encodes a polypeptide that binds to a caspase and comprises an amino acid sequence that is at least 95% identical to the sequence of SEQ ID NO:2, wherein the percent identity is determined using the ALIGN program in the GCG software package, using a PAM120 weight residue table, a gap length penalty of 12, and a gap penalty of 4.

8. The nucleic acid of claim 7, wherein the amino acid sequence is at least 98% identical to the sequence of SEQ ID NO:2.

9. The nucleic acid of claim 7, wherein the polypeptide comprises amino acid residues 1–88 of SEQ ID NO:2.

10. The nucleic acid of claim 7, wherein the polypeptide comprises amino acid residues 161–323 of SEQ ID NO:2.

11. The nucleic acid of claim 7, wherein the polypeptide comprises amino acid residues 762–965 of SEQ ID NO:2.

12. An isolated nucleic acid comprising a nucleotide sequence that encodes a polypeptide that induces apoptosis and comprises an amino acid sequence that is at least 95% identical to the sequence of SEQ ID NO:2, wherein the percent identity is determined using the ALIGN program in the GCG software package, using a PAM120 weight residue table, a gap length penalty of 12, and a gap penalty of 4.

13. The nucleic acid of claim 12, wherein the amino acid sequence is at least 98% identical to the sequence of SEQ ID NO:2.

14. The nucleic acid of claim 12, wherein the polypeptide comprises amino acid residues 1–88 of SEQ ID NO:2.

15. The nucleic acid of claim 12, wherein the polypeptide comprises amino acid residues 161–323 of SEQ ID NO:2.

16. The nucleic acid of claim 12, wherein the polypeptide comprises amino acid residues 762–965 of SEQ ID NO:2.

17. An isolated nucleic acid that comprises at least 650 nucleotides and hybridizes to a nucleic acid consisting of the sequence of SEQ ID NO:3 or the complement thereof under conditions of hybridization at 45° C. in 6.0× SSC followed by washing in 0.2× SSC, 0.1% SDS at 65° C., wherein the nucleic acid comprises a nucleotide sequence that encodes a polypeptide that binds to a caspase or induces apoptosis.

18. The nucleic acid of claim 17, wherein the nucleic acid comprises at least 1000 nucleotides.

19. The nucleic acid of claim 18, wherein the nucleic acid comprises at least 1600 nucleotides.

20. The nucleic acid of claim 19, wherein the nucleic acid comprises at least 2100 nucleotides.

21. The nucleic acid of claim 17, wherein the polypeptide binds to a caspase.

22. The nucleic acid of claim 17, wherein the polypeptide induces apoptosis.

23. An isolated nucleic acid comprising a nucleotide sequence that is at least 95% identical to the nucleotide sequence of SEQ ID NO:3, wherein the percent identity is determined using the NBLAST program with a score of 100 and a word length of 12, wherein the nucleotide sequence encodes a polypeptide that binds to a caspase or induces apoptosis.

24. The nucleic acid of claim 23, wherein the nucleotide sequence is at least 98% identical to the nucleotide sequence of SEQ ID NO:3.

25. The nucleic acid of claim 23, wherein the polypeptide binds to a caspase.

26. The nucleic acid of claim 23, wherein the polypeptide induces apoptosis.

27. An isolated nucleic acid comprising the nucleotide sequence of SEQ ID NO:3.

28. The nucleic acid of claim 27, wherein the nucleic acid comprises the nucleotide sequence of SEQ ID NO:1.

29. The nucleic acid of claim 1, further comprising a sequence encoding a heterologous polypeptide.

30. A vector comprising the nucleic acid of claim 1.

31. The vector of claim 30, wherein the vector comprises nucleic acid sequences which regulate expression of a polypeptide encoded by the nucleic acid.

32. A host cell comprising the vector of claim 31.

33. The host cell of claim 32, which is a mammalian host cell.

34. A method for producing a polypeptide, the method comprising culturing the host cell of claim 32 under conditions in which the nucleic acid is expressed.

35. A kit comprising the nucleic acid of claim 1 or a complement thereof, and instructions for use.

* * * * *